US008575169B2

(12) United States Patent
Chang et al.

(10) Patent No.: US 8,575,169 B2
(45) Date of Patent: *Nov. 5, 2013

(54) METHOD OF TREATING SEXUAL DYSFUNCTIONS WITH DELTA OPIOID RECEPTOR AGONIST COMPOUNDS

(75) Inventors: Kwen-Jen Chang, Chapel Hill, NC (US); Klim King, Chapel Hill, NC (US); Kestutis P. Biciunas, Durham, NC (US); Robert W. McNutt, Jr., Durham, NC (US); William Pendergast, Durham, NC (US); Shyi-Tai Jan, Cary, NC (US)

(73) Assignee: Versi Group, LLC, Gladstone, NJ (US)

( * ) Notice: Subject to any disclaimer, the term of this patent is extended or adjusted under 35 U.S.C. 154(b) by 578 days.

This patent is subject to a terminal disclaimer.

(21) Appl. No.: 10/335,764

(22) Filed: Jan. 2, 2003

(65) Prior Publication Data

US 2003/0186872 A1   Oct. 2, 2003
US 2013/0053326 A9   Feb. 28, 2013

Related U.S. Application Data

(63) Continuation-in-part of application No. 10/282,411, filed on Oct. 29, 2002, now Pat. No. 7,030,124.

(60) Provisional application No. 60/345,216, filed on Jan. 2, 2002, provisional application No. 60/337,887, filed on Nov. 2, 2001, provisional application No. 60/340,084, filed on Oct. 29, 2001.

(51) Int. Cl.
*A61K 31/497* (2006.01)

(52) U.S. Cl.
USPC ...................................... 514/252.12; 514/730

(58) Field of Classification Search
USPC ........................................... 514/252.12, 730
See application file for complete search history.

(56) References Cited

U.S. PATENT DOCUMENTS

| | | | |
|---|---|---|---|
| 5,063,929 A | 11/1991 | Bartelt et al. |
| 5,151,448 A | 9/1992 | Crenshaw et al. |
| 5,276,042 A | 1/1994 | Crenshaw et al. |
| 5,552,404 A | 9/1996 | Chang et al. |
| 5,574,159 A | 11/1996 | Chang et al. |
| 5,587,167 A | 12/1996 | Choi et al. |
| 5,658,908 A | 8/1997 | Chang et al. |
| 5,681,830 A | 10/1997 | Chang et al. |
| 5,707,999 A | 1/1998 | Cavallini |
| 5,807,858 A | 9/1998 | Chang et al. |
| 5,854,249 A | 12/1998 | Chang et al. |
| 5,929,054 A | 7/1999 | Baker et al. |
| 5,985,880 A | 11/1999 | Chang et al. |
| 6,130,222 A | 10/2000 | Roberts et al. |
| 6,187,792 B1 | 2/2001 | Delorme et al. |
| 6,200,978 B1 | 3/2001 | Maw et al. |
| 6,228,864 B1 | 5/2001 | Smith et al. |
| 6,300,332 B1 | 10/2001 | Chang et al. |
| 2002/0052007 A1 | 5/2002 | Chang et al. |
| 2002/0132857 A1 | 9/2002 | Bar-Or |
| 2003/0036552 A1 | 2/2003 | Brown et al. |

FOREIGN PATENT DOCUMENTS

| | | |
|---|---|---|
| WO | 93/15062 | 8/1993 |
| WO | 97/36867 | 10/1997 |
| WO | 98/14433 | 4/1998 |
| WO | WO 98/52929 | 11/1998 |
| WO | WO 01/74804 A1 | 10/2001 |
| WO | WO 01/74805 A1 | 10/2001 |
| WO | WO 01/74806 | 10/2001 |
| WO | WO 01/74806 A1 | 10/2001 |

OTHER PUBLICATIONS

Kim, et al., "Short Term Analysis of the Effects of As Needed Use of Sertraline At 5pm for the Treatment of Premature Ejaculation", Adult Urology CME Article, 1999, pp. 544-547.
Waldinger, et al., "Premature Ejaculation and Serotergic Antidepressants-Induced Delayed Ejeculation. The Involvement of the Serotonergic System", Behavioral Brain Research, vol. 92, 111-118, (1998).
Stanley G. Korenman, "New Insights Into Erectile Dysfunction: A Practical Approach", The American Journal of Medicine, vol. 105, 135-144, Aug. 1998.
Rowland, et al., "Ejaculatory Latency and Control in Men With Premature Ejaculation: An Analysis Across Sexual Activities Using Multiple Sources of Information", Journal of Psychosomatic Research, vol. 48, 69-77, (2000).
Mos, et al., "A Comparison of the Effects of Different Serotonin Reuptake Blockers on Sexual Behavior of the Male Rat", European Neuropsychopharmacology, vol. 9, 123-135, (1999).
Hsieh, et al., "An In Vivo Evaluation of the Therapeutic Potential of Sympatholytic Agents on Premature Ejaculation", BJU International, vol. 84, 503-506, (1999).
Matitiahu Berkovitch et al.; Efficacy of Prilocaine-Lidocaine Cream in the Treatment of Premature Ejaculation; Journal of Urology; vol. 154, No. 4, pp. 1360-1361 (1995).
Peter Forster et al.; Fluoxetine for Premature Ejaculation; The American Journal of Psychiatry; vol. 151, No. 10 p. 1523 (1994).
Ardent Pharmaceuticals, Inc. Supplemental European Search Report corresponding to European Application No. 03710631.7, dated Feb. 11, 2008.

*Primary Examiner* — Sreeni Padmanabhan
*Assistant Examiner* — Shoba Kantamneni
(74) *Attorney, Agent, or Firm* — Marianne Fuierer; Moore & Van Allen, PLLC

(57) ABSTRACT

Compositions and methods for treatment of sexual dysfunctions by administering to a subject a pharmaceutical composition comprising a delta opioid receptor agonist in an amount effective to delay the onset of ejaculation in the subject during sexual stimulation.

5 Claims, 4 Drawing Sheets

METHOD OF TREATING SEXUAL DYSFUNCTIONS WITH DELTA OPIOID RECEPTOR AGONIST COMPOUNDS

CROSS-REFERENCE TO RELATED APPLICATION

This application claims priority from U.S. Provisional Patent Application No. 60/345,216 filed on Jan. 2, 2002 and is a Continuation-in-Part Application of and claims priority to U.S. patent application Ser. No. 10/282,411 filed on Oct. 29, 2002, now U.S. Pat. No. 7,030,124, which in turn claimed priority to U.S. Provisional Patent Application No. 60/337,887 filed on Nov. 2, 2001 and U.S. Provisional Patent Application No. 60/340,084, filed on Oct. 29, 2001.

BACKGROUND OF THE INVENTION

1. Field of the Invention

The present invention relates to compositions and methods of treatment for sexual dysfunctions, and more particularly, to the treatment of premature ejaculation in male subjects by administration of delta receptor agonist compound(s), optionally in combination with other agents.

2. Description of the Related Art

Premature ejaculation is one of the most common male sexual dysfunctions, estimated to affect up to 40% of men, irrespective of age. Premature ejaculation is defined as a persistent or recurrent ejaculation with minimal sexual stimulation before, on or shortly after penetration. Although premature ejaculation is common, there is some disagreement on its precise cause and treatment.

The reasons for premature ejaculation are generally thought to include a malfunction of the repressor center due to the fatigue of nervous transmission, hypersensitivity of a specific site due to genital disorders, hormonal disorders, physical problems and the like. It is believed that the premature ejaculation is generally caused by a complex interaction of the above-mentioned reasons or by a loss of cooperation among the related sexual nerve centers.

Premature ejaculation has been treated with psychotherapy and drug therapy. Psychotherapy requires sexual training for a long period of time, which involves discussions and cooperation with a physician and the patient and his partner. However, since psychotherapy necessitates a long period of time for the doctor, patient and partner to work together in order to be effective, its success rate is low. That is, changes in living style, external stress, etc., undermine its success such that the problem is never solved or it reoccurs. Therefore, drug therapy is now more widely used since time restrictions are not as great.

Methods for treating premature ejaculation by systemic administration of several different antidepressant compounds have been described in U.S. Pat. Nos. 5,151,448 and 5,276,042. However, these drugs may not be effective for all patients, and the side effects of these drugs can halt treatment or impair patient compliance. Disease states or adverse interactions with other drugs may contraindicate the use of these compounds or require lower dosages that may not be effective to delay the onset of ejaculation. Additionally, the stigma of mental illness associated with antidepressant therapy can discourage patients from beginning or continuing such treatments.

Administration of the antidepressant fluoxetine has been claimed to treat premature ejaculation (U.S. Pat. No. 5,151,448). However, the administration of fluoxetine has many undesired aspects. Patients with hepatic or renal impairments may not be able to use fluoxetine due to its metabolism in the liver and excretion via the kidney. Systemic events during fluoxetine treatment involving the lungs, kidneys or liver have occurred, and death has occurred from overdoses. In addition, side effects of oral fluoxetine administration include hair loss, nausea, vomiting, dyspepsia, diarrhea, anorexia, anxiety, nervousness, insomnia, drowsiness, fatigue, headache, tremors, dizziness, convulsions, sweating and skin rashes. Fluoxetine interacts with a range of drugs, often by impairing their metabolism by the liver.

U.S. Pat. No. 5,276,042 describes the administration of paroxetine for the treatment of premature ejaculation. Paroxetine is predominantly excreted in the urine, and decreased doses are recommended in patients with hepatic and renal impairments. Paroxetine cannot be given to patients undergoing treatment with a monoamine oxidase inhibitor. Side effects from oral administration of paroxetine include hyponatremia, asthenia, sweating, nausea, decreased appetite, oropharynx disorder, somnolence, dizziness, insomnia, tremors, anxiety, impaired micturition, weakness and paresthesia.

Other therapies include the application of local anesthetics for blunting the sensitivity of the sexual peripheral nerve. However, local anesthetics, such as lidocaine ointment or spray, may induce vasoconstriction, which may lead to transient erectile failure, and can be transferred to sexual partners thereby decreasing their sensitivity and pleasure as well.

Thus, present day drug therapy cannot successfully solve the problems associated with premature ejaculation. Accordingly there is a need for a method of treating premature ejaculation that requires no specialized psychological therapy, can be used conveniently and without embarrassment, and does not involve the problems associated with prior therapeutic methods.

SUMMARY OF THE INVENTION

The present invention relates in one aspect to a method of treating premature ejaculation by administering to a subject a pharmaceutical composition comprising a delta opioid receptor agonist in an amount effective to delay the onset of ejaculation during sexual stimulation. The delta opioid receptor agonist is either peptidic or non-peptidic. The pharmaceutical formulation may further comprise an additional active agent, e.g., Viagra® (sildenafil citrate), Prozac® (fluoxetine), vasoactive agents and combination of two or more thereof.

One aspect of the present invention provides a method for delaying the onset of ejaculation in a subject during sexual stimulation comprising administering to the subject an effective amount of at least one compound of the formulae:

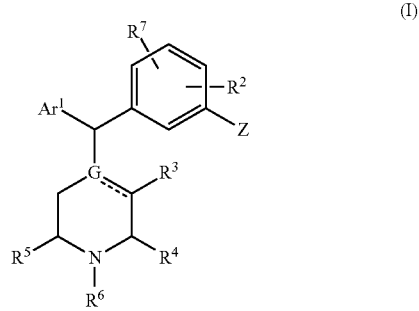

wherein:
Ar¹ is a 5- or 6-member carbocyclic or heterocyclic aromatic ring with atoms selected from the group consisting of carbon, nitrogen, oxygen and sulfur and may include thiophenyl, thiazolyl, furanyl, pyrrolyl, phenyl, or pyridyl, and having on a first carbon atom thereof a substituent Y and on a second ring carbon thereof a substituent $R^1$, Y is selected from the group consisting of:
hydrogen;
halogen;
$C_1$-$C_6$ alkyl, $C_2$-$C_6$ alkenyl, $C_2$-$C_6$ alkynyl;
$C_1$-$C_6$ haloalkyl;
$C_1$-$C_6$ alkoxy;
$C_3$-$C_6$ cycloalkoxy;
sulfides of the formula $SR^8$ where $R^8$ is $C_1$-$C_6$ alkyl, $C_2$-$C_6$ alkenyl, $C_2$-$C_6$ alkynyl, $C_3$-$C_6$ cycloalkyl, arylalkyl having a $C_5$-$C_{10}$ aryl moiety and an $C_1$-$C_6$ alkyl moiety, or $C_5$-$C_{10}$ aryl;
sulfoxides of the formula $SOR^8$ where $R^8$ is the same as above;
sulfones of the formula $SO_2R^8$ where $R^8$ is the same as above;
nitrile;
$C_1$-$C_6$ acyl;
alkoxycarbonylamino(carbamoyl) of the formula $NHCO_2R^8$ where $R^8$ is the same as above;
carboxylic acid, or an ester, amide, or salt thereof;
aminomethyl of the formula $CH_2NR^9R^{10}$ where $R^9$ and $R^{10}$ may be the same or different, and may be hydrogen, $C_1$-$C_6$ alkyl, $C_2$-$C_6$ alkenyl, $C_2$-$C_6$ alkynyl, $C_2$-$C_6$ hydroxyalkyl, $C_2$-$C_6$ methoxyalkyl, $C_3$-$C_6$ cycloalkyl, or $C_5$-$C_{10}$ aryl, or $R^9$ and $R^{10}$ together may form a ring of 5 or 6 atoms, the ring atoms selected from the group consisting of N and C;
carboxamides of the formula $CONR^9R^{10}$ where $R^9$ and $R^{10}$ are the same as above, or $C_2$-$C_{30}$ peptide conjugates thereof; and
sulfonamides of the formula $SO_2NR^9R^{10}$ where $R^9$ and $R^{10}$ are the same as above;

Z is selected from the group consisting of:
hydrogen, hydroxy and carboxy and esters thereof;
alkoxy-carboxylic acid, —$OCH_3COOH$, —$ORCOOH$;
alkoxy, carboxyalkoxy, hydroxymethyl, and esters thereof; and
amino, carboxamides and sulfonamides thereof;
G is carbon or nitrogen;
$R^1$ is hydrogen, halogen, or $C_1$-$C_4$ alkyl, $C_2$-$C_4$ alkenyl, $C_2$-$C_4$ alkynyl;
$R^2$ is hydrogen, halogen, or $C_1$-$C_4$ alkyl, $C_2$-$C_4$ alkenyl, $C_2$-$C_4$ alkynyl;
$R^3$, $R^4$ and $R^5$ may be the same or different, and are independently selected from hydrogen and methyl, and wherein at least one of $R^3$, $R^4$ or $R^5$ is not hydrogen, subject to the proviso that the total number of methyl groups does not exceed two, or any two of $R^3$, $R^4$ and $R^5$ together may form a bridge of 1 to 3 carbon atoms;
$R^6$ is selected from the group consisting of:
hydrogen;
$C_1$-$C_6$ alkyl, $C_2$-$C_6$ alkenyl, $C_2$-$C_6$ alkynyl;
$C_3$-$C_6$ cycloalkyl;
arylalkyl having $C_5$-$C_{10}$ aryl and $C_1$-$C_6$ alkyl moieties;
alkoxyalkyl having $C_1$-$C_4$ alkoxy and $C_1$-$C_4$ alkyl moieties;
$C_2$-$C_4$ cyanoalkyl;
$C_2$-$C_4$ hydroxyalkyl;
aminocarbonylalkyl having a $C_1$-$C_4$ alkyl moiety; and $R^{12}COR^{13}$, where $R^{12}$ is $C_1$-$C_4$ alkylene, and $R^{13}$ is $C_1$-$C_4$ alkyl or $C_1$-$C_4$ alkoxy or hydroxy, or $R^6$ is

and $Ar^2$ is a 5 or 6-member carbocyclic or heterocyclic aromatic ring with atoms selected from the group consisting of carbon, nitrogen, oxygen and sulfur, and having on a carbon atom thereof a substituent X, wherein X is selected from the group consisting of a halogen (fluorine, bromine, chlorine, iodine), hydrogen, hydroxy and esters thereof, carboxy and esters thereof; $C_1$-$C_4$ carboxy alkyl and esters thereof; alkyl carboxylic acid, carboxylic acid, alkoxy, hydroxymethyl, and esters thereof; and amino, and carboxamides and sulfonamides thereof; and $R^7$ is hydrogen or fluorine;

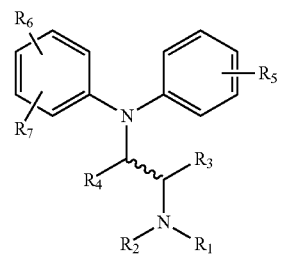

(II)

wherein
$R_1$ and $R_2$, which can be the same or different, are each hydrogen, linear or branched $C_{1-6}$ alkyl, $C_{3-7}$ cycloalkyl, $C_{3-7}$ cycloalkenyl, $C_{4-6}$ cycloalkylalkyl, $C_{3-6}$ alkenyl, $C_{3-5}$ alkynyl, aryl, aralkyl or furan-2 or 3-yl alkyl or may form together a $C_{3-7}$ alkyl ring which may be interrupted by oxygen.

$R_3$ and $R_4$, which can be the same or different, are each hydrogen, linear or branched $C_{1-6}$ alkyl, or $R_4$ is oxygen forming with the carbon atom to which is attached a C=O group;

$R_5$ is hydrogen, hydroxy, $C_{1-3}$ alkoxy, thiol or alkylthio;

$R_6$ is phenyl, halogen, $NH_2$ or a para or meta —C(Z)—$R_8$ group, in which Z is oxygen or sulphur;

$R_8$ is $C_{1-8}$-alkyl, $C_{1-8}$-alkoxy or $NR_9R_{10}$, wherein $R_9$ and $R_{10}$, which may be the same or different, are hydrogen, straight or branched $C_{1-6}$ alkyl, $C_{3-7}$ cycloalkyl, $C_{4-6}$ cycloalkylalkyl, $C_{3-6}$ alkenyl, aryl or aralkyl, or $R_6$ is a para or meta

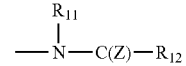

group
in which $R_{11}$ and $R_{12}$ which may the same or different are hydrogen, straight or branched $C_{1-6}$ alkyl, $C_{3-7}$ cycloalkyl, $C_{4-6}$ cycloalkylalkyl, $C_{3-6}$ alkenyl, aryl, aralkyl or an optionally substituted heterocyclic ring, and Z is as defined above; and, $R_7$ is hydrogen, straight or branched $C_{1-8}$ alkyl or halogen;

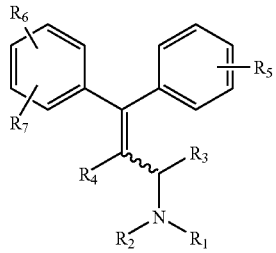

(III)

wherein, $R_1$ and $R_2$, can be the same or different, are each hydrogen, linear or branched $C_{1-6}$ alkyl, $C_{3-7}$ cycloalkyl, $C_{3-7}$ cycloalkenyl, $C_{4-6}$ cycloalkylalkyl, $C_{3-6}$ alkenyl, $C_{3-5}$ alkynyl, aryl, aralkyl or furan-2 or 3-yl alkyl or may form together a $C_{3-7}$ alkyl ring which may be interrupted by oxygen.

$R_3$ and $R_4$, can be the same or different, are each hydrogen, linear or branched $C_{1-6}$ alkyl;

$R_5$ is hydroxy, $C_{1-6}$ alkoxy, thiol or alkylthio;

$R_6$ is a —C(Z)—$R_8$ group, wherein Z is oxygen or sulphur, $R_8$ is $C_{1-8}$-alkyl, $C_{1-8}$-alkoxy or $NR_9R_{10}$, wherein $R_9$ and $R_{10}$, which may be the same or different, are hydrogen, straight or branched $C_{1-6}$ alkyl, $C_{3-7}$ cycloalkyl, $C_{4-6}$ cycloalkylalkyl, $C_{3-6}$ alkenyl, aryl or aralkyl, or $R_6$ is

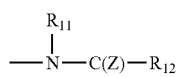

group wherein $R_{11}$ and $R_{12}$ have the same meaning as $R_9$ and $R_{10}$ or together form an optionally substituted heterocyclic ring and Z is as defined above, and $R_7$ is hydrogen, straight or branched $C_{1-8}$ alkyl or halogen;

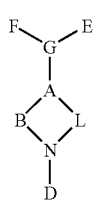

(IV)

wherein
A is N or C—X
wherein
X is H or $C_{1-4}$ alkyl;
G is C—Y
wherein
Y is H or $C_{1-4}$ alkyl;
B is an optional $C_{1-6}$ hydrocarbyl group, optionally substituted;
L is an optional $C_{1-6}$ hydrocarbyl group, optionally substituted;

and wherein A, B, and L in combination with the N constitute a first ring structure which has from 5-7 atoms in the ring;
further wherein:
either D is H or a $C_{1-10}$ hydrocarbyl group,
or D is a $C_{1-10}$ hydrocarbyl group linked to B or L to form a second ring structure which includes the N of the first ring structure, which second ring structure is fused to the first ring structure and which second ring structure has from 5-7 atoms in the ring;
E is a phenyl group substituted by at least one or more of hydroxy, $C_{1-4}$ alkoxy, or $NH_2SO_2$ $C_{1-4}$ alkylene;
F represents a combination of a phenyl group and a heterocyclic group, wherein
(i) the phenyl group is positioned intermediate (in between) G and the heterocyclic group;
(ii) the phenyl group is fused to the heterocyclic group or is linked directly to the heterocyclic group or is attached via a spacer group to the heterocyclic group, wherein the spacer group is any one of $C_{1-4}$ alkylene, carbonyl or $SO_2$; and
(iii) the heterocyclic group is substituted by at least one or more of: a COOH group, a bio-isostere of a COOH group, a biolabile ester derivative of a COOH group, a $C_{1-10}$ hydrocarbyl group comprising one or more COOH groups, a $C_{1-10}$ hydrocarbyl group comprising one or more bio-isosteres of a COOH group, or a $C_{1-10}$ hydrocarbyl group comprising one or more biolabile ester derivatives of a COOH group;
and pharmaceutically acceptable esters and salts of compounds (I)-(IV).

The pharmaceutical composition of the present invention may comprises an amount effective to treat sexual dysfunction with at least one a delta opioid receptor agonist described in the following references, the contents of which are incorporated by reference herein in their entirety for all purposes:
Chang et al. U.S. Pat. No. 5,658,908 issued Aug. 19, 1997;
Chang et al. U.S. Pat. No. 5,681,830 issued Oct. 28, 1997;
Chang et al. U.S. Pat. No. 5,552,404 issued Sep. 3, 1996;
Chang et al. U.S. Pat. No. 5,574,159 issued Nov. 12, 1996;
Chang et al. U.S. Pat. No. 5,854,249 issued Dec. 29, 1998;
Chang et al. U.S. Pat. No. 5,807,858 issued Sep. 15, 1998;
Chang et al. U.S. Pat. No. 5,985,880 issued Nov. 16, 1999;
Chang et al. U.S. Pat. No. 6,300,332 issued Oct. 9, 2001;
WO 0146263;
U.S. Pat. No. 6,130,222;
U.S. Pat. No. 6,187,792;
WO 0174804;
WO 9852929;
WO 0174805; and
WO 0174806.

In another aspect of the invention, a pharmaceutical composition is provided for carrying out the methods of the invention. The pharmaceutical composition comprises an effective amount of a delta opioid receptor agonist as provided herein, a pharmacologically acceptable carrier, and optionally another active agent. Other types of components may be incorporated into the composition as well, e.g., excipients, surfactants, preservatives, stabilizers, chelating agents and the like, as will be appreciated by those skilled in the art of pharmaceutical composition preparation and drug delivery.

Administration of the pharmaceutical composition is carried out within the context of a predetermined dosing regime such that the delta opioid receptor agonist is effective in the treatment of premature ejaculation.

Delivery of the pharmaceutical compositions may be accomplished through any route effective to provide relief from premature ejaculation, including, oral, rectal, topical, sub-lingual, mucosal, nasal, ophthalmic, subcutaneous, intramuscular, intravenous, transdermal, spinal, intrathecal, intraarticular, intra-arterial, sub-arachnoid, bronchial, lymphatic, transurethral, intracavernosal injection and urethral suppository administration.

Yet another aspect of the present invention relates to damping male sexual response or diminishing sexual libido in a subject by administering to the subject in need thereof, an effective amount of a delta opioid receptor agonist.

Various other aspects, features and embodiments of the invention will be more fully apparent from the ensuing disclosure and appended claims.

DETAILED DESCRIPTION OF THE INVENTION, AND PREFERRED EMBODIMENTS THEREOF

Figure 1:
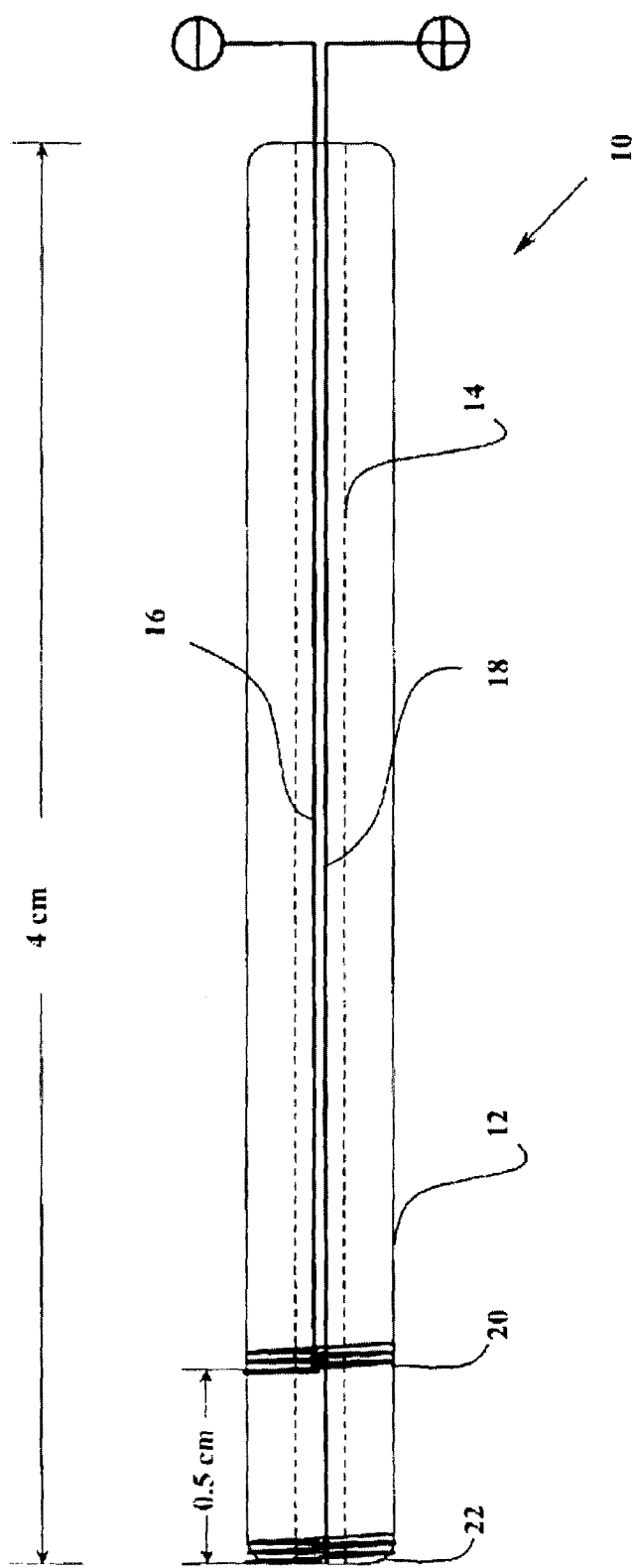
FIG. 1 is a longitudinal cross-sectional view of an electric bipolar rectal probe used for inducing ejaculation, according to one embodiment of the present invention.
Figure 2:
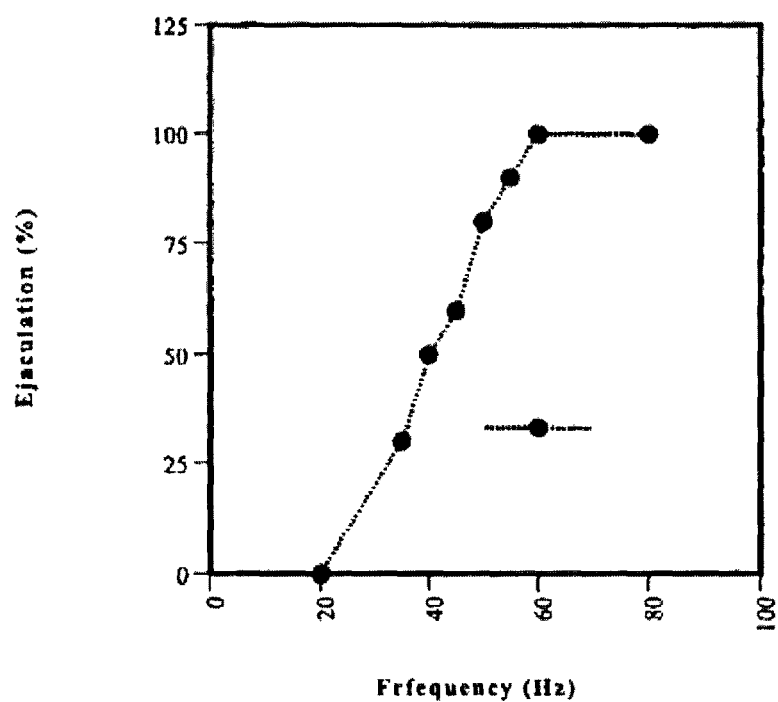
FIG. 2 illustrates the dependence of ejaculation on the oscillating frequency of the stimulating electricity.

Delta opioid receptors are present in the central and peripheral nervous systems of many species, including man. The delta opioid receptor has been identified as having a role in many bodily functions, such as circulatory and pain systems, immunomodulatory activities, and gastrointestinal disorders.

Agonists are agents that recognize and bind to the delta receptors thereby affecting biochemical and/or physiological pathways. One of the major neuronal effects of opioid receptor activation is blocking the release and liberation of neurotransmitters. The neurotransmitter adrenaline is liberated by postganglic sympathetic nerve, which initiates the contraction of smooth muscle surrounding the seminal vesicle and prostate gland that leads to semen emission. Likewise, the parasympathetic nerve liberates a neurotransmitter that initiates contraction of the bulbocarvernous muscle surrounding the penis, which leads to forcible ejection of semen from the urethra. While not wishing to be bound by any specific mechanism of action, it is believed that the activation of the delta opioid receptor leads to inhibiting the release of adrenaline or acetylcholine from sympathetic and parasympathetic nerve endings, and consequently prevents smooth muscle from contraction with a concomitant delay of ejaculation. It is noteworthy to point out that heretofore no reference appears in the literature about any possible use of delta opioid receptor agonists, either peptidic or non-peptidic, in treatment of premature ejaculation.

DEFINITIONS

Before describing the present invention in detail, it is to be understood that this invention is not limited to particular drug delivery systems. It is also to be understood that the terminology used herein is for the purpose of describing particular embodiments only, and is not intended to be limiting.

In describing and claiming the present invention, the following terminology will be used in accordance with the definitions set out below.

The terms "active agent," as used herein means a chemical material or compound which, when administered to an organism (human or animal) induces a desired pharmacologic effect. Included are derivatives and analogs of those compounds or classes of compounds specifically mentioned which also induce the desired pharmacologic effect.

The terms "transurethral," "intraurethral" and "urethral" to specify the mode of administration as used herein are used interchangeably to refer to delivery of the drug into the urethra such that the drug contacts and passes through the wall of the urethra.

The term "intracavemosal" as used herein means another mode of drug administration and involves injection into one or both corpora of the corpora cavernosal tissues of the penis.

By the term "transdermal" delivery, applicants intend to include both transdermal (or "percutaneous") and transmucosal administration, i.e., delivery by passage of a drug through the skin or mucosal tissue and into the bloodstream.

The term "topical administration" is used in its conventional sense to mean delivery of a topical drug or pharmacologically active agent to the skin or mucosa.

"Carriers" or "vehicles" as used herein means carrier materials suitable for drug administration. Carriers and vehicles useful herein include any such materials known in the art, e.g., any liquid, gel, solvent, liquid diluent, solubilizer, or the like, which is nontoxic and which does not interact with other components of the composition in a deleterious manner.

By an "effective" amount of a drug or pharmacologically active agent is meant a nontoxic but sufficient amount of the drug or agent to provide the desired effect.

Active Agents for Treating Premature Ejaculation

In order to carry out the method of the invention, at lease one delta opioid receptor agonist is administered to male subject with a history of premature ejaculation. In a first embodiment, suitable delta opioid receptor agonists that can be administered to treat premature ejaculation include, but are not limited to;

deltorphin I (Tyr-D-Ala-Phe-Asp-Val-Val-Gly-NH$_2$);
deltorphin II (Tyr-D-Ala-Phe-Glu-Val-Val-Gly-HH$_2$);
Biphalin;
DADLE [D-Ala$^2$,D-Leu$^5$]enkephalin;
[D-Ser$^2$,Leu$^5$]enkephalil-Thr;
[D-Pen$^2$,D-Pen$^5$]-enkephalin;
compounds of the formulae:

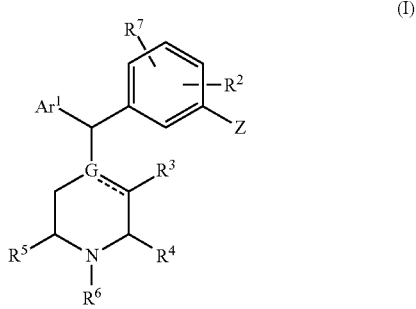

(I)

wherein:
Ar$^1$ is a 5- or 6-member carbocyclic or heterocyclic aromatic ring with atoms selected from the group consisting of carbon, nitrogen, oxygen and sulfur and may include thiophenyl, thiazolyl, furanyl, pyrrolyl, phenyl, or pyridyl, and having on a first carbon atom thereof a substituent Y and on a second ring carbon thereof a substituent R$^1$, Y is selected from the group consisting of:
hydrogen;
halogen;
$C_1$-$C_6$ alkyl, $C_2$-$C_6$ alkenyl, $C_2$-$C_6$ alkynyl;
$C_1$-$C_6$ haloalkyl;
$C_1$-$C_6$ alkoxy;
$C_3$-$C_6$ cycloalkoxy;
sulfides of the formula $SR^8$ where $R^8$ is $C_1$-$C_6$ alkyl, $C_2$-$C_6$ alkenyl, $C_2$-$C_6$ alkynyl, $C_3$-$C_6$ cycloalkyl, arylalkyl having a $C_5$-$C_{10}$ aryl moiety and an $C_1$-$C_6$ alkyl moiety, or $C_5$-$C_{10}$aryl;
sulfoxides of the formula $SOR^8$ where $R^8$ is the same as above;
sulfones of the formula $SO_2R^8$ where $R^8$ is the same as above;
nitrile;
$C_1$-$C_6$ acyl;
alkoxycarbonylamino(carbamoyl) of the formula $NHCO_2R_8$ where $R^8$ is the same as above;
carboxylic acid, or an ester, amide, or salt thereof;
aminomethyl of the formula $CH_2NR^9R^{10}$ where $R^9$ and $R^{10}$ may be the same or different, and may be hydrogen, $C_1$-$C_6$ alkyl, $C_2$-$C_6$ alkenyl, $C_2$-$C_6$ alkynyl, $C_2$-$C_6$ hydroxyalkyl, $C_2$-$C_6$ methoxyalkyl, $C_3$-$C_6$ cycloalkyl, or $C_5$-$C_{10}$ aryl, or $R^9$ and $R^{10}$ together may form a ring of 5 or 6 atoms, the ring atoms selected from the group consisting of N and C;
carboxamides of the formula $CONR^9R^{10}$ where $R^9$ and $R^{10}$ are the same as above, or $C_2$-$C_{30}$ peptide conjugates thereof; and
sulfonamides of the formula $SO_2NR^9R^{10}$ where $R^9$ and $R^{10}$ are the same as above;
Z is selected from the group consisting of:
hydrogen, hydroxy and carboxy and esters thereof;
alkoxy, carboxyalkoxy, alkoxy-carboxylic acid, hydroxymethyl, and esters thereof; and
amino, carboxamides and sulfonamides thereof;
G is carbon or nitrogen;
$R^1$ is hydrogen, halogen, or $C_1$-$C_4$ alkyl, $C_2$-$C_4$ alkenyl, $C_2$-$C_4$ alkynyl;
$R^2$ is hydrogen, halogen, or $C_1$-$C_4$ alkyl, $C_2$-$C_4$ alkenyl, $C_2$-$C_4$ alkynyl;
$R^3$, $R^4$ and $R^5$ may be the same or different, and are independently selected from hydrogen and methyl, and wherein at least one of $R^3$, $R^4$ or $R^5$ is not hydrogen, subject to the proviso that the total number of methyl groups does not exceed two, or any two of $R^3$, $R^4$ and $R^5$ together may form a bridge of 1 to 3 carbon atoms;
$R^6$ is selected from the group consisting of:
  hydrogen;
  $C_1$-$C_6$ alkyl, $C_2$-$C_6$ alkenyl, $C_2$-$C_6$ alkynyl;
  $C_3$-$C_6$ cycloalkyl;
  arylalkyl having $C_5$-$C_{10}$ aryl and $C_1$-$C_6$ alkyl moieties;
  alkoxyalkyl having $C_1$-$C_4$ alkoxy and $C_1$-$C_4$ alkyl moieties;
  $C_2$-$C_4$ cyanoalkyl;
  $C_2$-$C_4$ hydroxyalkyl;
  aminocarbonylalkyl having a $C_1$-$C_4$ alkyl moiety; and
  $R^{12}COR^{13}$, where $R^{12}$ is $C_1$-$C_4$ alkylene, and $R^{13}$ is $C_1$-$C_4$ alkyl or $C_1$-$C_4$ alkoxy or hydroxy, or $R^6$ is

and $Ar^2$ is a 5 or 6-member carbocyclic or heterocyclic aromatic ring with atoms selected from the group consisting of carbon, nitrogen, oxygen and sulfur, and having on a carbon atom thereof a substituent X,
wherein X is selected from the group consisting of a halogen (fluorine, bromine, chlorine, iodine), hydrogen, hydroxy, and esters thereof; carboxy and esters thereof; C1-C4 carboxyalkyl and esters thereof; alkoxy, alkyl carboxylic acid, carboxylic acid, hydroxymethyl, and esters thereof; and
amino, and carboxamides and sulfonamides thereof; and
$R^7$ is hydrogen or fluorine;

(II)

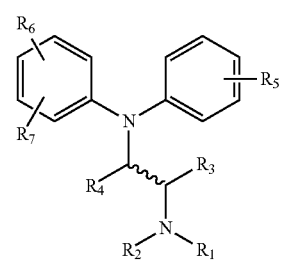

wherein
$R_1$ and $R_2$, which can be the same or different, are each hydrogen, linear or branched $C_{1-6}$ alkyl, $C_{3-7}$ cycloalkyl, $C_{3-7}$ cycloalkenyl, $C_{4-6}$ cycloalkylalkyl, $C_{3-6}$ alkenyl, $C_{3-5}$ alkynyl, aryl, aralkyl or furan-2 or 3-yl alkyl or may form together a $C_{3-7}$ alkyl ring which may be interrupted by oxygen.
$R_3$ and $R_4$, which can be the same or different, are each hydrogen, linear or branched $C_{1-6}$ alkyl, or $R_4$ is oxygen forming with the carbon atom to which is attached a C=O group;
$R_5$ is hydrogen, hydroxy, $C_{1-3}$ alkoxy, thiol or alkylthio;
$R_6$ is phenyl, halogen, $NH_2$ or a para or meta —C(Z)—$R_8$ group, in which Z is oxygen or sulphur;
$R_8$ is $C_{1-8}$-alkyl, $C_{1-8}$-alkoxy or $NR_9R_{10}$, wherein $R_9$ and $R_{10}$, which may be the same or different, are hydrogen, straight or branched $C_{1-6}$ alkyl, $C_{3-7}$ cycloalkyl, $C_{4-6}$ cycloalkylalkyl, $C_{3-6}$ alkenyl, aryl or aralkyl,
or $R_6$ is a para or meta

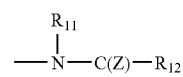

group
in which $R_{11}$ and $R_{12}$ which may the same or different are hydrogen, straight or branched $C_{1-6}$ alkyl, $C_{3-7}$ cycloalkyl, $C_{4-6}$ cycloalkylalkyl, $C_{3-6}$ alkenyl, aryl, aralkyl or an optionally substituted heterocyclic ring, and Z is as defined above; and,
$R_7$ is hydrogen, straight or branched $C_{1-8}$ alkyl or halogen;

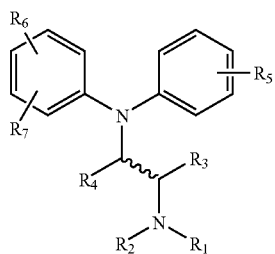

(III)

wherein,

R$_1$ and R$_2$, can be the same or different, are each hydrogen, linear or branched C$_{1-6}$ alkyl, C$_{3-7}$ cycloalkyl, C$_{3-7}$ cycloalkenyl, C$_{4-6}$ cycloalkylalkyl, C$_{3-6}$ alkenyl, C$_{3-5}$ alkynyl, aryl, aralkyl or furan-2 or 3-yl alkyl or may form together a C$_{3-7}$ alkyl ring which may be interrupted by oxygen.

R$_3$ and R$_4$, can be the same or different, are each hydrogen, linear or branched C$_{1-6}$ alkyl;

R$_5$ is hydroxy, C$_{1-6}$ alkoxy, thiol or alkylthio;

R$_6$ is a —C(Z)—R$_8$ group, wherein Z is oxygen or sulphur, R$_8$ is C$_{1-8}$-alkyl, C$_{1-8}$-alkoxy or NR$_9$R$_{10}$, wherein R$_9$ and R$_{10}$, which may be the same or different, are hydrogen, straight or branched C$_{1-6}$ alkyl, C$_{3-7}$ cycloalkyl, C$_{4-6}$ cycloalkylalkyl, C$_{3-6}$ alkenyl, aryl or aralkyl, or R$_6$ is a meta or para

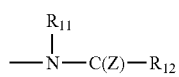

group wherein R$_{11}$ and R$_{12}$ have the same meaning as R$_9$ and R$_{10}$ or together form an optionally substituted heterocyclic ring and Z is as defined above, and R$_7$ is hydrogen, straight or branched C$_{1-8}$ alkyl or halogen; and

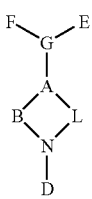

(IV)

wherein
A is N or C—X
wherein
X is H or C$_{1-4}$ alkyl;
G is C—Y
wherein
Y is H or C$_{1-4}$ alkyl;
B is an optional C$_{1-6}$ hydrocarbyl group, optionally substituted;
L is an optional C$_{1-6}$ hydrocarbyl group, optionally substituted;
and wherein A, B, and L in combination with the N constitute a first ring structure which has from 5-7 atoms in the ring;
further wherein:

either D is H or a C$_{1-10}$ hydrocarbyl group,
or D is a C$_{1-10}$ hydrocarbyl group linked to B or L to form a second ring structure which includes the N of the first ring structure, which second ring structure is fused to the first ring structure and which second ring structure has from 5-7 atoms in the ring;
E is a phenyl group substituted by at least one or more of hydroxy, C$_{1-4}$ alkoxy, or NH$_2$SO$_2$ C$_{1-4}$ alkylene;
F represents a combination of a phenyl group and a heterocyclic group, wherein
(i) the phenyl group is positioned intermediate (in between) G and the heterocyclic group;
(ii) the phenyl group is fused to the heterocyclic group or is linked directly to the heterocyclic group or is attached via a spacer group to the heterocyclic group, wherein the spacer group is any one of C$_{1-4}$ alkylene, carbonyl or SO$_2$; and
(iii) the heterocyclic group is substituted by at least one or more of: a COOH group, a bio-isostere of a COOH group, a biolabile ester derivative of a COOH group, a C$_{1-10}$ hydrocarbyl group comprising one or more COOH groups, a C$_{1-10}$ hydrocarbyl group comprising one or more bio-isosteres of a COOH group, or a C$_{1-10}$ hydrocarbyl group comprising one or more biolabile ester derivatives of a COOH group;
and pharmaceutically acceptable esters and salts of the compounds (I)-(IV).

As used herein, in reference to the present invention, the term "alkyl" is intended to be broadly construed as encompassing: (i) alkyl groups of straight-chain as well as branched chain character; (ii) unsubstituted as well as substituted alkyl groups, wherein the substituents of substituted alkyl groups may include any sterically acceptable substituents which are compatible with such alkyl groups and which do not preclude the efficacy of the diarylmethylpiperazine delta opioid receptor agonist for its intended utility (examples of substituents for substituted alkyl groups include halogen (e.g., fluoro, chloro, bromo, and iodo), amino, amido, C$_1$-C$_4$ alkyl, C$_1$-C$_4$ alkoxy, nitro, hydroxy, etc.); (iii) saturated alkyl groups as well as unsaturated alkyl groups, the latter including groups such as alkenyl-substituted alkyl groups (e.g., allyl, methallyl, propallyl, butenylmethyl, etc.), alkynyl-substituted alkyl groups, and any other alkyl groups containing sterically acceptable unsaturation which is compatible with such alkyl groups and which does not preclude the efficacy of the diarylmethylpiperazine delta opioid receptor agonist for its intended utility; and (iv) alkyl groups including linking or bridge moieties, e.g., heteroatoms such as nitrogen, oxygen, sulfur, etc.

As used herein, in reference to the present invention, the term "aryl" is intended to be broadly construed as referring to carbocyclic (e.g., phenyl, naphthyl) as well as heterocyclic aromatic groups (e.g., pyridyl, thienyl, furanyl, etc.) and encompassing unsubstituted as well as substituted aryl groups, wherein the substituents of substituted aryl groups may include any sterically acceptable substituents which are compatible with such aryl groups and which do not preclude the efficacy of the diarylmethylpiperazine delta opioid receptor agonist for its intended utility. Examples of substituents for substituted aryl groups include hydrogen, one or more of halogen (e.g., fluoro, chloro, bromo, and iodo), amino, amido, C$_1$-C$_4$ alkyl, C$_1$-C$_4$ alkoxy, nitro, trifluoromethyl, hydroxy, hydroxyalkyl containing a C$_1$-C$_4$ alkyl moiety, etc.

The active agent may be administered in the form of a pharmaceutically acceptable salt, ester, amide or prodrug or combination thereof. Salts, esters, amides and prodrugs of the active agents may be prepared using standard procedures known to those skilled in the art of synthetic organic chemistry and described, for example, by J. March, Advanced Organic Chemistry: Reactions, Mechanisms and Structure, 4th Ed. (New York: Wiley-Interscience, 1992). For example, acid addition salts are prepared from the free base (typically wherein the neutral form of the drug has a neutral —NH$_2$ group) using conventional means, involving reaction with a suitable acid. Generally, the base form of the active agent is dissolved in a polar organic solvent such as methanol or ethanol and the acid is added thereto. The resulting salt either precipitates or may be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Conversely, preparation of basic salts of acid moieties which may be present on an active agent are prepared in a similar manner using a pharmaceutically acceptable base such as sodium hydroxide, potassium hydroxide, ammonium hydroxide, calcium hydroxide, trimethylamine, or the like.

Examples of pharmaceutically acceptable salts include salts derived from an appropriate base, such as an alkali metal (for example, sodium, potassium), an alkaline earth metal (for example, calcium, magnesium), ammonium and NR'$_4^+$ (wherein R' is C$_1$-C$_4$ alkyl). Pharmaceutically acceptable salts of an amino group include salts of: organic carboxylic acids such as acetic, lactic, tartaric, malic, lactobionic, fumaric, and succinic acids; organic sulfonic acids such as methanesulfonic, ethanesulfonic, isethionic, benzenesulfonic and p-toluenesulfonic acids; and inorganic acids such as hydrochloric, hydrobromic, sulfuric, phosphoric and sulfamic acids. Pharmaceutically acceptable salts of a compound having a hydroxyl group consist of the anion of said compound in combination with a suitable cation such as Na$^+$, NH$_4^+$, or NR'$_4^+$ (wherein R' is for example a C$_{1-4}$ alkyl group).

Preparation of esters involves functionalization of hydroxyl and/or carboxyl groups that may be present within the molecular structure of the drug. The esters of hydroxyl groups are typically acyl-substituted derivatives of free alcohol groups, i.e., moieties which are derived from carboxylic acids of the formula RCOOH where R is alkyl, and preferably is lower alkyl. Esters can be reconverted to the free acids, if desired, by using conventional hydrolysis procedures. Examples of pharmaceutically acceptable esters include carboxylic acid esters of the hydroxyl group in the compounds of the present invention in which the non-carbonyl moiety of the carboxylic acid portion of the ester grouping is selected from straight or branched chain alkyl (e.g. n-propyl, t-butyl, n-butyl), alkoxyalkyl (e.g. methoxymethyl), arylalkyl (e.g. benzyl), aryloxyalky (e.g. phenoxymethyl), and aryl (e.g. phenyl); alkyl-, aryl-, or arylalkylsulfonyl (e.g. methanesulfonyl); amino acid esters (e.g. L-valyl or L-isoleucyl); dicarboxylic acid esters (e.g. hemisuccinate); carbonate esters (e.g. ethoxycarbonyl); carbamate esters (e.g. dimethylaminocarbonyl, (2-aminoethyl)aminocarbonyl); and inorganic esters (e.g. mono-, di- or triphosphate). The esters of carboxyl groups within the molecular structure of the drug are typically prepared from C$_1$-C$_4$ alcohols (e.g., ethanol, propanol) or arylalkyl alcohols (e.g., benzyl alcohols). Preparation of amides and prodrugs can be carried out in an analogous manner.

Other derivatives and analogs of the active agents may be prepared using standard techniques known to those skilled in the art of synthetic organic chemistry, or may be deduced by reference to the pertinent literature. In addition, chiral active agents may be in isomerically pure form, or they may be administered as a racemic mixture of isomers.

Pharmaceutical Formulations and Modes of Administration:

Depending on the intended mode of administration, the pharmaceutical compositions may be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions include an effective amount of the delta opioid receptor agonist in combination with a pharmaceutically acceptable carrier, if desired, and, in addition, may include other pharmaceutical agents, adjuvants, diluents, buffers, etc. The amount of active agent administered will, of course, be dependent on the subject being treated, the subject's weight, the manner of administration and the judgment of the prescribing physician.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see Remington: the Science and Practice of Pharmacy, 19$^{th}$ Ed. (Easton, Pa.: Mack Publishing Co., 1995).

For oral administration, the composition will generally take the form of a tablet or capsule, or may be an aqueous or nonaqueous solution, suspension or syrup. Tablets and capsules are preferred oral administration forms. Tablets and capsules for oral use will generally include one or more commonly used carriers such as lactose and cornstarch. Lubricating agents, such as magnesium stearate, are also typically added. When liquid suspensions are used, the active agent may be combined with emulsifying and suspending agents. If desired, flavoring, coloring and/or sweetening agents may be added as well. Other optional components for incorporation into an oral formulation herein include, but are not limited to, preservatives, suspending agents, thickening agents, and the like.

Parenteral administration, if used, is generally characterized by injection. Injectable formulations can be prepared in conventional forms, either as liquid solutions or suspensions, solid forms suitable for solubilization or suspension in liquid prior to injection, or as emulsions. Preferably, sterile injectable suspensions are formulated according to techniques known in the art using suitable carriers, dispersing or wetting agents and suspending agents. The sterile injectable formulation may also be a sterile injectable solution or a suspension in a nontoxic parenterally acceptable diluent or solvent. Among the acceptable vehicles and solvents that may be employed are water, Ringer's solution and isotonic sodium chloride solution. In addition, sterile, fixed oils, fatty esters or polyols are conventionally employed as solvents or suspending media. A more recently revised approach for parenteral administration involves use of a slow release or sustained release system, such that a constant level of dosage is maintained.

Intracavernosal injection can be carried out by use of a syringe any other suitable device. The injection is made on the dorsum of the penis by placement of the needle to the side of each dorsal vein and inserting it deep into the corpora.

The active agent can be administered in a pharmaceutical formulation suitable for transurethral drug delivery. The formulation contains one or more selected carriers or excipients, such as water, silicone, waxes, petroleum jelly, polyethylene glycol ("PEG"), propylene glycol ("PG"), liposomes, sugars such as mannitol and lactose, and/or a variety of other materials, with polyethylene glycol and derivatives thereof particularly preferred.

Depending on the delta opioid receptor agonist administered, it may be desirable to incorporate a transurethral permeation enhancer in the urethral dosage form. Examples of suitable transurethral permeation enhancers include dimethylsulfoxide ("DMSO"), dimethyl formamide ("DMF"), N,N-dimethylacetamide ("DMA"), decylmethylsulfoxide ("$C_{10}$ MSO"), polyethylene glycol monolaurate ("PEGML"), glycerol monolaurate, lecithin, the 1-substituted azacycloheptan-2-ones, particularly 1-n-dodecylcyclazacycloheptan-2-one (available under the trademark Azone® from Nelson Research & Development Co., Irvine, Calif.), SEPA® (available from Macrochem Co., Lexington, Mass.), alcohols (e.g., ethanol), detergents (such as Tergitol®, Nonoxynol-9® and TWEEN-80®) and the like.

Transurethral formulations may additionally include one or more enzyme inhibitors effective to inhibit drug-degrading enzymes that may be present in the urethra. Such enzyme inhibiting compounds may be determined by those skilled in the art by reference to the pertinent literature and/or using routine experimental methods. Additional optional components include excipients, preservatives (e.g., antioxidants), chelating agents, solubilizing agents (e.g., surfactants), and the like, as will be appreciated by those skilled in the art of drug formulation preparation and delivery.

Transurethral drug administration can be carried out in a number of different ways using a variety of urethral dosage forms. For example, the composition can be introduced into the urethra from a flexible tube, squeeze bottle, pump or aerosol spray. The active agents may also be contained in coatings, pellets or suppositories that are absorbed, melted or bioeroded in the urethra. Urethral suppository formulations containing PEG or a PEG derivative amay be used and may be formulated using conventional techniques, e.g., compression molding heat molding or the like, as will be appreciated by those skilled in the art and as described in the pertinent literature and pharmaceutical texts. See, for example, Remington, referenced above. The PEG or PEG derivative preferably has a molecular weight $M_w$ in the range of about 200 to 2500. Suitable polyethylene glycol derivatives include polyethylene glycol fatty acid esters, for example, polyethylene glycol monostearate, polyethylene glycol sorbitan esters, e.g., polysorbates, and the like. It is also preferred that urethral suppositories contain one or more solubilizing agents effective to increase the solubility of the active agent in the PEG or other transurethral vehicle. The solubilizing agent may be a nonionic, anionic, cationic or amphoteric surfactant.

It may be desirable to deliver the active agent in a urethral dosage form, which provides for controlled or sustained release of the active agent. In such a case, the dosage form typically comprises a biocompatible, biodegradable material, typically a biodegradable polymer. Examples of such polymers include polyester, polyalkylcyanoacrylate, polyorthoester, polyanhydride, albumin, gelatin and starch. These and other polymers can be used to provide biodegradable microparticles that enable controlled and sustained drug release, which in turn will minimize the required dosing frequency.

The compounds of the invention may also be delivered through the skin or muscosal tissue using conventional transdermal drug delivery systems, i.e., transdermal "patches" wherein the agent is typically contained within a laminated structure that serves as a drug delivery device to be affixed to the body surface. In such a structure, the pharmaceutical composition is typically contained in a layer, or "reservoir," underlying an upper backing layer. The laminated device may contain a single reservoir, or it may contain multiple reservoirs. In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the active agent-containing reservoir and skin contact adhesive are present as separate and distinct layers, with the adhesive underlying the reservoir which, in this case, may be either a polymeric matrix as described above, or it may be a liquid or gel reservoir, or may take some other form. The backing layer in these laminates, which serves as the upper surface of the device, functions as the primary structural element of the laminated structure and provides the device with much of its flexibility. The material selected for the backing layer should be substantially impermeable to the active agent and any other materials that are present.

Alternatively, the pharmaceutical compositions of the invention may be administered in the form of suppositories for rectal administration. These can be prepared by mixing the agent with a suitable nonirritating excipient which is solid at room temperature but liquid at the rectal temperature and therefore will melt in the rectum to release the drug. Such materials include cocoa butter, beeswax and polyethylene glycols. The suppository will preferably, although not necessarily, be on the order of 2 to 20 mm, preferably 5 to 10 mm in length and less than about 5 mm, preferably less than about 2 mm in width. The weight of the suppository form will typically be in the range of approximately 1 mg to 50 mg. However, it will be appreciated by those skilled in the art that the size of the suppository can and will vary, depending on the potency of the active agent, the nature of the composition, and other factors.

The pharmaceutical compositions of the invention may also be administered by nasal aerosol or inhalation. Nasal spray formulations comprise purified aqueous solutions of the active compounds with preservative agents and isotonic agents. Such formulations are preferably adjusted to a pH and isotonic state compatible with the nasal mucous membranes. Such compositions are prepared according to techniques well-known in the art of pharmaceutical formulation and may be prepared as solutions in saline, employing benzyl alcohol or other suitable preservatives, absorption promoters to enhance bioavailability, propellants such as fluorocarbons or nitrogen, and/or other conventional solubilizing or dispersing agents.

The delta opioid receptor agonists of the present invention may be included in formulations for topical drug delivery, such as in ointments and creams. Ointments are semisolid preparations that are typically based on petrolatum or other petroleum derivatives. Creams containing the selected active agent, are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum delivery of the active agent. As with other carriers or vehicles, an ointment base should be inert, stable, nonirritating and non-sensitizing.

In some applications, it may be advantageous to utilize the active agent in a "vectorized" form, such as by encapsulation of the active agent in a liposome or other encapsulant medium, or by fixation of the active agent, e.g., by covalent bonding, chelation, or associative coordination, on a suitable biomolecule, such as those selected from proteins, lipoproteins, glycoproteins, and polysaccharides.

Ophthalmic formulations are prepared by a similar method to the nasal spray, except that the pH and isotonic factors are preferably adjusted to match that of the eye.

The pharmaceutical formulations discussed above may further contain one or more pharmacologically active agents in addition to the delta opioid receptor agonists, such as vasodilators.

The compounds contemplated by the invention include those set forth above, as well as physiologically functional derivatives thereof. By "physiologically functional derivative" is meant a pharmaceutically acceptable salt, ether, ester or salt of an ether or ester of the compounds set forth above or any other compound which, upon administration to the recipient, is capable of providing (directly or indirectly) the said compound or an active metabolite or residue thereof.

The amount of delta opioid receptor agonist administered, and the dosing regimen used, will, of course, be dependent on the particular delta opioid receptor agonist selected, the age and general condition of the subject being treated, the severity of the subject's condition, and the judgment of the prescribing physician. Generally, the daily dosage when administered locally will be less than the dosage normally given in conjunction with systemic modes of administration, and typically, the delta agonist will be administered one to four times daily or, with some active agents, just prior to intercourse. Alternatively, a large initial loading dose can be used to achieve effective levels of the active agent and can be followed by smaller doses to maintain those levels. A typical daily dose of an active agent as administered locally is generally in the range of approximately 0.1 to 100 mg/kg body weight of the recipient. Depending on the half-life of the delta opioid receptor agonist and the availability via the chosen route of administration, the dosing regimen can be modulated in order to achieve satisfactory control of the onset of ejaculation.

In general, while the effective dosage of compounds of the invention for therapeutic use may be widely varied in the broad practice of the invention, depending on the specific condition involved, as readily determinable within the skill of the art, suitable therapeutic doses of the compounds of the invention, for each of the appertaining compositions described herein, and for achievement of therapeutic benefit in treatment of each of the conditions described herein, will preferably be in the range of 10 micrograms (µg) to 500 milligrams (mg) per kilogram body weight of the recipient per day, more preferably in the range of 50 µg to 75 mg per kilogram body weight per day, and most preferably in the range of 1 mg to 50 mg per kilogram body weight per day. The desired dose is may be presented as two, three, four, five, six, or more sub-doses administered at appropriate intervals throughout the day.

The mode of administration and dosage forms will of course affect the therapeutic amounts of the compounds which are desirable and efficacious for the given treatment application. For example, orally administered dosages typically are at least twice, e.g., 2-10 times, the dosage levels used in parenteral administration methods, for the same active ingredient. In oral administration, dosage levels for compounds of the present invention may be on the order of 5-200 mg/70 kg body weight/day. In tablet dosage forms, typical active agent dose levels are on the order of 10-100 mg per tablet.

Kits

The invention also encompasses a kit for patients to carry out the present method of treating premature ejaculation. The kit contains the pharmaceutical composition to be administered, a device for administering the pharmaceutical composition (e.g., a transurethral drug delivery device such as a syringe, a transdermal patch), a container, preferably sealed, for housing the active agent and delivery device during storage and prior to use, and instructions for carrying out drug administration in an effective manner. The formulation may consist of the delta opioid receptor agonist in unit dosage form. The kit may contain multiple formulations of different dosages of the same agent. The instructions may be in written or pictograph form, or can be on recorded media including audio tape, video tape, or the like.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

The following examples are illustrative of synthetic procedures that may be advantageously utilized to make compounds of the present invention.

Melting points were determined with a Thomas-Hoover apparatus and are uncorrected. All chemical reagents were purchased from Aldrich Chemical Company, Milwaukee, Wis., unless otherwise specified. Commercial solvents were used without further purification. NMR spectra were obtained on a variety of instruments ranging from 200 to 600 MHz in field strength. HPLC analyses were performed with a Waters liquid chromatography system equipped with a 700 Satellite WISP, 600E System Controller and a 991 Photodiode Array. Analytical gas chromatography was performed on a Hewlett-Packard Series II instrument, Model 5890 with flame ionization detector using helium as the carrier gas (injector temperature, 225° C.; detector temperature, 250° C.). Mass spectra were performed by various contractual sources using chemical ionization (CI), electrospray (ES), or fast-atom bombardment (FAB) instrumentation. Optical rotations were obtained with a Perkin-Elmer 241 polarimeter. Analytical thin layer chromatography was performed on E. Merck glass plates pre-coated with silica gel GF (250 microns). Elemental analyses were performed by Atlantic Microlab, Norcross, Ga.

EXAMPLE 1

4-((alpha-S)-alpha-((2S,5R)-4-Allyl-2,5-dimethyl-1-piperazinyl)benzyl)-N,N-diethylbenzamide 4-Carboxybenzaldehyde (150 g, 100 mmol) was added to a 250 mL, 3-necked round bottom flask and stirred under nitrogen in 110 mL of toluene. Thionyl chloride (8.75 mL, 120 mmol) was added to the mixture, followed by the addition of 6 drops of DMF. A reflux condenser fitted with a calcium chloride drying tube was placed on the flask. The reaction was placed in an oil bath and heated at a bath temperature maintained below 120° C. The mixture was allowed to reflux for 1 hour after a clear solution was obtained and then cooled to room temperature. The solution was diluted with anhydrous toluene, and all volatiles were removed under vacuum.

The crude acid chloride was dissolved in 200 mL of dry tetrahydrofuran and cooled in an ice/water bath. Diethylamine (31.35 mL, 300 mmol) in 70 mL of dry tetrahydrofuran was added dropwise via an addition funnel. The cloudy solution was allowed to warm to room temperature over 1 hour and stirred overnight. Water was added and the product was extracted with dichloromethane. The organic layer was washed with water and saturated sodium chloride solution, dried over sodium sulfate, and the solvent was removed under vacuum. 3-Formyl-N,N-diethylbenzamide (17.72 g) was obtained as a light golden oil (86% unchromatographed yield). $^1$H NMR (300 MHz, DMSO-$d_6$): δ 1.04-1.18 (m, 6H); 3.17-3.45 (m, 4H); 7.65-7.66 (m, 2H); 7.85 (s, 1H); 7.93-7.94 (m, 1H); 10.03 (s, 1H).

A 12 L, 3-necked round bottom flask was charged with trans-2,5-dimethylpiperazine (767 g, 6.72 mol), which had been recrystallized from toluene to mp=115-119° C., and 600 mL of water. The flask was cooled in an ice bath and a solution of methanesulfonic acid (1290 g, 13.4 mol) in 600 mL of water was added slowly with stirring and cooling to maintain the temperature below 40° C. The solution was cooled to 20° C. and 800 mL of ethanol was added. A 500 mL addition funnel was filled with 60% aqueous potassium acetate from a 2 L reservoir of the solution, and potassium acetate was added to the reaction flask to adjust the pH to 4.0. A second addition funnel was charged with a solution of ethyl chloroformate (642 mL, 6.71 mol) in 360 mL of tetrahydrofuran. The ethyl chloroformate and potassium acetate solutions were simultaneously added dropwise with adjustment of rate to maintain the reaction solution at pH 4.0±0.1, with cooling as necessary to maintain temperature at 25° C. After addition of the ethyl chloroformate was complete, the reaction was stirred for 1 hour with continued addition of potassium acetate solution to maintain a pH of 4.0. The organic solvents were removed by distillation under vacuum. The remaining aqueous solution was washed with 1500 mL of ethyl acetate to remove any bis-carbamate impurity. The ethyl acetate wash was extracted with two 500 mL portions of 1M hydrochloric acid to recover desired product. The acid extracts were combined with the original aqueous solution and the pH was adjusted to 11 by addition of 10M sodium hydroxide, with cooling to maintain temperature below 40 C. The aqueous solution was extracted with two 1500 mL portions of ethyl acetate, the combined extracts were dried over magnesium sulfate, and the solvent was removed to give 927 g (74%) ethyl trans-2,5-dimethyl-1-piperazinecarboxylate as a yellow oil.

A mixture of ethyl trans-2,5-dimethyl-1-piperazinecarboxylate (643 g, 3.45 mol), allyl bromide (328 mL, 3.80 mol), and sodium carbonate (440 g, 4.15 mol) in 2500 mL of acetonitrile was heated at reflux for 1.5 hours. The reaction was cooled to room temperature, filtered, and the solvent removed under vacuum. The residue was dissolved in 4000 mL of dichloromethane and washed with two 500 mL portions of 1 M sodium hydroxide. The dichloromethane solution was dried over magnesium sulfate and the solvent was removed to give 630 g (81%) of ethyl trans-4-allyl-2,5-dimethyl-1-piperazinecarboxylate as an oil.

Ethyl trans-4-allyl-2,5-dimethyl-1-piperazinecarboxylate (630 g, 2.78 mol) was added to a solution of 87% potassium hydroxide pellets (2970 g, 46 mol) in 4300 mL of 95% ethanol and heated at reflux for 1.5 hours. Carbon dioxide evolution was observed for the first 0.5-1 hour of heating. The reaction was cooled below reflux temperature and 2000 mL of toluene was carefully added. Ethanol was removed by azeotropic distillation at 105° C., while adding an additional 4000 mL of toluene to the reaction flask during the course of the distillation. After collection of 9000 mL of distillate, the reaction was cooled to 100° C. and 1000 mL of toluene was carefully added. The solution was slowly cooled to 5° C. and maintained at 5 C for 30 minutes. The solution was filtered, and the filter cake was washed with an additional 1500 mL of toluene. The filtrate was washed with 1000 mL of water, dried over magnesium sulfate, and the solvent was removed to give 296 g (69%) of trans-1-allyl-2,5-dimethylpiperazine as a dark liquid. NMR (300 MHz, DMSO-$d_6$): δ 0.87 (d, J=6.3 Hz, 3H); 0.92 (d, J=6.3 Hz, 3H); 1.63 (t, J=11 Hz, 1H); 2.05 (m, 1H); 2.30 (t, J=11 Hz, 1H); 2.6-2.8 (m, 4H); 3.33 (dd, $J_1$=5 Hz, $J_2$=14 Hz, 1H); 5.09 (d, J=8.7 Hz, 1H); 5.13 (d, J=14 Hz, 1H) 5.8 (m, 1H).

Di-p-toluoyl-D-tartaric acid (Schweizerhall, Inc., South Plainfield, N.J.) (1.25 Kg, 3.2 mol) was dissolved in hot (~60 C) 95% ethanol (16 L) and racemic trans-1-allyl-2,5-dimethylpiperazine (500 g, 3.2 mol) was added in several portions (caution: exothermic). The hot solution was seeded with crystals of the diastereoisomerically pure salt (obtained from a previous small-scale resolution) and cooled to room temperature over 2-3 hours. The solution was slowly stirred for 2 days at room temperature. The resulting salt was collected by filtration, washed twice with 95% ethanol, and dried under vacuum to give 826.5 g of a white solid (47%). The process was repeated with a second batch of the di-p-toluoyl-D-tartaric acid and racemic trans-1-allyl-2,5-dimethylpiperazine to give 869 g (50%).

The total of 1695 g of salt was divided into three batches and each batch was recrystallized twice in the following fashion. The salt was dissolved in refluxing 95% ethanol (~2.7 L/100 g of salt), and approximately half of the ethanol was removed by distillation. (Note: vigorous stirring was necessary during distillation to prevent crystallization on the vessel wall.) The hot solution was seeded with crystals of the pure diastereomeric salt, cooled to room temperature, and stirred slowly for 2 days before collecting the salt by filtration. (Note: a subsequent experiment suggested that crystallization time can be reduced from 2 days to 8 hours.) The total amount recovered was 1151 g. The salt was dissolved in 3 L of 2 M aqueous sodium hydroxide, and the aqueous solution was extracted with four 1 L portions of dichloromethane. The organic extracts were combined, dried over sodium sulfate, and solvent removed by rotary evaporation (temperature <20° C.) to give 293 g (29% based on racemic weight) of (2R,5S)-1-allyl-2,5-dimethylpiperazine as a clear oil. $[\alpha]_D^{20}$=−55.1 (abs. ethanol, c=1.2). The trifluoroacetamide of the product was prepared with trifluoroacetic anhydride and analyzed by chiral capillary gas chromatography (Chiraldex B-PH column, 20 m×0.32 mm, Advanced Separation Technologies Inc., Whippany, N.J., 120° C.) indicating an enantiopurity of >99% ee (retention time of desired enantiomer, 11.7 min; other enantiomer, 10.7 min).

A solution of 4-formyl-N,N-diethylbenzamide (4.105 g, 20 mmol), benzotriazole (2.38 g, 20 mmol) and (2R,5S)-1-allyl-2,5-dimethylpiperazine (3.085 g, 20 mmol) in toluene (200 mL) was heated under reflux with azeotropic removal of water for 2.5 h. The volume of the reaction mixture was reduced to approximately 75 mL by distillation. Anhydrous tetrahydrofuran (50 mL) was added to the solution under nitrogen, and the reaction was stirred during the addition of phenylmagnesium bromide (1.0 M in tetrahydrofuran, 40 mL, 40 mmol). The reddish brown suspension was stirred at ambient temperature for 1 h and quenched with saturated aqueous ammonium chloride solution (10 mL). The yellow suspension was stirred for 15 min, and anhydrous magnesium sulfate (10 g) added. The suspension was stirred for a further 15 min and filtered. The filter cake was washed with tetrahydrofuran, and the combined filtrate and washings were evaporated to a thick oil. The residue was partitioned between ethyl acetate (400 mL) and aqueous sodium hydroxide solution (1.0 M, 100 mL). The organic layer was separated and washed successively with 1M-NaOH (3×100 mL), water (100 mL) and saturated aqueous sodium chloride solution (100 mL). The ethyl acetate solution was extracted with 1.0 M HCl (2×25 mL), and the combined acid extracts were basified to pH 10 with 10 M aqueous NaOH. The oily aqueous suspension was extracted with methylene chloride (2×25 mL) and the organic layer dried over anhydrous magnesium sulfate. The methylene chloride solution was evaporated to dryness, and the semi-crystalline residue crystallized from ethyl acetate to yield the title compound (1.84 g, 21.9%). Calc. for $C_{27}H_{37}N_3O$ 0.15 $H_2O$ C, 76.79; H, 8.90; N, 9.95. Found C, 76.79; H, 8.85; N, 9.87%. $^1$H NMR (($CD_3$)$_2$SO, 500 MHz); δ 0.94 (d, J=6.2 Hz, 3H); 1.09 (d, J=6.2 Hz, 3H, partially obscured by br m, 6H); 1.80 (m, 1H); 2.09 (dd, J=11, 7 Hz, 1H); 2.50 (br m, 1H, partially obscured by DMSO); 2.72 (dd, J=11, 2.8 Hz, 1H); 2.84 (dd, J=14, 7 Hz, 1H); 3.16 (dd, J=14, 5.2 Hz, 1H); 3.28 (br m, 3H); 5.10 (s, 1H), overlapped by 5.09 (d, J=10.6 Hz, 1H); 5.16 (dd, J=17, 1.4 Hz, 1H); 5.79 (m, 1H); 7.28 (m, 5H); 7.38 (m, 2H); 7.42 (d, J=8 Hz, 2H).

EXAMPLE 2

4-((alpha-S)-alpha-((2S,5R)-2,5-Dimethyl-1-piperazinyl)benzyl)-N,N-diethylbenzamide The compound of Example 1 was de-allylated by the method of Genet [J. P. Genet, S. Lemaire-Audoire, M. Savignac, Tetrahedron Letters, 36, 1267-1270 (1995)] as follows. A solution of 4-((alpha-S)-alpha-((2S,5R)-4-allyl-2,5-dimethyl-1-piperazinyl)benzyl)-N,N-diethylbenzamide (Example 1, 8.392 g, 20 mmol) and thiosalicylic acid (3.70 g, 24 mmol) in anhydrous tetrahydrofuran (50 mL) was stirred under nitrogen for 3 h at room temperature with a catalyst solution prepared by dissolution of bis(dibenzylidineacetone)palladium (575 mg, 1.0 mmol) and 1,4-bis(diphenylphosphino)butane (426 mg, 1.0 mmol) in tetrahydrofuran (10 mL). The reaction mixture was evaporated to dryness, the residue dissolved in a mixture of ethyl acetate/ether (1:3, 300 mL) and extracted with 5% sodium carbonate solution (2×300 mL). The organic layer was diluted with two volumes of pentane and extracted with 3M-hydrochloric acid (6×50 mL). The aqueous solution was filtered to remove suspended solid and the pH adjusted to 12 with 5-M NaOH. The resulting oily suspension was extracted with methylene chloride (2×125 mL) and the combined organic extracts dried over anhydrous sodium sulfate and evaporated to dryness. The residue was crystallized from ethyl acetate to yield fine white needles of 4-((alpha-S)-alpha-((2S,5R)-2,5-dimethyl-1-piperazinyl)benzyl)-N,N-diethylbenzamide (3.46 g). The product showed a single spot on thin layer chromatography (silica gel, EM60F$_{264}$, 4% NH$_4$OH/10% EtOH in ethyl acetate, R$_f$=0.47). $^1$H NMR (CDCl$_3$, 600 MHz); δ 0.93 (d, J=6.3 Hz, 3H); 1.12 (br m, 3H); 1.20 (d, J=6.1 Hz, 3H); 1.24 (br m, 3H); 1.55 (dd, J=9.7, 11.3 Hz, 1H, partially obscured by br m, 2H); 2.33 (m, 1H); 2.68 (m, 2H); 2.89 (m, 1H); 2.92 (dd, J=12.1, 3.1 Hz, 1H); 3.29 (br m, 2H); 3.54 (br m, 2H); 5.38 (s, 1H); 7.14 (m, 2H); 7.30 (m, 3H); 7.35 (m, 2H); 7.46 (d, J=7.8 Hz, 2H).

EXAMPLE 3

4-((alpha-S)-alpha-((2S,5R)-2,5-Dimethyl-4-(3-fluorobenzyl)-1-piperazinyl)benzyl)-N,N-diethylbenzamide A solution of 4-((alpha-S)-alpha-((2S,5R)-2,5-dimethyl-1-piperazinyl)benzyl)-N,N-diethylbenzamide (1.898 g, 5.0 mmol) in 25 mL acetonitrile was added to sodium iodide (75 mg, 0.5 mmol) and stirred during the addition of triethylamine (2.5 mL, 1.815 g, 17.94 mmol), followed by 3-fluorobenzyl bromide (1.227 mL, 1.89 g, 10.0 mmol). An immediate turbidity was observed on addition of the 3-fluorobenzyl bromide, thickening to a copious white precipitate over one hour. The flask was sealed under nitrogen and the suspension stirred overnight at room temperature. The reaction mixture was evaporated to dryness and and the residue was partitioned between ethyl acetate (40 mL) and saturated sodium bicarbonate solution (10 mL). The supernatant organic layer was separated and the aqueous layer extracted further with ethyl acetate (2×40 mL). The combined organic extracts were dried over anhydrous sodium sulfate and evaporated to a pale yellow solid which was dissolved in ethyl acetate (~7.5 mL) and applied to an intermediate (4×15 cm) Biotage silica column. Elution with ethyl acetate gave fractions containing the product, as evidenced by t.l.c. (silica, EM60F$_{254}$, 100% EtOAc, Rf=0.78) were evaporated to dryness and dried at room temperature and 2 mm Hg to yield the title compound as white crystals (2.372 g, 97.3%). Calc. for $C_{31}H_{38}FN_3O$: C, 76.35; H, 7.85; N, 8.62; F, 3.90. Found C, 76.32; H, 7.89; N, 8.51; F, 3.90%. $^1$H NMR (CDCl3, 300 MHz); δ 1.06 (d, J=6.1 Hz, 3H); 1.15 (d, J=6.1 Hz, 3H, partially overlapped by br m, 3H); 1.22 (br m, 3H); 1.94 (dd, J=10.8, 8.1 Hz, 1H); 2.02 (dd, J=10.7, 8.2 Hz, 1H); 2.57 (br m, 2H); 2.67 (m, 2H); 3.18 (d, J=13.8 Hz, 1H); 3.28 (br m, 2H); 3.53 (br m, 2H); 3.87 (d, J=13.5 Hz, 1H); 5.15 (s, 1H); 6.90 (br t, J=8.2 Hz, 1H); 7.04 (m, 2H); 7.21 (m, 3H); 7.30 (m, 5H); 7.46 (d, J=8.0 Hz, 2H).

Also prepared from 4-((alpha-S)-alpha-((2S,5R)-2,5-dimethyl-1-piperazinyl)benzyl)-N,N-diethylbenzamide (Example 2) by an essentially similar procedure to Example 3 were:

EXAMPLE 4

4-((alpha-S)-alpha-((2S,5R)-4-Benzyl-2,5-dimethyl-1-piperazinyl)benzyl)-N,N-diethylbenzamide (71.8%). Calc. for $C_{31}H_{39}N_3O$: C, 79.28; H, 8.37; N, 8.95. Found C, 79.05; H, 8.34; N, 8.91%. $^1$H NMR (CDCl3, 500 MHz); δ 1.09 (d, J=6.2 Hz, 3H); 1.12 (d, J=6.1 Hz, 3H); both doublets partially overlapped by br m, 3H); 1.24 (br m, 3H); 1.72 (m, 1H); 1.93 (m, 1H); 2.02 (dd, J=9.3, 8.4 Hz, 1H); 2.55 (m, 2H); 2.66 (dd, J=11.1, 2.4 Hz, 1H); 2.70 (dd, J=11, 2.5 Hz, 1H); 3.18 (d, J=13.8 Hz, 1H); 3.28 (br m, 2H); 3.55 (br m, 2H); 3.92 (d, J=13.1 Hz, 1H); 5.18 (s, 1H); 7.20 (d, J=7.4 Hz, 2H, partially overlapped by m, 1H); 7.30 (m, 9H); 7.47 (d, J=8 Hz, 2H).

EXAMPLE 5

4-((alpha-S)-alpha-((2S,5R)-2,5-Dimethyl-4-(2-fluorobenzyl)-1-piperazinyl)benzyl)-N,N-diethylbenzamide (68.9%). Calc. for $C_{31}H_{38}FN_3O$: C, 76.35; H, 7.85; N, 8.62; F, 3.90. Found C, 76.35; H, 8.02; N, 8.60; F, 3.81%. $^1$H NMR (CDCl3, 600 MHz); δ 1.09 (d, J=6.1 Hz, 3H); 1.13 (d, J=6.1 Hz, 3H); (both doublets overlapped by br m, 3H); 1.24 (br m, 3H); 1.90 (br t, J=10.4 Hz, 1H); 2.08 (dd, J=10.9, 8.6 Hz, 1H); 2.56 (br m, 2H); 2.66 (dd, J=11.5, 2.7 Hz, 1H); 2.73 (dd, J=11.1, 2.4 Hz, 1H); 3.28 (br m, 2H); 3.34 (d, J=13.8 Hz, 1H); 3.54 (br m, 2H); 3.88 (d, J=13.8 Hz, 1H); 5.19 (s, 1H); 7.00 (br t, J=9.1 Hz, 1H); 7.07 (t, J=7.5 Hz, 1H); 7.19 (m, 3H); 7.29 (m, 5H); 7.37 (br t, J=7.1 Hz, 1H); 7.46 (d, J=8.12H).

EXAMPLE 6

4-((alpha-S)-alpha-((2S,5R)-2,5-Dimethyl-4-(4-pyridylmethyl)-1-piperazinyl)benzyl)-N,N-diethylbenzamide (69.7%). Calc. for $C_{30}H_{38}N_4O$ 0.15 $H_2O$: C, 76.12; H, 8.16; N, 11.84. Found C, 76.14; H, 8.36; N, 11.70%. $^1$H NMR (CDCl3, 600 MHz); δ 1.05 (d, J=6.1 Hz, 3H); 1.11 (d, J=6.2 Hz, 3H; overlapped by br m, 3H); 1.24 (br m, 3H); 1.96 (br t, J=10.0 Hz, 1H); 2.08 (dd, J=7.8, 4.1 Hz, 1H); 2.59 (br d, J=4.9 Hz, 2H); 2.68 (m, 2H); 3.21 (d, J=14.0 Hz, 1H); 3.27 (br m, 2H); 3.54 (br m, 2H); 3.86 (d, J=14.2 Hz, 1H); 5.13 (s, 1H); 7.23 (d, J=7.4 Hz, 2H); 7.24 (d, J=5.6 Hz, 2H); 7.29 (d, J=8.2 Hz, 2H, partially obscuring doublet, 1H); 7.34 (br t, J=7.4 Hz, 2H); 7.46 (d, J=8.12H); 8.49 (d, J=5.9 Hz, 2H).

EXAMPLE 7

4-((alpha-S)-alpha-((2S,5R)-4-(3-Chlorobenzyl)-2,5-dimethyl-1-piperazinyl)benzyl)-N,N-diethylbenzamide (75.8%). Calc. for $C_{31}H_{38}ClN_3O$: C, 73.86; H, 7.60; N, 8.34; Cl, 7.03. Found C, 73.86; H, 7.68; N, 8.37; Cl, 7.01%. $^1$H NMR (CDCl3, 600 MHz); δ 1.06 (d, J=6.2 Hz, 3H); 1.12 (d, J=6.1 Hz, 3H, overlapping br m, 3H); 1.23 (br m, 3H); 1.94 (br t, J=9.5 Hz, 1H); 2.01 (dd, J=11.1, 8.2 Hz, 1H); 2.56 (m, 2H); 2.67 (dt, J=10.5, 2.4 Hz, 2H); 3.15 (d, J=13.5 Hz, 1H); 3.28 (br m, 2H); 3.54 (br m, 2H); 3.86 (d, J=13.5 Hz, 1H); 5.15 (s, 1H); 7.19 (m, 5H); 7.29 (m, 4H); 7.33 (br t, J=7.4 Hz, 2H); 7.46 (d, J=8.1 Hz, 2H).

EXAMPLE 8

4-((alpha-S)-alpha-((2S,5R)-2,5-Dimethyl-4-(4-methoxybenzyl)-1-piperazinyl)benzyl)-N,N-diethylbenzamide (72.44%). Calc. for $C_{32}H_{41}N_3O_2$: C, 76.92; H, 8.27; N, 8.41. Found C, 76.98; H, 8.38; N, 8.42%. $^1$H NMR (CDCl3, 600 MHz); δ 1.07 (d, J=6.2 Hz, 3H); 1.11 (d, J=6.1 Hz, 3H, overlapping br m, 3H); 1.23 (br m, 3H); 1.91 (br t, J=10.2 Hz, 1H); 1.99 (dd, J=11.0, 8.6 Hz, 1H); 2.52 (br m, 2H); 2.64 (dd, J=11.5, 2.6 Hz, 1H); 2.68 (dd, J=11.1, 2.6 Hz, 1H); 3.13 (d, J=12.9 Hz, 1H); 3.28 (br m, 2H); 3.54 (br m, 2H); 3.79 (s, 3H); 3.85 (d, J=13.5 Hz, 1H); 5.17 (s, 1H); 6.82 (d, J=8.5 Hz, 2H); 7.19 (d, J=8.3 Hz, 4H); 7.29 (m, 5H); 7.46 (d, J=8.1 Hz, 2H).

EXAMPLE 9

4-((alpha-R)-alpha-((2S,5R)-4-Allyl-2,5-dimethyl-1-piperazinyl)-3-trifluoromethyl sulfonyloxybenzyl)-N,N-diethylbenzamide A solution of 3-bromophenol (400 g, 2.31 mol), tert-butylchlorodimethylsilane (391 g, 2.54 mol), and imidazole (346 g, 5.08 mol) in 5000 mL of dichloromethane was stirred overnight at room temperature. The reaction solution was poured into 2000 mL of water and the layers were separated. The organic layer was washed with 1N aqueous sodium hydroxide solution (3×1500 mL) and water (2×1500 mL) before passing through a pad of silica gel (400 g, silica 60, 230-400 mesh). The silica gel was washed with dichloromethane (2×500 mL), the filtrates were combined and the solvent removed under reduced pressure to give 669 g (98.4%) of 3-(bromophenoxy)-tert-butyldimethylsilane as a clear pale yellow liquid. NMR (300 MHz, CDCl$_3$): δ 0.2 (s, 6H); 1.0 (s, 9H); 6.75 (m, 1H); 7.0 (br s, 1H); 7.1 (m, 2H).

3-tert-Butyldimethylsilyloxyphenylmagnesium bromide was formed by the slow addition of a mixture 3-bromophenoxy-tert-butyldimethylsilane (27.3 g, 92.6 mmol) and dibromoethane (3.45 g, 18.4 mmol) in 100 mL of inhibitor-free anhydrous tetrahydrofuran to a solution of magnesium turnings (3.57 g, 147 mmol) in 200 mL of inhibitor-free anhydrous tetrahydrofuran at reflux. After stirring for one hour at reflux the light brown clear mixture was cooled to room temperature.

4-Carboxybenzaldehyde (100.3 g, 0.67 mol) was dissolved/suspended in toluene (1200 mL, dimethylformamide (0.15 mL) added and the suspension stirred during the dropwise addition of thionyl chloride (53.5 mL, 87.2 g, 0.73 mol). The reaction mixture was heated to reflux under nitrogen and stirred for 2 h, during which time much, but not all of the aldehydo-acid passed into solution. A further quantity of thionyl chloride (20 mL, 32.6 g, 0.27 mol) was added and reflux continued overnight. The clear reaction mixture was evaporated, and the residue dissolved in anhydrous tetrahydrofuran (1500 mL). The solution was cooled in an ice/water bath and diethylamine (173 mL, 122 g, 1.67 mol (2.5 equivalents)) was added dropwise to the stirred solution. The ice-bath was removed and stirring continued for 2.5 h. The reaction mixture was filtered to remove the white crystalline diethylamine hydrochloride by-product. The crystals were washed with ethyl acetate (2×600 mL), and the washings set aside. The tetrahydrofuran filtrate was evaporated, and the residue dissolved in the ethyl acetate washings. The solution was washed sequentially with 1 M-hydrochloric acid (2×600 mL), water 2×300 mL), dilute sodium carbonate solution (saturated: H$_2$O, 1:1, 2×600 mL), water (2×300 mL) and saturated sodium chloride solution (300 mL). The organic layer was separated, dried over anhydrous sodium sulfate and evaporated to yield 4-formyl-N,N-diethylbenzamide as a pale brown oil which was used without further purification. (Yield 115.7 g, 84%)

In a 1000 mL round bottom flask fitted with a condenser and Dean-Stark trap were combined 4-formyl-N,N-diethylbenzamide (9.50 g, 46.3 mmol), benzotriazole (5.51 g, 46.3 mmol), and (2R,5S)-1-allyl-2,5-dimethylpiperazine (7.15 g, 46.3 mmol, Chirotech Technology, Ltd., Cambridge, England) with 400 mL of toluene. The reaction was heated to reflux under nitrogen until no additional water was observed in the trap (ca. 2 hours). The reaction was cooled to room temperature and concentrated under vacuum to leave a volume of approximately 50 mL. Anhydrous tetrahydrofuran (100 mL) was added to the flask under nitrogen with stirring to dissolve all residue. The solution of benzotriazole adduct was added to the solution of 3-tert-butyldimethylsilyloxyphenylmagnesium bromide (above) at room temperature via double-ended needle. After stirring for 2 hours, the reaction was quenched by addition of 20 mL of saturated aqueous ammonium chloride. Anhydrous magnesium sulfate was added and the reaction was filtered. Solvent was removed under vacuum and the residue was redissolved in 800 mL of ethyl acetate. The ethyl acetate solution was washed with 4×200 mL of 1 M sodium hydroxide, 200 mL of water, and 200 mL of saturated aqueous sodium chloride. The organic layer was dried over anhydrous magnesium sulfate and the solvent was removed to give 32.7 g of dark oil. The oil was dissolved in 250 mL of tetrahydrofuran and 250 mL of 3 M hydrochloric acid and stirred for 2 hours at room temperature. The reaction solution was extracted with 3×250 mL of 2:1 diethyl ether/ethyl acetate. Ethyl acetate (300 mL) was added to the aqueous layer and pH was adjusted to 8 with aqueous sodium hydroxide. Layers were separated and the aqueous portion was extracted with another 3×300 mL of ethyl acetate. The combined organic extracts were washed with saturated aqueous sodium chloride, dried over anhydrous sodium sulfate, and the solvent was removed under vacuum to give 12.4 g of brown residue. The residue was purified by chromatography on 300 g of silica gel, eluting with a gradient of 1-15% ethanol in dichloromethane, to give 5.54 g of 4-((alpha-R)-alpha-((2S,5R)-4-allyl-2,5-dimethyl-1-piperazinyl)-3-hydroxybenzyl)-N,N-diethylbenzamide as a colorless gum (27% from 4-formyl-N,N-diethylbenzamide).

4-((alpha-R)-alpha-((2S,5R)-4-Allyl-2,5-dimethyl-1-piperazinyl)-3-hydroxybenzyl)-N,N-diethylbenzamide hydrochloride (0.97 g, 2.0 mmol) was dissolved in methylene chloride (10 mL) under nitrogen and triethylamine (0.919 mL, 0.667 g, 6.6 mmol) was added followed by N-phenyl bis(trifluoromethanesulfonimide) (0.785 g, 2.2 mmol). The reaction mixture was stirred at room temperature overnight and evaporated to dryness. The residue was dissolved in ethyl acetate (20 mL) and extracted with 5% sodium carbonate solution (2×15 mL). The organic layer was separated, dried over anhydrous sodium sulfate and evaporated to yield a viscous amber oil. The residue was dissolved in methylene chloride (5 mL), applied to a column of silica gel (4×30 cm), and eluted with ethanol/methylene chloride (2:98 v/v). Pure fractions containing desired product, as evidenced by t.l.c. (silica gel, EM60F$_{254}$, 2% NH$_4$OH in ethyl acetate, R$_f$=0.78) were evaporated to dryness to yield 4-((alpha-R)-alpha-((2S,5R)-4-allyl-2,5-dimethyl-1-piperazinyl)-3-trifluoromethyl-sulfonyloxybenzyl)-N,N-diethylbenzamide (0.72 g) as a yellow/amber oil. $^1$H NMR (CDCl3, 500 MHz); δ 1.00 (d, J=6.2 Hz, 3H); 1.12 (br m, 3H); 1.21 (d, J=6.1 Hz, 3H); 1.25 (br m, 3H); 1.83 (t, J=10.6 Hz, 1H); 2.60 (m, 3H); 2.91 (dd J=11.4, 2.7, 1H); 3.02 (m, 1H); 3.18 (br s, 2H); 3.28 (br m, 2H); 3.46 (dd, J=13.7, 5.5 Hz, 1H); 3.55 (br m, 2H); 5.25 (m, 2H); 5.31 (s, 1H); 5.88 (m, 1H); 7.02 (d, J=7.7 Hz, 1H); 7.05 (s, 1H); 7.23 (m, 2H); 7.32 (d, J=8.1 Hz, 2H); 7.40 (d, J=8.1 Hz, 2H); 7.46 (t, J=7.9 Hz, 1H).

EXAMPLE 10

4-((alpha-R)-alpha-((2S,5R)-2,5-Dimethyl-1-piperazinyl)-3-trifluoromethyl-sulfonyloxybenzyl)-N,N-diethylbenzamide The compound of Example 9 was de-allylated by the method of Genet [J. P. Genet, S. Lemaire-Audoire, M. Savignac, Tetrahedron Letters, 36, 1267-1270 (1995)] as follows. A solution of 4-((alpha-R)-alpha-((2S,5R)-4-allyl-2,5-dimethyl-1-piperazinyl)-3-trifluoromethylsulfonyloxybenzyl)-N,N-diethylbenzamide (Example 9, 0.72 g, 1.286 mmol) and thiosalicylic acid (234.7 mg, 1.522 mmol) in anhydrous tetrahydrofuran (4 mL) was stirred under nitrogen for 3 h at room temperature with a catalyst solution prepared by dissolution of bis(dibenzylidineacetone)palladium (36.46 mg, 0.0634 mmol) and 1,4-bis(diphenylphosphino)butane (27.04 mg, 0.0634 mmol) in tetrahydrofuran (0.5 mL). The reaction mixture was evaporated to dryness, the residue was dissolved in a mixture of ethyl acetate/ether (1:3, 20 mL) and extracted with 5% sodium carbonate solution (2×15 mL). The organic layer was diluted with two volumes of pentane and extracted with 3M-hydrochloric acid (5×4 mL). The aqueous solution was adjusted to pH 9-10 with concentrated ammonia solution and extracted with methylene chloride (3×10 mL). The combined organic extracts were dried over anhydrous sodium sulfate and evaporated to yield 4-((alpha-R)-alpha-((2S,5R)-2,5-Dimethyl-1-piperazinyl)-3-trifluoromethyl-sulfonyloxy benzyl)-N,N-diethylbenzamide as a brittle pale yellow foam (0.63 g). The product showed a single spot on thin layer chromatography (silica gel, EM60F$_{264}$, 2% NH$_4$OH in ethyl acetate, R$_f$=0.33). $^1$H NMR (CDCl$_3$, 500 MHz); δ 0.95 (d, J=6 Hz, 3H); 1.13 (br m, 3H); 1.20 (d, J=6.1 Hz, 3H); 1.26 (br m, 3H); 1.50 (t, J=9.7 Hz, 1H); 2.31 (m, 1H); 2.64 (dd J=11.3, 2.5, 1H); 2.71 (m, 1H); 2.95 (m, 1H); 3.29 (br m, 2H); 3.56 (br m, 2H); 5.43 (s, 1H); 7.04 (m, 1H); 7.21 (d, J=7.7, 1H); 7.24 (dd, J=8.2, 2.2 Hz, 1H); 7.34 (d, J=8.2 Hz, 2H); 7.42 (d, J=8.1 Hz, 2H); 7.48 (t, J=8 Hz, 1H).

EXAMPLE 11

4-((alpha-R)-alpha-((2S,5R)-2,5-Dimethyl-4-(4-fluorobenzyl)-1-piperazinyl)-3-hydroxybenzyl)-N,N-diethylbenzamide 4-((alpha-R)-alpha-((2S,5R)-2,5-Dimethyl-1-piperazinyl)-3-trifluoromethylsulfonyloxybenzyl)-N,N-diethylbenzamide (Example 10, 527.6 mg, 1.0 mmol) was dissolved in acetonitrile (4.0 mL) with sodium iodide (30 mg, 0.2 mmol). The suspension was stirred during the addition of triethylamine (800 μL, 580.8 mg, 5.74 mmol), followed by 4-fluorobenzyl bromide (249 μL, 378 mg, 2.0 mmol). The reaction mixture was sealed under nitrogen and stirred overnight at room temperature. The reaction mixture was evaporated to dryness and and the residue dissolved in ethyl acetate (10 mL). The organic solution was washed with saturated aqueous sodium bicarbonate solution (2×5 mL) and saturated sodium chloride solution (5 mL), dried over anhydrous sodium sulfate and evaporated to a golden oil (a single spot on silica gel, EM60F$_{264}$, 2% NH$_4$OH in ethyl acetate, R$_f$=0.86). This intermediate 4-((alpha-R)-alpha-((2S,5R)-2,5-dimethyl-4-(4-fluorobenzyl)-1-piperazinyl)-3-trifluoromethyl-sulfonyloxybenzyl)-N,N-diethylbenzamide (608.9 mg) was used without further purification. The oil was dissolved in ethanol (8 mL) and aqueous 2.5 M (10%) sodium hydroxide solution (5 mL, 12.5 mmol) was added. The reaction mixture was stirred at room temperature for 3.5 h and the ethanol was removed by evaporation. The oily suspension of the sodium salt was clarified by the addition of water (7.5 mL), and the pH of the solution was adjusted to 8.5-9 by the passage of gaseous carbon dioxide (from dry ice). The copious white precipitate was collected by filtration, washed well with water, and dried under vacuum (2 mm Hg) at room temperature overnight to yield 4-((alpha-R)-alpha-((2S,5R)-2,5-dimethyl-4-(4-fluorobenzyl)-1-piperazinyl)-3-hydroxybenzyl)-N,N-diethylbenzamide as a white solid (423.6 mg, 84%). Calc. for $C_{31}H_{38}FN_3O_2C$, 73.93; H, 7.61; N, 8.34. Found C, 73.91; H, 7.65; N, 8.21%. $^1$H NMR (CDCl3, 600 MHz); δ 1.05 (d, J=6.3 Hz, 3H); 1.07 (d, J=6.3 Hz, 3H); 1.11 (br m, 3H); 1.25 (br m, 3H); 1.97 (m, 2H); 2.53 (br m, 1H); 2.57 (br m, 1H); 2.61 (dd, J=9, 2.6 Hz, 1H); 2.65 (m, J=9, 2.4 Hz, 1H); 3.14 (d, J=13 Hz, 1H); 3.28 (br m, 2H); 3.54 (br m, 2H); 3.87 (d, J=13 Hz, 1H);

5.13 (s, 1H); 6.62 (s, 1H); 6.70 (m, 2H); 6.96 (t, J=8.5 Hz, 2H); 7.13 (t, J=7.8 Hz, 1H); 7.24 (m, 2H); 7.28 (d, J=8.2 Hz, 2H); 7.43 (d, J=8.1 Hz, 2H).

EXAMPLE 12

4-((alpha-R)-alpha-((2S,5R)-4-Benzyl-2,5-dimethyl-1-piperazinyl)-3-hydroxybenzyl)-N,N-diethylbenzamide This compound was prepared from 4-((alpha-R)-alpha-((2S,5R)-2,5-dimethyl-1-piperazinyl)-3-trifluoromethylsulfonyloxybenzyl)-N,N-diethylbenzamide (Example 10) by a procedure similar to that of Example 11 (88.5%). Calc. for $C_{31}H_{39}N_3O_2$ 0.9 $H_2O$: C, 74.19; H, 8.19; N, 8.37. Found C, 74.20; H, 7.88; N, 8.25%. $^1$H NMR (CDCl3, 300 MHz); δ 1.03 (d, J=6.1 Hz, 3H); 1.09 (d, J=6.1 Hz, 3H); 1.12 (br m, 3H); 1.24 (br m, 3H); 1.99 (m, 2H); 2.53 (br m, 2H); 2.60 (dd, J=9, 2 Hz, 1H); 2.65 (dd, J=9, 2 Hz, 1H); 3.17 (d, J=13 Hz, 1H); 3.29 (br m, 2H); 3.55 (br m, 2H); 3.95 (d, J=13 Hz, 1H); 5.13 (s, 1H); 6.55 (s, 1H); 6.64 (m, 2H); 7.10 (t, J=7.7 Hz, 2H); 7.13 (m, 1H); 7.24 (m, 5H); 7.45 (d, J=8.1 Hz, 2H).

EXAMPLE 13

4-{(2R,5S)-4-[(R)-(4-Diethylcarbamoylphenyl)(3-hydroxyphenyl)methyl]-2,5-dimethylpiperazin-1-ylmethyl)benzoic acid 4-((alpha-R)-alpha-((2S,5R)-2,5-Dimethyl-1-piperazinyl)-3-trifluoromethylsulfonyloxybenzyl)-N,N-diethylbenzamide (Example 10, 844 mg, 1.6 mmol) in acetonitrile (8 mL) was added to sodium iodide (45 mg, 0.3 mmol) and stirred during the addition of triethylamine (1.0 mL, 726 mg, 7.17 mol), followed by methyl 4-(bromomethyl benzoate (916.3 mg, 4.0 mmol). The reaction mixture was sealed under nitrogen and stirred at ambient temperature for 5 days. The solvent was removed by evaporation and the residue was partitioned between ethyl acetate (10 mL) and saturated aqueous sodium bicarbonate solution (3 mL). The organic layer was separated and the aqueous layer was extracted with ethyl acetate (3×10 mL). The combined organic extracts were dried over anhydrous sodium sulfate and evaporated to dryness. The residue was dissolved in ethyl acetate (5 mL) and applied to an intermediate (4×15 cm) Biotage silica column and eluted with ethyl acetate. Fractions containing the product, as evidenced by t.l.c. (silica, EM60F$_{254}$, 100% EtOAc, Rf=0.74) were evaporated to dryness and dried at room temperature and 2 mm Hg to yield methyl 4-{(2R,5S)-4-[(R)-(4-diethylcarbamoylphenyl)(3-(trifluoromethylsulfonyloxy)phenyl)methyl]-2,5-dimethylpiperazin-1-ylmethyl}benzoate as a rigid white foam. The solid (1.09 g, 1.615 mmol) was dissolved in ethanol (10 mL) and sodium hydroxide solution (2.5 M, 6.46 mL, 16.16 mmol) was added in approximately 1 mL aliquots. The slightly turbid reaction mixture clarified about 5 min after the last addition to yield a yellow solution which was stirred for 16 h at ambient temperature. The solution was diluted with an equal volume of water and the ethanol was removed by evaporation along with an estimated 50% of the aqueous volume. The pH of the solution was adjusted to 4 with 3 M hydrochloric acid, to yield a flocculent white solid, which was collected by filtration and washed sparingly with cold water. After removal of granular solid from the filter, the remaining small amount of gummy material was removed from the filter, sonicated with water (~1 mL) to yield a fine solid that was collected by filtration. After drying at room temperature and 5 mm Hg, both samples were shown to be identical by HPLC (Zorbax C-8, isocratic 40% 0.01 M NH$_4$OAc in MeOH, 3 min: gradient to 100% MeOH, 45 min: isocratic MeOH 5 min. 1.0 mL/min: λ$_{obs}$=210 nm, Rt=10.58 min) and combined to yield the title compound (888 mg, 85.9% from 4-((alpha-R)-alpha-((2S,5R)-2,5-dimethyl-1-piperazinyl)-3-trifluoromethylsulfonyl oxybenzyl)-N,N-diethylbenzamide). Calc. for $C_{32}H_{39}N_3O_4$ 1.5 NaCl 1.6 $H_2O$: C, 59.48; H, 6.58; N, 6.50. Found C, 59.50; H, 6.45; N, 6.32%. $^1$H NMR ((CD$_3$)$_2$SO+20% v/v 1-M NaOD in D$_2$O, 300 MHz); δ 0.93 (d, J=6.0 Hz, 3H); 0.98 (d, J=5.9 Hz, 3H; both doublets overlapping br m, 6H); 1.9 (m, 2H); 2.54 (m, 2H, partially obscured by DMSO); 3.13 (br m, 2H); 3.22 (d, J=14.2 Hz, 1H); 3.34 (br m, 2H); 3.71 (d, J=14.0 Hz, 1H); 4.66 (s, 1H); 5.97 (d, J=6.9 Hz, 1H); 6.16 (d, J=7.9, 1H); 6.23 (s, 1H); 6.72 (t, J=7.7 Hz, 1H); 7.16 (d, J=7.8 Hz, 4H); 7.38 (d, J=8.1 Hz, 2H); 7.72 (d, J=8.1 Hz, 2H). Mass spectrum: (ESI−, DP-120V, MeOH); m/z: 529.0, (M+, 100%); 528, ((M−1)+, 57%); 512.6, ((M−17)+, 95%).

EXAMPLE 14

3-((alpha-R)-alpha-((2S,5R)-4-Allyl-2,5-dimethyl-1-piperazinyl)-4-(diethylaminocarbonyl)benzyl)phenoxyacetic acid Sodium hydride (60% dispersion in oil, 250 mg (150 mg NaH, 6.25 mmol)) was washed with anhydrous tetrahydrofuran (2×5 mL) and anhydrous tetrahydrofuran (10 mL) was added as supernatant. 4-((alpha-R)-alpha-((2S,5R)-4-Allyl-2,5-Dimethyl-1-piperazinyl)-3-hydroxybenzyl)-N,N-diethylbenzamide hydrochloride (435 mg, 1.0 mmol, prepared in Example 9) was dissolved in the stirred suspension, and when effervescence had subsided, sodium iodide (15 mg, 0.1 mmol) was added. Methyl chloroacetate (350 μL, 434 mg, 4 mmol) was added to the stirred suspension under nitrogen and the reaction was stirred overnight at ambient temperature. The reaction mixture was partially neutralized by the passage of carbon dioxide gas (from dry ice), then glacial acetic acid added until the suspension showed a pH of 5 as measured by moistened indicator strips. The reaction mixture was evaporated to dryness, and the residue partitioned between ethyl acetate (10 mL) and 1 M HCl (5 mL). The organic layer was extracted with 1 M HCl (2×3 mL) and the pH of the combined acidic extracts was adjusted to 8 with saturated sodium carbonate solution. The oily aqueous suspension was extracted with ethyl acetate (3×10 mL) and the combined organic extracts were dried over anhydrous sodium sulfate. The solution was evaporated to a yellow gum. The residue was dissolved in ethyl acetate and applied to an intermediate (4×15 cm) silica gel Biotage column and eluted with 10% ethanol in ethyl acetate. Fractions containing the product, as evidenced by t.l.c. (silica, EM60F$_{254}$, 10% EtOH in EtOAc, Rf=0.52) were evaporated to dryness and dried at room temperature and 2 mm Hg to yield methyl 3-((alpha-R)-alpha-((2S,5R)-4-allyl-2,5-dimethyl-1-piperazinyl)-4-(diethylaminocarbonyl)benzyl)phenoxyacetate as a clear pale yellow gum. The residue was dissolved in ethanol (4 mL) and aqueous sodium hydroxide solution (2.5-M, 1.0 mL, 2.5 mmol) and stirred at room temperature for 6 h. The solution was evaporated to remove the bulk of the ethanol, and water (5 mL) added. Evaporation was continued until approximately 4 mL of solution remained, a further 8 mL of water added, and the solution was evaporated to approximately half its volume to ensure complete removal of ethanol. A small amount of suspended solid was removed by filtration, and the pH of the solution was adjusted to 6 with 3 M HCl. The solution was evaporated to dryness and the residue evaporated several times with absolute ethanol to ensure removal of water. The residue was extracted with ethanol (3×20 mL) and the combined ethanol extracts were filtered and evaporated to dryness. The gummy residue was triturated with ethyl acetate (5 mL), filtered, evaporated, and dried under high vacuum to yield 3-((alpha-R)-alpha-((2S,5R)-4-allyl-2,5-dimethyl-1-piperazinyl)-4-(diethylaminocarbonyl)benzyl)phenoxyacetic acid as a brittle white foam (52 mg, 9.5%). Calc. for $C_{29}H_{39}N_3O_4$ 0.9 NaCl 0.5 $H_2O$: C, 63.45; H, 7.20; N, 7.65. Found C, 63.83; H, 7.19; N, 7.25%. $^1H$ NMR (0.1-M NaOD in $D_2O$, 300 MHz); δ 0.86 (d, J=6.3 Hz, 3H); 0.94 (t, J=7.1 Hz, 3H); 1.01 (d, J=6.1 Hz, 3H); 1.09 (t, J=7.2 Hz, 3H); 1.81 (t, J=11.3 Hz, 1H); 2.09 (t, J=11.2 Hz, 1H); 2.43 (m, 2H); 2.73 (m, 3H); 3.13 (q, J=7.1 Hz, 2H); 3.25 (dd, J=13.5, 5.8 Hz, 1H); 3.38 (q, J=7.2 Hz, 2H); 4.32 (s, 2H); 5.09 (s, 1H): 5.14 (d, J=7.8 Hz, 1H); 5.24 (s, 1H); 5.74 (m, 1H); 6.73 (s, 1H); 6.80 (s, 2H); 7.21 (m, 3H); 7.32 (d, J=8.2 Hz, 2H). Mass spectrum: (ESI–, –5 KV, MeOH); m/z: 493, (M+, 25%); 492.5, ((M–1)+, 100%).

EXAMPLE 15

3-((alpha-R)-alpha-((2S,5R)-4-Benzyl-2,5-dimethyl-1-piperazinyl)-4-(diethylamino carbonyl)benzyl) phenoxyacetic acid Alkylation of 4-((alpha-R)-alpha-((2S,5R)-4-benzyl-2,5-dimethyl-1-piperazinyl)-3-hydroxybenzyl)-N,N-diethylbenzamide (Example 12) with ethyl iodoacetate, and subsequent hydrolysis of the ester as in Example 14 gave the title compound (84.6%) $^1H$ NMR (0.1-M NaOD in $CD_3OD$, 300 MHz); δ 1.10 (d, J=5.0 Hz, 3H); 1.11 (d, J=5.8 Hz, 3H; both doublets superimposed on m, 3H); 1.23 (m, 3H); 2.03 (m, 2H); 2.57 (m, 2H); 2.69 (m, 2H); 3.30 (m, 3H, superimposed on br m, 2H); 3.88 (d, J=13.1 Hz, 1H); 4.35 (s, 2H); 5.16 (s, 1H): 6.83 (m, 2H); 6.88 (s, 1H); 7.25 (m, 8H); 7.52 (d, J=8.1 Hz, 2H). Mass spectrum: (PFAB, glycerol matrix subtracted): m/z: 544.8, ((M+1)+, 82%).

EXAMPLE 16

3-((alpha-R)-4-(Diethylaminocarbonyl)-alpha-((2S, 5R)-2,5-dimethyl-4-(4-fluorobenzyl)-1-piperazinyl) benzyl)phenoxyacetic acid By an essentially similar procedure to that of Example 15, 3-((alpha-R)-4-(diethylaminocarbonyl)-alpha-((2S,5R)-2,5-dimethyl-4-(4-fluorobenzyl)-1-piperazinyl)benzyl)phenoxyacetic acid was made from 4-((alpha-R)-alpha-((2S, 5R)-2,5-dimethyl-4-(4-fluorobenzyl)-1-piperazinyl)-3-hydroxybenzyl)-N,N-diethylbenzamide (product from Example 11). Calc. for $C_{33}H_{40}FN_3O_4$ 0.6 NaCl 1.2 $H_2O$: C, 64.10; H, 6.91; N, 6.80; F, 3.07. Found C, 64.19; H, 6.91; N, 6.49; F, 3.06%. $^1H$ NMR ($D_2O$, 300 MHz); δ 0.95 (t, J=6.6 Hz, 3H); 1.04 (d, J=6.1 Hz, 3H); 1.09 (d, J=6.3 Hz, 3H superimposed on 1.102 (t, J=7.2 Hz, 3H)); 2.10 (br m, 1H); 2.58 (br m, 1H); 2.79 (br t, J=10.8 Hz, 1H); 2.93 (br d, J=12.5 Hz, 1H); 3.14 (d, J=6.5 Hz, 1H, superimposed on m, 2H); 3.39 (d, J=7.3 Hz, 1H, superimposed on m, 3H); 4.00 (m, 1H); 4.40 (s, 2H); 5.33 (br s, 1H): 6.76 (br m, 1H) overlapping 6.83 (m, 2H); 7.10 (m, 2H); 7.22 (m, 3H); 7.37 (m, 4H). Mass spectrum (PFAB, glycerol matrix subtracted); m/z: 562.1, (M+, 82%); 340.2 ((M–222)+, 40%); 109.0 ($C_7H_6F$+, 100%).

EXAMPLE 17

N,N-Diethyl-3-((R)-((2S,5R)-2,5-dimethyl-4-(3-hydroxybenzyl)piperazin-1-yl)(3-hydroxyphenyl) methyl)benzamide 3-Carboxybenzaldehyde (15.01 g, 100 mmol) was added to a 250 mL, 3-necked round bottom flask and stirred under nitrogen in 110 mL of toluene. Thionyl chloride (8.75 mL, 120 mmol) was added to the mixture, followed by the addition of 6 drops of DMF. A reflux condenser fitted with a calcium chloride drying tube was placed on the flask. The reaction was placed in an oil bath and heated at a bath temperature maintained below 120° C. The mixture was allowed to reflux for 1 hour after a clear solution was obtained and then cooled to room temperature. The solution was diluted with anhydrous toluene, and all volatiles were removed under vacuum.

The crude acid chloride was dissolved in 200 mL of dry tetrahydrofuran and cooled in an ice/water bath. Triethylamine (27.88 mL, 200 mmol) in 70 mL of dry tetrahydrofuran was added dropwise via an addition funnel, followed by diethylamine (10.45 mL, 100 mmol). The cloudy solution was allowed to warm to room temperature over 1 hour and stirred overnight. Water was added and the product was extracted with dichloromethane. The organic layer was washed with water and saturated sodium chloride solution and dried over sodium sulfate, and the solvent was removed under vacuum. 3-Formyl-N,N-diethylbenzamide (17.72 g) was obtained as a light golden oil (86% unchromatographed yield). $^1H$ NMR (300 MHz, DMSO-$d_6$): δ 1.04-1.18 (m, 6H); 3.17-3.45 (m, 4H); 7.65-7.66 (m, 2H); 7.85 (s, 1H); 7.93-7.94 (m, 1H); 10.03 (s, 1H).

A 12 L, 3-necked round bottom flask was charged with trans-2,5-dimethylpiperazine (767 g, 6.72 mol), which had been recrystallized from toluene to mp=115-119° C., and 600 mL of water. The flask was cooled in an ice bath and a solution of methanesulfonic acid (1290 g, 13.4 mol) in 600 mL of water was added slowly with stirring and cooling to maintain the temperature below 40° C. The solution was cooled to 20° C. and 800 mL of ethanol was added. A 500 mL addition funnel was filled with 60% aqueous potassium acetate from a 2 L reservoir of the solution, and potassium acetate was added to the reaction flask to adjust the pH to 4.0. A second addition funnel was charged with a solution of ethyl chloroformate (642 mL, 6.71 mol) in 360 mL of tetrahydrofuran. The ethyl chloroformate and potassium acetate solutions were simultaneously added dropwise with adjustment of rate to maintain the reaction solution at pH 4.0±0.1, with cooling as necessary to maintain temperature at 25° C. After addition of the ethyl chloroformate was complete, the reaction was stirred for 1 hour with continued addition of potassium acetate solution to maintain a pH of 4.0. The organic solvents were removed by distillation under vacuum. The remaining aqueous solution was washed with 1500 mL of ethyl acetate to remove any bis-carbamate impurity. The ethyl acetate wash was extracted with two 500 mL portions of 1 M hydrochloric acid to recover desired product. The acid extracts were combined with the original aqueous solution and the pH was adjusted to 11 by addition of 10 M sodium hydroxide, with cooling to maintain temperature below 40° C. The aqueous solution was extracted with two 1500 mL portions of ethyl acetate, the combined extracts were dried over magnesium sulfate, and the solvent was removed to give 927 g (74%) ethyl trans-2,5-dimethyl-1-piperazinecarboxylate as a yellow oil.

A mixture of ethyl trans-2,5-dimethyl-1-piperazinecarboxylate (643 g, 3.45 mol), allyl bromide (328 mL, 3.80 mol), and sodium carbonate (440 g, 4.15 mol) in 2500 mL of acetonitrile was heated at reflux for 1.5 hours. The reaction was cooled to room temperature, filtered, and the solvent removed under vacuum. The residue was dissolved in 4000 mL of dichloromethane and washed with two 500 mL portions of 1 M sodium hydroxide. The dichloromethane solution was dried over magnesium sulfate and the solvent was removed to give 630 g (81%) of ethyl trans-4-allyl-2,5-dimethyl-1-piperazinecarboxylate as an oil.

Ethyl trans-4-allyl-2,5-dimethyl-1-piperazinecarboxylate (630 g, 2.78 mol) was added to a solution of 87% potassium hydroxide pellets (2970 g, 46 mol) in 4300 mL of 95% ethanol and heated at reflux for 1.5 hours. Carbon dioxide evolution was observed for the first 0.5-1 hour of heating. The reaction was cooled below reflux temperature and 2000 mL of toluene was carefully added. Ethanol was removed by azeotropic distillation at 105 C, while adding an additional 4000 mL of toluene to the reaction flask during the course of the distillation. After collection of 9000 mL of distillate, the reaction was cooled to 100 C and 1000 mL of toluene was carefully added. The solution was slowly cooled to 5 C and maintained at 5° C. for 30 minutes. The solution was filtered, and the filter cake was washed with an additional 1500 mL of toluene. The filtrate was washed with 1000 mL of water, dried over magnesium sulfate, and the solvent was removed to give 296 g (69%) of trans-1-allyl-2,5-dimethylpiperazine as a dark liquid. NMR (300 MHz, DMSO-d$_6$): δ 0.87 (d, J=6.3 Hz, 3H); 0.92 (d, J=6.3 Hz, 3H); 1.63 (t, J=1 Hz, 1H); 2.05 (m, 1H); 2.30 (t, J=1 Hz, 1H); 2.6-2.8 (m, 4H); 3.33 (dd, J=5 Hz, J$_2$=14 Hz, 1H); 5.09 (d, J=8.7 Hz, 1H); 5.13 (d, J=14 Hz, 1H) 5.8 (m, 1H).

Di-p-toluoyl-D-tartaric acid (Schweizerhall, Inc., South Plainfield, N.J.) (1.25 Kg, 3.2 mol) was dissolved in hot (~60 C) 95% ethanol (16 L) and racemic trans-1-allyl-2,5-dimethylpiperazine (500 g, 3.2 mol) was added in several portions (caution: exothermic). The hot solution was seeded with crystals of the diastereoisomerically pure salt (obtained from a previous small-scale resolution) and cooled to room temperature over 2-3 hours. The solution was slowly stirred for 2 days at room temperature. The resulting salt was collected by filtration, washed twice with 95% ethanol, and dried under vacuum to give 826.5 g of a white solid (47%). The process was repeated with a second batch of the di-p-toluoyl-D-tartaric acid and racemic trans-1-allyl-2,5-dimethylpiperazine to give 869 g (50%).

The total of 1695 g of salt was divided into three batches and each batch was recrystallized twice in the following fashion. The salt was dissolved in refluxing 95% ethanol (~2.7 L/100 g of salt), and approximately half of the ethanol was removed by distillation. (Note: vigorous stirring was necessary during distillation to prevent crystallization on the vessel wall.) The hot solution was seeded with crystals of the pure diastereomeric salt, cooled to room temperature, and stirred slowly for 2 days before collecting the salt by filtration. (Note: a subsequent experiment suggested that crystallization time can be reduced from 2 days to 8 hours.) The total amount recovered was 1151 g. The salt was dissolved in 3 L of 2 M aqueous sodium hydroxide, and the aqueous solution was extracted with four 1 L portions of dichloromethane. The organic extracts were combined, dried over sodium sulfate, and solvent removed by rotary evaporation (temperature <20° C.) to give 293 g (29% based on racemic weight) of (2R,5S)-1-allyl-2,5-dimethylpiperazine as a clear oil. [α]$_D^{20}$=−55.1 (abs. ethanol, c=1.2). The trifluoroacetamide of the product was prepared with trifluoroacetic anhydride and analyzed by chiral capillary gas chromatography (Chiraldex B-PH column, 20 m×0.32 mm, Advanced Separation Technologies Inc., Whippany, N.J., 120° C.) indicating an enantiopurity of >99% ee (retention time of desired enantiomer, 11.7 min; other enantiomer, 10.7 min).

A solution of 3-bromophenol (500 g, 2.89 mol), tert.-butylchlorodimethylsilane (436 g, 2.89 mol), and imidazole (500 g, 7.22 mol) in 500 mL of dimethylformamide was stirred overnight at room temperature. The reaction solution was poured into 3000 mL of water and extracted with two 2000 mL portions of diethyl ether. The combined either extracts were dried over sodium sulfate and the solvent removed to give 846 g of 3-(bromophenoxy)-tert.-butyldimethylsilane as a pale yellow liquid. NMR (300 MHz, CDCl$_3$): δ 0.2 (s, 6H); 1.0 (s, 9H); 6.75 (m, 1H); 7.0 (br s, 1H); 7.1 (m, 2H). 3-(tert-butyldimethylsilyloxy)phenyl magnesium bromide was formed by the slow addition of 2.7 M n-butyllithium in heptane (150 mL, 405 mmol) to a solution of 3-bromophenoxy-tert-butyldimethylsilane (123.44 g, 429 mmol) in 500 mL anhydrous tetrahydrofuran at −70° C. After stirring 45 min. this cold solution was siphoned under nitrogen into a slurry of magnesium bromide etherate (110.62 g, 428 mmol) in 650 mL anhydrous tetrahydrofuran at room temperature, and stirred for 45 min.

2R,5S-1-allyl-2,5-dimethylpiperazine (2.31 g, 15 mmol), benzotriazole (1.80 g, 15.15 mmol, 1.01 eq., Aldrich), and 3-formyl-N,N-diethylbenzamide (3.08 g, 15 mmol) were mixed in 150 mL of dry toluene with two drops of triethylamine. The mixture was placed in an oil bath maintained below 140° C. (bath temperature). The flask was attached to a Dean-Stark trap and reflux condenser to allow the azeotropic removal of water. The mixture was refluxed for 2-3 hours, under a nitrogen atmosphere, then the majority of the toluene was removed under reduced pressure. The crude adduct was used in the following procedure without isolation.

The crude benzotriazole adduct was dissolved in ~20 mL of anhydrous tetrahydrofuran under nitrogen and added to a solution of 3-(tert-butyldimethylsilyloxy)phenyl magnesium bromide (1.75 equiv.) via a double-ended needle. After stirring under nitrogen at room temperature for 2 hours, the reaction was quenched with 6-8 mL of saturated ammonium chloride solution. Having stirred this for about half an hour, a generous amount of anhydrous magnesium sulfate was added. Filtering and concentrating the solution under reduced pressure gave the crude product contaminated with benzotriazole. This residue was dissolved in ethyl acetate and extracted with 10% aqueous NaOH solution three times to remove most of the benzotriazole. The organic layer was washed with saturated sodium chloride solution, dried over sodium sulfate/magnesium sulfate, and the ethyl acetate was removed under reduced pressure.

The t-butyldimethylsilyl protecting group was removed by dissolving the residue in 80 mL of tetrahydrofuran and adding 80 mL of 3N aqueous HCl at room temperature. The solution warmed upon acid addition. The mixture was stirred for 90 minutes at room temperature. The reaction was concentrated under reduced pressure to remove most of the organic solvent. The residue was partitioned between water and a solution of diethyl ether:ethyl acetate/3:2. The acidic aqueous layer was extracted twice with a solution of diethyl ether:ethyl acetate/ 3:2. The aqueous layer was adjusted to pH=2 using aqueous NaOH solution, at which point cloudiness persisted and a dark oil began to precipitate. Methylene chloride (~100 mL) was added and stirred briskly. This was separated and the aqueous layer was again extracted with 100 mL methylene chloride. Water (100 mL) was added to the combined organic extracts, and while stirring vigorously, was adjusted to pH=9 using aqueous NaOH solution. The organic layer was separated and the aqueous layer was again extracted with 100 mL methylene chloride. The combined methylene chloride extract was dried over sodium sulfate/magnesium sulfate, and the solvent was evaporated under reduced pressure. The crude material was chromatographed on a silica gel column (20-25 g of silica gel per gram of crude material) eluting first with methylene chloride, then with 20% ethyl acetate in methylene chloride to remove the less polar contaminant. Then, the column was eluted with a solution of ethyl acetate containing 2% ammonium hydroxide (solution A) in a gradient with methylene chloride (solution B), quickly increasing in polarity from 25% to 100% (solution A in B). The desired fractions were combined and the solvent was removed under reduced pressure. A 10:1 mixture of diastereomers (approx. 2.01 g) was obtained. Pure product was obtained by crystallization from a hot solution of ethyl acetate (5-10 mL) followed by slow addition of heptane (10-20 mL) and gradual cooling to give 1.35 g of (+)-3-((αR)-α-((2S,5R)-4-allyl-2,5-dimethyl-1-piperazinyl)-3-hydroxybenzyl)-N,N-diethylbenzamide as an off-white crystalline solid with >98% isomeric purity (as determined by NMR). NMR (400 MHz, DMSO-$d_6$): δ 0.91 (d, J=6.2 Hz, 3H); 0.99 (br s, 3H); 1.05 (d, J=6.2 Hz, 3H); 1.09 (br s, 3H); 1.84 (dd, $J_1$=7.3 Hz, $J_2$=10.9 Hz, 1H); 2.06 (dd, $J_1$=7.3 Hz, $J_2$=10.9 Hz, 1H); 2.48 (m, 1H); 2.51 (dd, $J_1$=2.7 Hz, $J_2$=10.9 Hz, 1H); 2.58 (br s, 1H); 2.70 (dd, $J_1$=2.7 Hz, $J_2$=10.9 Hz, 1H); 2.81 (dd, $J_1$=17.0 Hz, $J_2$=13.9 Hz, 1H); 3.12 (br s, 2H); 3.15 (dd, $J_1$=5.1 Hz, $J_2$=13.9 Hz, 1H); 3.38 (br s, 2H); 4.97 (br s, 1H); 5.07 (d, J=10.2 Hz, 1H), 5.14 (d, J=16.9 Hz, 1H); 5.70-5.82 (m, 1H); 6.64 (dd, $J_1$=2.1 Hz, $J_2$=8.0 Hz, 1H); 6.65 (s, 1H); 6.68 (d, J=7.7 Hz, 1H); 7.11 (t, J=8.0 Hz, 1H); 7.14 (d, J=7.6 Hz, 1H); 7.30 (s, 1H); 7.33 (t, J=7.6 Hz, 1H); 7.39 (d, J=8.0 Hz, 1H); 9.31 (s, 1H).

3-((R)-((2S,5R)-4-Allyl-2,5-dimethyl-1-piperazinyl)-3-hydroxybenzyl)-N,N-diethyl benzamide (4.35 g, 10 mmol), N-phenylbis(trifluoromethanesulfonimide) (3.82 g, 10.7 mmol), and triethylamine (3.1 mL, 22 mmol) were dissolved in 75 mL dichloromethane and stirred overnight at room temperature under nitrogen. After concentrating under reduced pressure, the residue was dissolved in 100 mL ethyl acetate and washed with $Na_2CO_3$ solution (3×100 mL), water (1×100 mL), and brine (1×100 mL). The solution was dried ($Na_2SO_4/MgSO_4$) and concentrated under reduced pressure. The residual oil was purified by chromatography on silica gel (2% $NH_4OH$ in EtOAc/$CH_2Cl_2$) to give 6.01 g (10.59 mmol) of 3-((alpha-R)-alpha-((2S,5R)-4-allyl-2,5-dimethyl-1-piperazinyl)-3-trifluoromethylsulfonyloxybenzyl)-N,N-diethylbenzamide as a viscous, golden yellow oil.

The allyl group was removed using Pd(dba)2/DPPB in the presence of thiosalicylic acid by the method of Genet [J. P. Genet, S. Lemaire-Audoire, M. Savignac, Tetrahedron Letters, 36, 1267-1270 (1995)]. The reaction was concentrated and the residue was dissolved in 50 mL ethyl acetate and 100 mL diethyl ether. After washing this with $Na_2CO_3$ solution (3×100 mL) and water (1×100 mL), the organic solution was extracted with 3 N HCl (3×20 mL) and 1 N HCl (1×20 mL). The acidic extract was adjusted to pH 8.5 using NaOH solution and extracted with dichloromethane (3×25 mL). The solution was dried ($Na_2SO_4/MgSO_4$) and concentrated under reduced pressure. The residual oil was purified by chromatography on silica gel (2% $NH_4OH$ in EtOAc/$CH_2Cl_2$) to give 4.39 g (8.32 mmol) of 3-((alpha-R)-alpha-((2S,5R)-2,5-dimethyl-1-piperazinyl)-3-trifluoromethyl-sulfonyloxybenzyl)-N,N-diethylbenzamide as a viscous, deep amber-orange colored oil.

The above free amine (0.70 g, 1.33 mmol) and 3-hydroxybenzaldehyde (0.32 g, 2.66 mmol) were placed in a 50 mL flask and sealed under nitrogen with 15 mL of tetrahydrofuran and 83.75 μl of acetic acid (1.46 mmol, 1.10 equiv.). The solution was stirred at room temperature for 20 minutes, and then sodium triacetoxyborohydride (0.56 g, 2.66 mmol) was added and stirred for 4 hours. The reaction solution was concentrated under reduced pressure. Ethanol (15 mL) and 10 mL of 10% NaOH solution was added to the residue and the reaction was stirred for 30 minutes. The ethanol was removed under vacuum. Water (25 mL) and ethyl acetate (25 mL) were added to the residue, and the pH was adjusted to 8.5 using 6 N HCl. The ethyl acetate layer was separated and the aqueous layer was extracted again with ethyl acetate (2×25 mL). The combined ethyl acetate extract was dried ($Na_2SO_4/MgSO_4$) and concentrated under reduced pressure. The residual oil was purified by chromatography on silica gel (EtOAc/$CH_2Cl_2$) to give 0.52 g (1.04 mmol) of the desired product as a white amorphous solid. The white powdery solid was precipitated from ethyl acetate/hexanes. $^1$H NMR (DMSO-$d_6$, 300 MHz); δ 0.99 (d, J=6.3 Hz, 3H); 1.02 (d, J=6.3 Hz, 3H, both doublets partially overlapped by br m, 3H); 1.08 (br m, 3H); 1.92 (m, 1H); 1.98 (m, 1H); 2.51 (m, 2H); 2.60 (m, 2H); 3.11 (d, J=13.8 Hz, 1H, overlapping br m, 2H); 3.30 (br m, 2H, partially obscured by $H_2O$); 3.67 (d, J=13.5 Hz, 1H); 4.97 (s, 1H); 6.56 (d, J=7.8 Hz, 1H); 6.67 (m, 4H); 7.03 (t, J=7.8 Hz, 1H); 7.13 (m, 2H); 7.36 (m, 4H); 9.18 (s, 1H); 9.32 (s, 1H). MS: 502.1 (M+1, 100%). Calculated for $C_{31}H_{39}N_3O_3.0.20C_4H_8O_2.0.40C_6H_{14}$: C, 74.18; H, 8.41; N, 7.59. Found: C, 74.25; H, 8.36; N, 7.61.

EXAMPLE 18

(−)-4-(αR)-α-((2R,5R)-4-Allyl-2,5-dimethyl-1-piperazinyl)-3-hydroxybenzyl)-N,N-diethyl-benzamide A mixture of 4-carboxybenzaldehyde (100 g, 0.66 mol), 1 L of dimethylformamide and 2 L of dichloromethane was cooled in an ice bath. Thionyl chloride (53 mL, 0.73 mol) was added dropwise while stirring. After 18 hours at room temperature, the mixture was cooled again and diethylamine (275 mL, 2.6 mol) was added dropwise. After stirring at room temperature for one hour the solvent was evaporated, and the residue was dissolved in aqueous 0.1 M sodium hydroxide and extracted with ethyl acetate. The organic layers were washed with water and brine, dried over sodium sulfate and evaporated to give a yellow oil. Chromatography on silica gel with ethanol (0-2%) in dichloromethane gave 44.2 g (32%) of 4-formyl-N,N-diethylbenzamide as a yellow oil.

A solution of 3-bromophenol (500 g, 2.89 mol), tert-butylchlorodimethylsilane (436 g, 2.89 mol), and imidazole (500 g, 7.22 mol) in 500 mL of dimethylformamide was stirred overnight at room temperature. The reaction solution was poured into 3000 mL of water and extracted with two 2000 mL portions of diethyl ether. The combined ether extracts were dried over sodium sulfate and the solvent removed to give 846 g of 3-(bromophenoxy)-tert-butyldimethylsilane as a pale yellow liquid. NMR (300 MHz, CDCl$_3$): δ 0.2 (s, 6H); 1.0 (s, 9H); 6.75 (m, 1H); 7.0 (br s, 1H); 7.1 (m, 2H).

3-(Bromophenoxy)-tert-butyldimethylsilane (61.7 g, 0.21 mol) was dissolved in 500 mL of dry tetrahydrofuran under nitrogen and cooled to −78° C. A solution of 1.6 M n-butyllithium in hexane (132 mL, 0.21 mol) was added dropwise at a rate to maintain the temperature below −70° C. The reaction was stirred for thirty minutes after the addition was complete and the cold solution was transferred via cannula to another vessel containing a cold (−78° C.) solution of 4-formyl-N,N-diethylbenzamide (44.1 g, 0.21 mol), from above, in 500 mL of dry tetrahydrofuran under nitrogen. The transfer rate was monitored to maintain the temperature below −70° C. After stirring for one hour at −78° C., the reaction was quenched with saturated aqueous ammonium chloride, warmed to room temperature and diluted with diethyl ether. The ether layer was washed with water and brine, dried over sodium sulfate and evaporated to give a yellow oil. Chromatography on silica gel with ethanol (0-1%) in dichloromethane gave 45.4 g (52%) of 4-(3-(tert-butyldimethylsilyloxy)-α-hydroxybenzyl)-N,N-diethylbenzamide as a white solid.

NMR (200 MHz, CDCl$_3$) δ: 0.15 (s, 6H); 1.0 (s, 9H); 1.2 (br m, 6H); 2.8 (br s, 1H); 3.25 (br m, 2H); 3.5 (br m, 2H); 5.75

(s, 1H); 6.75 (d, J=8 Hz, 1H); 6.85 (s, 1H); 7.95 (d, J=8 Hz, 1H); 7.2 (t, J=8 Hz, 1H); 7.35 (AB q, J=8 Hz, 4H).

Thionyl chloride (5.3 mL, 0.075 mol) was added to a solution of the benzhydryl alcohol from above (19.75 g, 0.048 mol) in 350 mL of dichloromethane. After stirring at room temperature overnight the solvent was evaporated, the residue was redissolved in toluene and again evaporated to drive off excess thionyl chloride and afford crude 4-(3-(tert-butyldimethylsilyloxy)-α-chlorobenzyl)-N,N-diethylbenzamide.

The crude benzhydryl chloride (approximately 0.047 mol), (2R,5R)-2,5-dimethylpiperazine (6.0 g, 0.53 mol), prepared from L-Ala-L-Ala-diketopiperazine (Bachem Chemicals, Philadelphia, Pa.) as described in *J. Org. Chem.* 50: 4909-13 (1985), sodium iodide (9.0 g, 0.06 mol), and diisopropylethylamine (14.19 g, 0.11 mol) were heated to reflux in acetonitrile (300 mL) under nitrogen for four hours. The acetonitrile was evaporated. The residue was dissolved in ethyl acetate (0.5 L) and washed with water. The organic phase was dried over sodium sulfate and concentrated in vacuo. The residue was dissolved in dichloromethane and purified on a short column of silica gel with ethanol (5%) in dichloromethane to provide a 1:1 mixture of two benzhydrylpiperazine diastereomers.

The mixture of benzhydrylpiperazine epimers (7.6 g, 14.9 mmol) was dissolved in 50 mL of dry tetrahydrofuran with 1.6 mL (18.6 mmol) of allyl bromide and 5.1 g (36.9 mmol) of sodium carbonate and stirred at room temperature under nitrogen for 2 days. The reaction solution was poured into ice water/ethyl acetate and separated. The organic layer was dried over sodium sulfate, and concentrated in vacuo. The residue was dissolved in a small amount of dichloromethane and placed on a column of silica gel. The diastereomers were separated by elution with a stepwise gradient of ethanol in dichloromethane. The first isomer was eluted with 1.3% ethanol in dichloromethane, and the second isomer was obtained with 1.6% ethanol in dichloromethane. Fractions containing the second isomer were combined and the solvent removed in vacuo to give 1.44 g of 4-((αR)-α-((2R,5R)-4-allyl-2,5-dimethyl-1-piperazinyl)-3-(tert-butyldimethylsilyloxy)benzyl)-N,N-diethylbenzamide as a brown oil.

NMR (300 MHz, DMSO-$d_6$): δ 0.12 (s, 6H); 0.89 (m, 12H); 0.93 (d, J=6.5 Hz, 3H); 1.05 (br s, 6H); 2.13 (app t, J=10.4 Hz, 1H); 2.25-2.37 (m, 3H); 2.55 (dd, partially obscured by DMSO, 1H); 2.71 (dd, J1=8.2 Hz, J2=14.2 Hz, 1H); 2.82 (br d, J=6.2 Hz, 1H); 3.12 (br s, 2H); 3.19 (m, obscured by water, 1H); 3.36 (br s, 2H); 4.55 (s, 1H); 5.08 (d, J=10.8 Hz, 1H), 5.14 (d, J=21.5 Hz, 1H); 5.72-5.83 (m, 1H); 6.62 (d, J=8.7 Hz, 1H); 6.99 (s, 1H); 7.00 (d, J=8.1 Hz, 1H); 7.12 (t, J=7.9 Hz, 1H); 7.23 (d, J=8.2 Hz, 2H); 7.33 (d, J=8.2 Hz, 2H).

The brown oil (1.05 g, 1.9 mmol) was dissolved in 8 mL of acetonitrile with 0.53 g (2.9 mmol) of tetraethylammonium fluoride dihydrate and stirred for 30 minutes at room temperature. After evaporation of solvent, the residue was redissolved in 1N hydrochloric acid and diethyl ether. The aqueous phase was separated and neutralized to pH 8 with 1N sodium hydroxide solution. The product was extracted using dichloromethane and washed with brine. The organic phase was dried over sodium sulfate and the solvent removed to give 0.69 g of (−)-4-((αR)-α-((2R,5R)-4-allyl-2,5-dimethyl-1-piperazinyl)-3-hydroxybenzyl)-N,N-diethylbenzamide.

NMR (300 MHz, DMSO-$d_6$): δ 0.95 (d, J=5.4 Hz, 3H); 1.00 (d, J=5.4 Hz, 3H); 1.13 (br s, 6H); 2.19 (app t, J=10.0 Hz, 1H); 2.26-2.41 (m, 3H); 2.55 (m, partially obscured by DMSO, 1H); 2.81 (dd, J1=7.9 Hz, J2=14.1 Hz, 1H); 2.89 (br d, J=6.2 Hz, 1H); 3.21 (br s, 2H); 3.21 (m, obscured, 1H); 3.39 (br s, 2H); 4.54 (s, 1H); 5.17 (d, J=11.3 Hz, 1H), 5.22 (d, J=19.6 Hz, 1H); 5.82-5.96 (m, 1H); 6.60 (d, J=7.8 Hz, 1H); 6.93 (m, 2H); 7.11 (t, J=7.9 Hz, 1H); 7.31 (d, J=7.9 Hz, 2H); 7.52 (d, J=7.9 Hz, 2H); 9.39 (s, 1H).

Mass spectrum (CI—CH$_4$) m/z: 436 (M+1, 12%), 282 (100%), 153 (3%). $[α]_D^{20}$=−27.8° (ethanol, c=1.2).

A portion of the free amine (0.100 g) was dissolved in ethanol and titrated with ethanolic hydrogen chloride to pH 4.0, followed by precipitation with diethyl ether from dichloromethane to give 0.089 g of the monohydrochloride salt as a hygroscopic beige powder. Calculations for $C_{27}H_{37}N_3O_2$ HCl 0.75 H$_2$O: C, 66.78; H, 8.20; N, 8.65; Cl, 7.30. Found: C, 66.90; H, 8.05; N, 8.69; Cl, 7.13.

EXAMPLE 19

(−)-4-((αS)-α-((2R,5R)-4-Allyl-2,5-dimethyl-1-piperazinyl)-3-hydroxybenzyl)-N,N-diethyl-benzamide The first isomer to elute from the column of Example 1 was obtained as 1.39 g of a brown oil.

NMR (300 MHz, DMSO-$d_6$): δ 0.11 (s, 6H); 0.86 (d, J=6.8 Hz, 3H); 0.88 (m, 9H); 0.94 (d, J=6.8 Hz, 3H); 1.02 (br s, 6H); 2.14 (app t, J=10.7 Hz, 1H); 2.25-2.38 (m, 3H); 2.55 (dd, partially obscured by DMSO, 1H); 2.73 (dd, J1=7.4 Hz, J2=13.9 Hz, 1H); 2.84 (br s, 1H); 3.13 (br s, 2H); 3.28 (m, obscured by water, 1H); 3.34 (br s, 2H); 4.55 (s, 1H); 5.09 (d, J=11.3 Hz, 1H), 5.14 (d, J=19.9 Hz, 1H); 5.74-5.84 (m, 1H); 6.63 (d, J=7.8 Hz, 1H); 6.90 (s, 1H); 7.02 (d, J=7.6 Hz, 1H); 7.13 (t, J=7.8 Hz, 1H); 7.23 (d, J=8.1 Hz, 2H); 7.47 (d, J=8.1 Hz, 2H).

The brown oil (0.95 g, 1.73 mmol) was dissolved in 8 mL of acetonitrile with 0.48 g (2.6 mmol) of tetraethylammonium fluoride dihydrate and stirred for 30 minutes at room temperature. After evaporation of solvent, the residue was redissolved in 1N hydrochloric acid and diethyl ether. The aqueous phase was separated and neutralized to pH 8 with 1N sodium hydroxide solution. The product was extracted using dichloromethane, then washed with brine. The organic phase was dried over sodium sulfate and the solvent removed to give 0.64 g. of (−)-4-((αS)-α-((2R,5R)-4-allyl-2,5-dimethyl-1-piperazinyl)-3-hydroxybenzyl)-N,N-diethylbenzamide.

NMR (300 MHz, DMSO-$d_6$): δ 0.89 (d, J=5.8 Hz, 3H); 0.98 (d, J=5.8 Hz, 3H); 1.08 (br s, 6H); 2.10-2.43 (m, 4H); 2.56 (m, partially obscured by DMSO, 1H); 2.78 (dd, J1=7.7 Hz, J2=14.4 Hz, 1H); 2.97 (br d, J=6.0 Hz, 1H); 3.17-3.43 (m, 5H); 4.51 (s, 1H); 5.13 (d, J=8.6 Hz, 1H), 5.19 (d, J=15.6 Hz, 1H); 5.75-5.88 (m, 1H); 6.57 (d, J=6.8 Hz, 1H); 6.88 (m, 2H); 7.04 (t, J=7.7 Hz, 1H); 7.27 (d, J=8.0 Hz, 2H); 7.50 (d, J=8.0 Hz, 2H); 9.34 (s, 1H). Mass spectrum (CI—CH4) m/z: 436 (M+1, 23%), 282 (100%), 153 (4%). $[α]_D^{20}$=−27.3° (ethanol, c=1.2).

A portion of the free amine (0.100 g) was dissolved in ethanol and titrated with ethanolic hydrogen chloride to pH 4.0, followed by precipitation with diethyl ether from dichloromethane to give 0.075 g of the monohydrochloride salt as a hygroscopic off-white powder. Calculations for $C_{27}H_{37}N_3O_2$ HCl 0.5 H$_2$O: C, 67.41; H, 8.17; N, 8.73; Cl, 7.37. Found: C, 67.16; H, 8.18; N, 8.81; Cl, 7.26.

EXAMPLE 20

(−)-4-((αR)-α-((2R,5R)-2,5-Dimethyl-4-propyl-1-piperazinyl)-3-hydroxybenzyl)-N,N-diethylbenzamide (−)-4-((αR)-α-((2R,5R)-4-Allyl-2,5-dimethyl-1-piperazinyl)-3-hydroxybenzyl)-N,N-diethylbenzamide (0.075 g, 0.17 mmol, Example 1) was dissolved in toluene (10 mL), added to a 3-neck flask containing Lindlar's catalyst (0.071 g, ca. 0.033 mmol Pd) and stirred for 3.5 hours under a hydrogen atmosphere. The solution was filtered through celite, the solvent was evaporated under vacuum, and the residue was purified on silica gel with 5% ethanol in dichloromethane to give 0.065 g. of (−)-4-((αR)-α-((2R,5R)-2,5-dimethyl-4-propyl-1-piperazinyl)-3-hydroxybenzyl)-N,N-diethylbenzamide as a light-brown solid.

NMR (300 MHz, DMSO-$d_6$): δ 0.75-1.41 (m, 17H); 2.10-2.43 (m, 4H); 2.56 (m, partially obscured by DMSO, 1H); 2.87 (m, 1H); 3.03-3.52 (m, 6H); 4.50 (s, 1H); 6.57 (d, J=7.4 Hz, 1H); 6.91 (m, 2H); 7.07 (t, J=7.9 Hz, 1H); 7.27 (d, J=7.7 Hz, 2H); 7.48 (d, J=7.7 Hz, 2H); 9.33 (s, 1H). Mass spectrum (CI—CH4) m/z: 438 (M+1, 5%), 282 (100%), 155 (4%). $[α]_D^{20}$=−37.5° (ethanol, c=1.2).

A portion of the free amine (0.055 g) was dissolved in ethanol and titrated with ethanolic hydrogen chloride to pH 4.0, followed by precipitation with diethyl ether from dichloromethane to give 0.045 g of the monohydrochloride salt as a hygroscopic beige powder. Calculations for $C_{27}H_{39}N_3O_2$ HCl 0.5 $H_2O$: C, 67.13; H, 8.55; N, 8.70. Found: C, 67.23; H, 8.55; N, 8.49.

EXAMPLE 21

(−)-4-((αS)-α-((2R,5R)-2,5-Dimethyl-4-propyl-1-piperazinyl)-3-hydroxybenzyl)-N,N-diethylbenzamide (−)-4-((αS)-α-((2R,5R)-4-Allyl-2,5-dimethyl-1-piperazinyl)-3-hydroxybenzyl)-N,N-diethylbenzamide (0.200 g, 0.46 mmol, Example 2) was dissolved in toluene (10 mL) and stirred for 4 hours under a hydrogen atmosphere. The solution was filtered through celite to give 0.182 g of crude product. The phenol was reprotected as follows to improve chromatographic resolution. A mixture of crude product (0.18 g), tert-butylchlorodimethylsilane (0.93 g), and imidazole (0.070 g) in 10 mL of acetonitrile was stirred overnight at room temperature. The reaction solution was poured into 100 mL of water and extracted with two 50 mL portions of dichloromethane. The combined extracts were dried over sodium sulfate and the solvent removed. The residue was purified on a column of silica gel with ethanol (0-4%) in dichloromethane to give 0.085 g of 4-((αS)-α-((2R,5R)-2,5-dimethyl-4-propyl-1-piperazinyl)-3-(tert-butyldimethylsilyloxy)benzyl)-N,N-diethylbenzamide as a light-brown solid.

The material (0.080 g) was dissolved in acetonitrile (5 mL) and treated with tetraethylammonium fluoride dihydrate (0.040 g). After 30 minutes the solvent was removed under reduced pressure. The residue was dissolved in 1N hydrochloric acid (5 mL) and washed two times with diethyl ether. The aqueous phase was then adjusted to pH 9 with 1N sodium hydroxide solution and extracted with dichloromethane. The dichloromethane extracts were combined, dried over sodium sulfate, and the solvent removed under reduced pressure to give 0.056 g of (−)-4-((αS)-α-((2R,5R)-2,5-dimethyl-4-propyl-1-piperazinyl)-3-hydroxybenzyl)-N,N-diethylbenzamide as a light-brown solid.

NMR (300 MHz, DMSO-$d_6$): δ 0.72-1.41 (m, 17H); 1.95-2.34 (m, 4H); 2.56 (m, partially obscured by DMSO, 1H); 2.91 (m, 1H); 3.02-3.48 (m, 6H); 4.47 (s, 1H); 6.56 (br s, 1H); 6.83 (m, 2H); 7.05 (m, 1H); 7.24 (d, J=6.5 Hz, 2H); 7.46 (d, J=6.5 Hz, 2H); 9.31 (s, 1H). Mass spectrum (CI—$CH_4$) m/z: 438 (M+1, 12%), 282 (100%), 155 (4%). $[α]_D^{20}$=−36.70° (ethanol, c=1.3).

The free amine (0.044 g) was dissolved in ethanol and titrated with ethanolic hydrogen chloride to pH 4.0, followed by precipitation with diethyl ether from dichloromethane to give 0.031 g of the monohydrochloride salt as a hygroscopic off-white powder. Calculations for $C_{27}H_{39}N_3O_2$ HCl $H_2O$: C, 65.90; H, 8.60; N, 8.54. Found: C, 65.72; H, 8.41; N, 8.52.

EXAMPLE 22

4-((αR)-α-(2S,5S)-4-Allyl-2,5-dimethyl-1-piperazinyl)-3-hydroxybenzyl)-benzamide 3-Bromophenoxy-tert-butyldimethylsilane (146 g, 0.51 mol, Example 1, infra) was dissolved in dry tetrahydrofuran under nitrogen and cooled to −78° C. A solution of 1.6 M n-butyllithium in hexane (318 mL, 0.51 mol) was added dropwise at a rate to maintain temperature below −70° C. The reaction was stirred for 30 minutes after the addition was complete, and the cold solution was transferred to another vessel containing a cold (−78° C.) solution of 4-bromobenzaldehyde (94.3 g, 0.51 mol) in 1000 mL of dry tetrahydrofuran under nitrogen. The transfer rate was monitored to maintain reaction temperature below −70° C. The reaction mixture was stirred for another 45 minutes at −78° C. and then quenched with 100 mL of saturated aqueous ammonium chloride. After warming to room temperature, the mixture was diluted with 2000 mL of diethyl ether and washed with 2000 mL of water followed by 500 mL of saturated sodium chloride. The ethereal solution was dried over sodium sulfate and the solvent removed to give 197.2 g of crude α-(4-bromophenyl)-3-(tert-butyldimethylsilyloxy)benzyl alcohol as a yellow oil.

NMR (200 MHz, $CDCl_3$): δ 0.2 (s, 6H); 0.9 (s, 6H); 5.7 (s, 1H); 6.75 (dd, J1=2 Hz, J2=8 Hz, 1H); 6.8 (br s, 1H); 6.9 (d, J=8 Hz, 1H); 7.15 (t, J=8 Hz, 1H); 7.25 and 7.45 (AB q, J=8 Hz, 4H).

The crude benzhydryl alcohol (53.2 g, 135 mmol) was dissolved in 1000 mL of dichloromethane and 14.7 mL (202 mmol) of thionyl chloride was added dropwise. The solution was stirred overnight at room temperature and the solvent was removed under vacuum. The crude product was redissolved in 500 mL of toluene and the solvent again was removed under vacuum to eliminate excess thionyl chloride, providing crude α-(4-bromophenyl)-3-(tert-butyldimethylsilyloxy) benzyl chloride as a dark oil.

NMR (200 MHz, $CDCl_3$): δ 0.2 (s, 6H); 1.0 (s, 9H); 6.0 (s, 1H); 6.78 (dd, J1=1 Hz, J2=8 Hz, 1H); 6.9 (m, 2H); 7.2 (t, J=8 Hz, 2H); 7.27 and 7.47 (AB q, J=8 Hz, 4H).

The crude benzhydryl chloride (approx. 42 mmol) was combined with 9.55 g (84 mmol) of (+)-(2S,5S)-2,5-dimethylpiperazine, prepared from L-Ala-L-Ala-diketopiperazine (Bachem Chemicals, Philadelphia, Pa.) as described in *J. Org. Chem.* 50: 4909-13 (1985), and 30 mL of toluene and heated at reflux overnight under nitrogen. The toluene was removed under vacuum, and the residue was redissolved in diethyl ether and washed with 1.0 M sodium hydroxide followed by saturated aqueous sodium chloride. The ether solution was dried over sodium sulfate and the solvent removed to give a dark oil. The product was purified by chromatography on silica gel (Waters Prep 500) with 0.5-0.7% ethanol in dichloromethane with 0.1% triethylamine to give 8.01 g (39%) of (2S,5S)-1-(4-bromo-α-(3-(tert-butyldimethylsilyloxy)phenyl)benzyl)-2,5-dimethylpiperazine as a 1:1 mixture of diastereomers.

The purified benzhydrylpiperazine (1.51 g, 3.1 mmol) was dissolved in 20 mL of dry tetrahydrofuran with 0.27 mL (3.2 mmol) of allyl bromide and 1.6 g (15.5 mmol) of sodium carbonate and heated at reflux overnight under nitrogen. The cooled reaction solution was filtered and the solvent removed to give 1.62 g of crude (2S,5S)-1-allyl-4-(4-bromo-α-(3-(tert-butyldimethylsilyloxy)phenyl)benzyl)-2,5-dimethylpiperazine as a yellow oil.

NMR (200 MHz, CDCl$_3$): δ 0.15 (s, 6H); 0.95-1.1 (m, 12H); 1.45 (m, 1H); 2.2-2.55 (m, 4H); 2.6 (m, 1H); 2.75-3.1 (m, 2H); 3.4 (m, 1H); 4.45 (s, 1H); 5.1-5.25 (m, 3H); 5.85 (m, 1H); 6.75 (d, J=8 Hz, 1H); 6.8-6.95 (m, 2H); 7.1 (m, 1H); 7.2-7.5 (m, 4H).

The product from above (1.40 g, 2.6 mmol) was dissolved in 10 mL of dry tetrahydrofuran and cooled to −78° C. under nitrogen. A solution of 1.6 M n-butyllithium in hexane (1.6 mL, 2.6 mmol) was added dropwise at a rate to maintain temperature below −70° C. After the orange solution was stirred an additional 30 minutes at low temperature, anhydrous carbon dioxide gas was introduced into the reaction solution at a rate to maintain temperature below −60° C. Carbon dioxide addition was stopped when the color of the reaction solution became a pale yellow. The reaction was allowed to warm to room temperature with stirring and the solvent was removed under vacuum. The residue was redissolved in 50 mL of toluene and the solvent again removed under vacuum in order to eliminate residual n-bromobutane. The reaction provided 1.39 g of the lithium salt of 4-((αR)-α-((2S,5S)-4-allyl-2,5-dimethyl-1-piperazinyl)-3-(tert-butyldimethylsilyloxy)benzyl)benzoic acid.

The lithium benzoate salt (1.39 g, 2.8 mmol) was dissolved in dichloromethane and cooled to 0° C. Thionyl chloride (0.3 mL, 4.2 mmol) was added dropwise. After stirring for two hours at 0° C. concentrated ammonium hydroxide (6.0 mL) was added. The resulting dark yellow slurry was allowed to warm to room temperature and stirred for another hour. The reaction solution was washed with water and dried over sodium sulfate. After removal of the solvent, the residue was purified by chromatography on silica gel with 1-3% methanol in dichloromethane to give 0.10 g of 4-((αR)-α-((2S,5S)-4-allyl-2,5-dimethyl-1-piperazinyl)-3-(tert-butyldimethylsilyloxy)benzyl)benzamide as a yellow resin.

NMR (200 MHz, CDCl$_3$): δ 0.15 (s, 6H); 0.95 (s, 9H); 0.97 (d, J=6 Hz, 3H); 1.05 (d, J=6 Hz, 3H); 2.2-2.5 (m, 4H); 2.65 (m, 1H); 2.8 (m, 1H); 3.0 (m, 1H); 3.5 (m, 1H); 4.55 (s, 1H); 5.1 (d, J=10 Hz, 1H); 5.2 (d, J=16 Hz, 1H); 5.85 (m, 1H); 6.1 (br s, 2H); 6.65 (d, J=8 Hz, 1H); 6.9 (s, 1H); 6.95 (d, J=8 Hz, 1H); 7.1 (t, J=8 Hz, 1H); 7.55 and 7.7 (AB q, J=8 Hz, 4H).

The benzamide from above (0.10 g, 0.20 mmol) was dissolved in 2 mL of acetonitrile with 60 mg (0.3 mmol) of tetraethylammonium fluoride hydrate and stirred for 1 hour at room temperature. After evaporation of the solvent, the residue was redissolved in dichloromethane and washed with water (pH=8), then dried over sodium sulfate and the solvent removed to give 90 mg of a beige solid. The monohydrochloride salt was prepared by titration to pH 4.3 with ethanolic hydrogen chloride (approximately 0.2 M) followed by precipitation with diethyl ether to give 49 mg of 4-((αR)-α-((2S,5R)-4-allyl-2,5-dimethyl-1-piperazinyl)-3-hydroxy-benzyl)benzamide hydrochloride as a hygroscopic white powder. Calculations for $C_{23}H_{29}N_3O_2$ HCl 1.5 $H_2O$: C, 62.36; H, 7.51; N, 9.49; Cl, 8.00. Found: C, 62.38; H, 7.42; N, 9.41; Cl, 8.10. Mass spec (CI—CH$_4$): m/z 380 (M+1, 100%)

EXAMPLE 23

(−)-3-((S)-((2S,5R)-4-Allyl-2,5-dimethyl-1-piperazinyl)(3-thienyl)methyl)phenol

A solution of 3-bromophenol (500 g, 2.89 mol), tert-butylchlorodimethylsilane (436 g, 2.89 mol), and imidazole (500 g, 7.22 mol) in 500 mL of dimethylformamide was stirred overnight at room temperature. The reaction solution was poured into 3000 mL of water and extracted with two 2000 mL portions of diethyl ether. The combined ether extracts were dried over sodium sulfate and the solvent removed to give 846 g of 3-(bromophenoxy)-tert-butyldimethylsilane as a pale yellow liquid. NMR (300 MHz, CDCl$_3$): δ 0.2 (s, 6H); 1.0 (s, 9H); 6.75 (m, 1H); 7.0 (br s, 1H); 7.1 (m, 2H).

A 12 L, 3-necked round bottom flask was charged with trans-2,5-dimethylpiperazine (767 g, 6.72 mol), which had been recrystallized from toluene to mp=115-119° C., and 600 mL of water. The flask was cooled in an ice bath and a solution of methanesulfonic acid (1290 g, 13.4 mol) in 600 mL of water was added slowly with stirring and cooling to maintain the temperature below 40° C. The solution was cooled to 20° C. and 800 mL of ethanol was added. A 500 mL addition funnel was filled with 60% aqueous potassium acetate from a 2 L reservoir of the solution, and potassium acetate was added to the reaction flask to adjust the pH to 4.0. A second addition funnel was charged with a solution of ethyl chloroformate (642 mL, 6.71 mol) in 360 mL of tetrahydrofuran. The ethyl chloroformate and potassium acetate solutions were simultaneously added dropwise with adjustment of rate to maintain the reaction solution at pH 4.0±0.1, with cooling as necessary to maintain temperature at 25° C. After addition of the ethyl chloroformate was complete, the reaction was stirred for 1 hour with continued addition of potassium acetate solution to maintain a pH of 4.0. The organic solvents were removed by distillation under vacuum. The remaining aqueous solution was washed with 1500 mL of ethyl acetate to remove any bis-carbamate impurity. The ethyl acetate wash was extracted with two 500 mL portions of 1M hydrochloric acid to recover desired product. The acid extracts were combined with the original aqueous solution and the pH was adjusted to 11 by addition of 10 M sodium hydroxide, with cooling to maintain temperature below 40 C. The aqueous solution was extracted with two 1500 mL portions of ethyl acetate, the combined extracts were dried over magnesium sulfate, and the solvent was removed to give 927 g (74%) ethyl trans-2,5-dimethyl-1-piperazinecarboxylate as a yellow oil.

A mixture of ethyl trans-2,5-dimethyl-1-piperazinecarboxylate (643 g, 3.45 mol), allyl bromide (328 mL, 3.80 mol), and sodium carbonate (440 g, 4.15 mol) in 2500 mL of acetonitrile was heated at reflux for 1.5 hours. The reaction was cooled to room temperature, filtered, and the solvent removed under vacuum. The residue was dissolved in 4000 mL of dichloromethane and washed with two 500 mL portions of 1 M sodium hydroxide. The dichloromethane solution was dried over magnesium sulfate and the solvent was removed to give 630 g (81%) of ethyl trans-4-allyl-2,5-dimethyl-1-piperazinecarboxylate as an oil.

Ethyl trans-4-allyl-2,5-dimethyl-1-piperazinecarboxylate (630 g, 2.78 mol) was added to a solution of 87% potassium hydroxide pellets (2970 g, 46 mol) in 4300 mL of 95% ethanol and heated at reflux for 1.5 hours. Carbon dioxide evolution was observed for the first 0.5 1 hour of heating. The reaction was cooled below reflux temperature and 2000 mL of toluene was carefully added. Ethanol was removed by azeotropic distillation at 105 C, while adding an additional 4000 mL of toluene to the reaction flask during the course of the distillation. After collection of 9000 mL of distillate, the reaction was cooled to 100 C and 1000 mL of toluene was carefully added. The solution was slowly cooled to 5 C and maintained at 5 C for 30 minutes. The solution was filtered, and the filter cake was washed with an additional 1500 mL of toluene. The filtrate was washed with 1000 mL of water, dried over magnesium sulfate, and the solvent was removed to give 296 g (69%) of trans-1-allyl-2,5-dimethylpiperazine as a dark liquid. NMR (300 MHz, DMSO-$d_6$): δ 0.87 (d, J=6.3 Hz, 3H); 0.92 (d, J=6.3 Hz, 3H); 1.63 (t, J=11 Hz, 1H); 2.05 (m, 1H); 2.30 (t, J=11 Hz, 1H); 2.6-2.8 (m, 4H); 3.33 (dd, $J_1$=5 Hz, $J_2$=14 Hz, 1H); 5.09 (d, J=8.7 Hz, 1H); 5.13 (d, J=14 Hz, 1H) 5.8 (m, 1H).

Di-p-toluoyl-D-tartaric acid (Schweizerhall, Inc., South Plainfield, N.J.) (1.25 Kg, 3.2 mol) was dissolved in hot (~60° C.) 95% ethanol (16 L) and racemic trans-1-allyl-2,5-dimethylpiperazine (500 g, 3.2 mol) was added in several portions (caution: exothermic). The hot solution was seeded with crystals of the diastereoisomerically pure salt (obtained from a previous small-scale resolution) and cooled to room temperature over 2-3 hours. The solution was slowly stirred for 2 days at room temperature. The resulting salt was collected by filtration, washed twice with 95% ethanol, and dried under vacuum to give 826.5 g of a white solid (47%). The process was repeated with a second batch of the di-p-toluoyl-D-tartaric acid and racemic trans-1-allyl-2,5-dimethylpiperazine to give 869 g (50%).

The total of 1695 g of salt was divided into three batches and each batch was recrystallized twice in the following fashion. The salt was dissolved in refluxing 95% ethanol (~2.7 L/100 g of salt), and approximately half of the ethanol was removed by distillation. (Note: vigorous stirring was necessary during distillation to prevent crystallization on the vessel wall.) The hot solution was seeded with crystals of the pure diastereomeric salt, cooled to room temperature, and stirred slowly for 2 days before collecting the salt by filtration. (Note: a subsequent experiment suggested that crystallization time can be reduced from 2 days to 8 hours.) The total amount recovered was 1151 g. The salt was dissolved in 3 L of 2 M aqueous sodium hydroxide, and the aqueous solution was extracted with four 1 L portions of dichloromethane. The organic extracts were combined, dried over sodium sulfate, and solvent removed by rotary evaporation (temperature <20° C.) to give 293 g (29% based on racemic weight) of (2R,5S)-1-allyl-2,5-dimethylpiperazine as a clear oil. $[\alpha]_D^{20}$=−55.1 (abs. ethanol, c=1.2). The trifluoroacetamide of the product was prepared with trifluoroacetic anhydride and analyzed by chiral capillary gas chromatography (Chiraldex B-PH column, 20 m×0.32 mm, Advanced Separation Technologies Inc., Whippany, N.J., 120° C.) indicating an enantiopurity of >99% ee (retention time of desired enantiomer, 11.7 min; other enantiomer, 10.7 min).

3-Phenoxy-tert-butyldimethylsilane magnesium bromide was formed by the slow addition of 2.7 M n-butyllithium in heptane (150 mL, 405 mmol) to a solution of 3-bromophenoxy-tert-butyldimethylsilane (123.44 g, 429 mmol) in 500 mL anhydrous tetrahydrofuran at −70° C. After stirring 45 min. this cold solution was siphoned under nitrogen into a slurry of magnesium bromide etherate (110.62 g, 428 mmol) in 650 mL anhydrous tetrahydrofuran at room temperature, and stirred for 45 min.

Thiophene-3-carboxaldehyde (29.09 g, 259 mmol), benzotriazole (30.91 g, 259 mmol), and (2R,5S)-1-allyl-2,5-trans-dimethylpiperazine (40.01 g, 259 mmol) were dissolved in 250 mL toluene and heated to a gentle reflux. The water-toluene azeotrope was collected in a Dean-Stark trap over the course of 2.5 hours. The remaining solvent was removed under vacuum. The residue was dissolved in 150 mL anhydrous tetrahydrofuran and added to a solution of 3-phenoxy-tert-butyldimethylsilane magnesium bromide in anhydrous tetrahydrofuran (1150 mL, 0.35 M) under a nitrogen atmosphere.

The reaction was stirred at room temperature for 2 hours and then quenched by the addition of 25 mL saturated $NH_4Cl$ solution. Anhydrous magnesium sulfate (~5 g) and Celite (~10 g) were added. The mixture was stirred and filtered, and the solvent was removed under reduced pressure. The residue was dissolved in ethyl acetate and washed first with 0.5 N NaOH solution (5×200 mL) and then with brine (1×200 mL). The solution was dried ($Na_2SO_4/MgSO_4$) and concentrated under reduced pressure.

The dark residue was dissolved in 250 mL anhydrous acetonitrile and tetraethyl-ammonium fluoride dihydrate (72.26 g, 390 mmol) was added. After stirring for 90 min. the reaction was concentrated and the residue was dissolved in 200 mL ethyl acetate. The mixture was extracted with dilute $NaHCO_3$ solution (3×200 mL) and with water (1×200 mL). The organic layer was diluted with 200 mL diethyl ether and extracted with 10% citric acid solution (8×200 mL). The combined aqueous extracts was adjusted to pH 8.5 using 50% NaOH solution and extracted with dichloromethane (3×200 mL). The solution was dried ($Na_2SO_4/MgSO_4$) and concentrated under reduced pressure. The resulting tan solid (53.25 g, 155 mmol) was crystallized twice from 225 mL of 2:1/ isopropanol:water to yield fluffy, white needle crystals (34.14 g, 99.7 mmol), $[\alpha]_D^{20}$=−8.33° (abs. ethanol, c=1.0).

$^1$H NMR (500 MHz, $d_6$-DMSO): δ9.32 (s, 1H), 7.44 (dd, J=3.2, 4.9 Hz, 1H), 7.15 (s, 1H), 7.13 (t, J=8.25 Hz, 1H), 6.98 (d, J=4.9 Hz, 1H), 6.66-6.70 (m, 3H), 5.73-5.81 (m, 1H), 5.15 (d, J=17.1 Hz, 1H), 5.09 (d, J=10.5 Hz, 1H), 5.02 (s, 1H), 3.20 (br d, J=10.2 Hz, 1H), 2.78 (dd, J=7.3, 7.5 Hz, 1H), 2.68 (dd, J=2.6, 11.3 Hz, 1H), 2.59 (dd, J=1, 9.3 Hz, 1H), 2.44 (br s, 2H), 2.02 (t, J=8.6 Hz, 1H), 1.81 (t, J=8.1 Hz, 1H), 1.09 (d, J=6 Hz, 3H), 0.91 (d, J=6 Hz, 3H).

Calculated for $C_{20}H_{26}N_2OS$: C, 70.14; H, 7.65; N, 8.18; S, 9.36%. Found: C, 70.19; H, 7.58; N, 8.12; S, 9.33%.

EXAMPLE 24

3-((S)-((2S,5R)-4-Benzyl-2,5-dimethyl-1-piperazinyl)(3-thienyl)methyl)phenol

A solution of 3-bromophenol (500 g, 2.89 mol), tert.-butylchlorodimethylsilane (436 g, 2.89 mol), and imidazole (500 g, 7.22 mol) in 500 mL of dimethylformamide was stirred overnight at room temperature. The reaction solution was poured into 3000 mL of water and extracted with two 2000 mL portions of diethyl ether. The combined either extracts were dried over sodium sulfate and the solvent removed to give 846 g of 3-(bromophenoxy)-tert.-butyldimethylsilane as a pale yellow liquid. NMR (300 MHz, $CDCl_3$): δ 0.2 (s, 6H); 1.0 (s, 9H); 6.75 (m, 1H); 7.0 (br s, 1H); 7.1 (m, 2H).

A 12 L, 3-necked round bottom flask was charged with trans-2,5-dimethylpiperazine (767 g, 6.72 mol), which had been recrystallized from toluene to mp=115-119° C., and 600 mL of water. The flask was cooled in an ice bath and a solution of methanesulfonic acid (1290 g, 13.4 mol) in 600 mL of water was added slowly with stirring and cooling to maintain the temperature below 40° C. The solution was cooled to 20° C. and 800 mL of ethanol was added. A 500 mL addition funnel was filled with 60% aqueous potassium acetate from a 2 L reservoir of the solution, and potassium acetate was added to the reaction flask to adjust the pH to 4.0. A second addition funnel was charged with a solution of ethyl chloroformate (642 mL, 6.71 mol) in 360 mL of tetrahydrofuran. The ethyl chloroformate and potassium acetate solutions were simultaneously added dropwise with adjustment of rate to maintain the reaction solution at pH 4.0±0.1, with cooling as necessary to maintain temperature at 25° C. After addition of the ethyl chloroformate was complete, the reaction was stirred for 1 hour with continued addition of potassium acetate solution to maintain a pH of 4.0. The organic solvents were removed by distillation under vacuum. The remaining aqueous solution was washed with 1500 mL of ethyl acetate to remove any bis-carbamate impurity. The ethyl acetate wash was extracted with two 500 mL portions of 1 M hydrochloric acid to recover desired product. The acid extracts were combined with the original aqueous solution and the pH was adjusted to 11 by addition of 10 M sodium hydroxide, with cooling to maintain temperature below 40° C. The aqueous solution was extracted with two 1500 mL portions of ethyl acetate, the combined extracts were dried over magnesium sulfate, and the solvent was removed to give 927 g (74%) ethyl trans-2,5-dimethyl-1-piperazinecarboxylate as a yellow oil.

A mixture of ethyl trans-2,5-dimethyl-1-piperazinecarboxylate (643 g, 3.45 mol), allyl bromide (328 mL, 3.80 mol), and sodium carbonate (440 g, 4.15 mol) in 2500 mL of acetonitrile was heated at reflux for 1.5 hours. The reaction was cooled to room temperature, filtered, and the solvent removed under vacuum. The residue was dissolved in 4000 mL of dichloromethane and washed with two 500 mL portions of 1 M sodium hydroxide. The dichloromethane solution was dried over magnesium sulfate and the solvent was removed to give 630 g (81%) of ethyl trans-4-allyl-2,5-dimethyl-1-piperazinecarboxylate as an oil.

Ethyl trans-4-allyl-2,5-dimethyl-1-piperazinecarboxylate (630 g, 2.78 mol) was added to a solution of 87% potassium hydroxide pellets (2970 g, 46 mol) in 4300 mL of 95% ethanol and heated at reflux for 1.5 hours. Carbon dioxide evolution was observed for the first 0.5-1 hour of heating. The reaction was cooled below reflux temperature and 2000 mL of toluene was carefully added. Ethanol was removed by azeotropic distillation at 105° C., while adding an additional 4000 mL of toluene to the reaction flask during the course of the distillation. After collection of 9000 mL of distillate, the reaction was cooled to 100° C. and 1000 mL of toluene was carefully added. The solution was slowly cooled to 5° C. and maintained at 5° C. for 30 minutes. The solution was filtered, and the filter cake was washed with an additional 1500 mL of toluene. The filtrate was washed with 1000 mL of water, dried over magnesium sulfate, and the solvent was removed to give 296 g (69%) of trans-1-allyl-2,5-dimethylpiperazine as a dark liquid. NMR (300 MHz, DMSO-$d_6$): δ 0.87 (d, J=6.3 Hz, 3H); 0.92 (d, J=6.3 Hz, 3H); 1.63 (t, J=11 Hz, 1H); 2.05 (m, 1H); 2.30 (t, J=11 Hz, 1H); 2.6-2.8 (m, 4H); 3.33 (dd, $J_1$=5 Hz, $J_2$=14 Hz, 1H); 5.09 (d, J=8.7 Hz, 1H); 5.13 (d, J=14 Hz, 1H) 5.8 (m, 1H).

Di-p-toluoyl-D-tartaric acid (Schweizerhall, Inc., South Plainfield, N.J.) (1.25 Kg, 3.2 mol) was dissolved in hot (~60° C.) 95% ethanol (16 L) and racemic trans-1-allyl-2,5-dimethylpiperazine (500 g, 3.2 mol) was added in several portions (caution: exothermic). The hot solution was seeded with crystals of the diastereoisomerically pure salt (obtained from a previous small-scale resolution) and cooled to room temperature over 2-3 hours. The solution was slowly stirred for 2 days at room temperature. The resulting salt was collected by filtration, washed twice with 95% ethanol, and dried under vacuum to give 826.5 g of a white solid (47%). The process was repeated with a second batch of the di-p-toluoyl-D-tartaric acid and racemic trans-1-allyl-2,5-dimethylpiperazine to give 869 g (50%).

The total of 1695 g of salt was divided into three batches and each batch was recrystallized twice in the following fashion. The salt was dissolved in refluxing 95% ethanol (~2.7 L/100 g of salt), and approximately half of the ethanol was removed by distillation. (Note: vigorous stirring was necessary during distillation to prevent crystallization on the vessel wall.) The hot solution was seeded with crystals of the pure diastereomeric salt, cooled to room temperature, and stirred slowly for 2 days before collecting the salt by filtration. (Note: a subsequent experiment suggested that crystallization time can be reduced from 2 days to 8 hours.) The total amount recovered was 1151 g. The salt was dissolved in 3 L of 2 M aqueous sodium hydroxide, and the aqueous solution was extracted with four 1 L portions of dichloromethane. The organic extracts were combined, dried over sodium sulfate, and solvent removed by rotary evaporation (temperature <20° C.) to give 293 g (29% based on racemic weight) of (2R,5S)-1-allyl-2,5-dimethylpiperazine as a clear oil. $[α]_D^{20}$=−55.1 (abs. ethanol, c=1.2). The trifluoroacetamide of the product was prepared with trifluoroacetic anhydride and analyzed by chiral capillary gas chromatography (Chiraldex B-PH column, 20 m×0.32 mm, Advanced Separation Technologies Inc., Whippany, N.J., 120° C.) indicating an enantiopurity of >99% ee (retention time of desired enantiomer, 11.7 min; other enantiomer, 10.7 min).

3-Phenoxy-tert-butyldimethylsilane magnesium bromide was formed by the slow addition of 2.7 M n-butyllithium in heptane (150 mL, 405 mmol) to a solution of 3-bromophenoxy-tert-butyldimethylsilane (123.44 g, 429 mmol) in 500 mL anhydrous tetrahydrofuran at −70° C. After stirring 45 min. this cold solution was siphoned under nitrogen into a slurry of magnesium bromide etherate (110.62 g, 428 mmol) in 650 mL anhydrous tetrahydrofuran at room temperature, and stirred for 45 min.

Thiophene-3-carboxaldehyde (29.09 g, 259 mmol), benzotriazole (30.91 g, 259 mmol), and (2R,5S)-1-allyl-2,5-trans-dimethylpiperazine (40.01 g, 259 mmol) were dissolved in 250 mL toluene and heated to a gentle reflux. The water-toluene azeotrope was collected in a Dean-Stark trap over the course of 2.5 hours. The remaining solvent was removed under vacuum. The residue was dissolved in 150 mL anhydrous tetrahydrofuran and added to a solution of 3-phenoxy-tert-butyldimethylsilane magnesium bromide in anhydrous tetrahydrofuran (1150 mL, 0.35 M) under a nitrogen atmosphere.

The reaction was stirred at room temperature for 2 hours and then quenched by the addition of 25 mL saturated NH$_4$Cl solution. Anhydrous magnesium sulfate (~5 g) and Celite (~10 g) were added. The mixture was stirred and filtered, and the solvent was removed under reduced pressure. The residue was dissolved in ethyl acetate and washed first with 0.5 N NaOH solution (5×200 mL) and then with brine (1×200 mL). The solution was dried (Na$_2$SO$_4$/MgSO$_4$) and concentrated under reduced pressure.

The dark residue was dissolved in 250 mL anhydrous acetonitrile and tetraethyl-ammonium fluoride dihydrate (72.26 g, 390 mmol) was added. After stirring for 90 min. the reaction was concentrated and the residue was dissolved in 200 mL ethyl acetate. The mixture was extracted with dilute NaHCO$_3$ solution (3×200 mL) and with water (1×200 mL). The organic layer was diluted with 200 mL diethyl ether and extracted with 10% citric acid solution (8×200 mL). The combined aqueous extracts was adjusted to pH 8.5 using 50% NaOH solution and extracted with dichloromethane (3×200 mL). The solution was dried (Na$_2$SO$_4$/MgSO$_4$) and concentrated under reduced pressure. The resulting tan solid (53.25 g, 155 mmol) was crystallized twice from 225 mL of 2:1/isopropanol:water to yield fluffy, white needle crystals (34.14 g, 99.7 mmol) of 3-((S)-((2S,5R)-4-Allyl-2,5-dimethyl-1-piperazinyl)(3-thienyl)methyl)phenol.

$^1$H NMR (500 MHz, $d_6$-DMSO): δ 9.32 (s, 1H), 7.44 (dd, J=3.2, 4.9 Hz, 1H), 7.15 (s, 1H), 7.13 (t, J=8.25 Hz, 1H), 6.98 (d, J=4.9 Hz, 1H), 6.66-6.70 (m, 3H), 5.73-5.81 (m, 1H), 5.15

(d, J=17.1 Hz, 1H), 5.09 (d, J=10.5 Hz, 1H), 5.02 (s, 1H), 3.20 (br d, J=10.2 Hz, 1H), 2.78 (dd, J=7.3, 7.5 Hz, 1H), 2.68 (dd, J=2.6, 11.3 Hz, 1H), 2.59 (dd, J=1, 9.3 Hz, 1H), 2.44 (br s, 2H), 2.02 (t, J=8.6 Hz, 1H), 1.81 (t, J=8.1 Hz, 1H), 1.09 (d, J=6 Hz, 3H), 0.91 (d, J=6 Hz, 3H). Calculated for $C_{20}H_{26}N_2OS$: C, 70.14; H, 7.65; N, 8.18; S, 9.36%. Found: C, 70.19; H, 7.58; N, 8.12; S, 9.33%.

3-((S)-((2S,5R)-4-Allyl-2,5-dimethyl-1-piperazinyl)(3-thienyl)methyl)phenol (8.56 g, 25 mmol), N-phenyltrifluoromethanesulfonimide (9.86 g, 27.6 mmol), and triethylamine (8.0 mL, 57.1 mmol) were dissolved in 75 mL dichloromethane and stirred overnight at room temperature under nitrogen. After concentrating under reduced pressure, the residue was dissolved in 150 mL ethyl acetate and washed with $Na_2CO_3$ solution (3×150 mL), water (1×100 mL), and brine (1×100 mL). The solution was dried ($Na_2SO_4$/$MgSO_4$) and concentrated under reduced pressure. The residual oil was purified by chromatography on silica gel (2% $NH_4OH$ in EtOAc/$CH_2Cl_2$) to give 11.8 g (24.8 mmol) of a viscous, light yellow oil.

The allyl portion was removed using $Pd(dba)_2$/DPPB in the presence of thiosalicylic acid by the method of Genet [J. P. Genet, S. Lemaire-Audoire, M. Savignac, Tetrahedron Letters, 36, 1267-1270 (1995)]. The reaction was concentrated and the residue was dissolved in 50 mL ethyl acetate and 100 mL diethyl ether. After washing this with $Na_2CO_3$ solution (3×150 mL) and water (1×100 mL), the organic solution was extracted with 3 N HCl (2×20 mL) and 1 N HCl (2×20 mL). The acidic extract was adjusted to pH 8.5 using NaOH solution and extracted with dichloromethane (3×50 mL). The solution was dried ($Na_2SO_4$/$MgSO_4$) and concentrated under reduced pressure. The residual oil was purified by chromatography on silica gel (2% $NH_4OH$ in EtOAc/$CH_2Cl_2$) to give 8.83 g (20.3 mmol) of a viscous, light amber oil.

The above free amine (1.09 g, 2.5 mmol) was combined with anhydrous sodium carbonate powder (1.50 g, 14.1 mmol), 10 mL anhydrous acetonitrile, and benzyl bromide (0.33 mL, 2.75 mmol). The reaction was stirred overnight at room temperature under nitrogen, and then concentrated under reduced pressure. The residue was suspended in 15 mL ethanol, 10 mL of 10% NaOH solution was added, and the reaction was stirred for 1 hour. The ethanol was removed under vacuum and the residue was partitioned between water and dichloromethane. The solution was adjusted to pH 8.5 using 3 N HCl, separated and extracted again with dichloromethane (2×25 mL). The solution was dried ($Na_2SO_4$/$MgSO_4$) and concentrated under reduced pressure. The residual oil was purified by chromatography on silica gel (2% $NH_4OH$ in EtOAc/$CH_2Cl_2$) to give 0.81 g (1.93 mmol) of 3-((S)-((2S,5R)-4-benzyl-2,5-dimethyl-1-piperazinyl)(3-thienyl)methyl)phenol as a white foam.

$^1$H NMR (500 MHz, $d_6$-DMSO): δ 9.33 (s, 1H), 7.45 (dd, J=3, 4.9 Hz, 1H), 7.25-7.36 (m, 4H), 7.17-7.21 (m, 2H), 7.13 (t, J=7.8 Hz, 1H), 6.99 (d, J=4.9 Hz, 1H), 6.66-6.71 (m, 3H), 5.00 (s, 1H), 3.81 (d, J=13.2 Hz, 1H), 3.15 (d, J=12.9 Hz, 1H), 2.65 (dd, J=2.6, 11.2 Hz, 1H), 2.58 (dd, J=2.4, 11 Hz, 1H), 2.42 (br s, 1H), 1.86-1.94 (m, 2H), 1.02 (d, J=5.7 Hz, 3H), 1.01 (d, J=5.7 Hz, 3H). MS: 393 (M+1, 100%), 189 (32%). Calculated for $C_{24}H_{28}N_2OS.0.3C_4H_8O$: C, 72.24; H, 7.31; N, 6.69; S, 7.65%. Found: C, 72.23; H, 7.24; N, 6.74; S, 7.74%.

This material was converted to the hydrochloride salt and precipitated from $CH_2Cl_2$/$Et_2O$ as an amorphous, white solid. Calculated for $C_{24}H_{28}N_2OS.0.3C_4H_{10}O.1.3HCl$: C, 65.49; H, 7.04; N, 6.06; S, 6.94; Cl, 9.97%. Found: C, 65.70; H, 7.34; N, 6.09; S, 6.97; Cl, 9.95%.

EXAMPLE 25

3-((S)-((2S,5R)-4-(2,6-Difluorobenzyl)-2,5-dimethyl-1-piperazinyl)(3-thienyl) methyl)phenol The compound of this Example was prepared by following the synthesis procedure as described in Example 24 using 2,6-difluorobenzyl bromide.

The free base was obtained as an off-white foam in 84% yield from 3-((S)-((2S,5R)-4-Allyl-2,5-dimethyl-1-piperazinyl)(3-thienyl)methyl)phenol.

$^1$H NMR (500 MHz, $d_6$-DMSO): δ 9.31 (s, 1H); 7.45 (dd, J=3.0, 4.9 Hz, 1H); 7.35-7.38 (m, 1H); 7.13 (s, 1H); 7.12 (t, J=7.7 Hz, 1H); 7.05 (t, J=7.8 Hz, 1H); 7.02-7.07 (m, 1H); 6.96 (d, J=4.9 Hz, 1H); 6.66 (br d, J=8.0 Hz, 2H); 6.64 (br s, 1H); 5.02 (s, 1H); 3.83 (d, J=12.6 Hz, 1H); 3.26 (d, J=7.4 Hz, 1H); 2.58-2.62 (m, 2H); 2.50 (m, 1H-obscured by DMSO peak); 2.45 (m, 1H); 2.32 (m, 1H); 1.97 (t, J=9.2 Hz, 1H); 1.77 (m, 1H); 1.05 (d, J=6.0 Hz, 3H); 1.01 (d, J=6.0 Hz, 3H).

This material was converted to the hydrochloride salt and precipitated from $CH_2Cl_2$/$Et_2O$ as an amorphous, off-white solid. Calculated for $C_{24}H_{26}F_2N_2OS.0.1C_4H_{10}O.0.6H_2O.1.05$ HCl: C, 60.43; H, 6.07; N, 5.78; S, 6.61; Cl, 7.68%. Found: C, 60.33; H, 6.02; N, 5.71; S, 6.46; Cl, 7.55%. MS: 429 (M+1, 100%), 189 (11%).

EXAMPLE 26

(+)-3-((R)-((2S,5R)-4-Allyl-2,5-dimethyl-1-piperazinyl)-3-hydroxybenzyl)-N-(3-fluorophenyl)-N-methylbenzamide 3-Fluoro-N-methylaniline was prepared from 3-fluoroaniline using a modified reductive amination. First, 1-hydroxymethylbenzotriazole was prepared by adding 37% aqueous formaldehyde to benzotriazole at 40° C. in a 1:1 ratio and cooling to room temperature to precipitate the product. After filtration the hydroxymethylbenzotriazole (125 g) was heated to reflux in toluene with 3-fluoroaniline (92.2 g). Water was removed azeotropically using a Dean-Stark trap. After three hours, the mixture was cooled to room temperature, then refrigerated for several hours to complete precipitation. The white crystalline solid was collected by filtration, yielding 174.2 g (86.6%) of 1-((3-fluoroanilino)methyl)-1H-benzotriazole.

1-((3-Fluoroanilino)methyl)-1H-benzotriazole (173.9 g) was slurried in dry tetrahydrofuran. Sodium borohydride (32.5 g) was added portionwise to the mixture at room temperature. After addition was complete, the mixture was heated at reflux for 4 hours. The solution was cooled and poured slowly into 400 mL of 5 M hydrochloric acid with ice and stirred for 1 hour at room temperature. The solution pH was adjusted to 9-10 using 10 M sodium hydroxide solution. The product was extracted using diethyl ether. The ether extracts were washed successively with 1 M sodium hydroxide solution, saturated sodium chloride solution, and water. The organic phase was dried over sodium sulfate and evaporated under reduced pressure to yield 87.5 g (97%) of 3-fluoro-N-methylaniline as a colorless oil. [NMR (200 MHz, DMSO-$d_6$): δ 2.76 (s, 3H); 3.41 (br s, 1H); 6.59-6.92 (m, 3H); 7.27 (q, J=8.0 Hz, 1H)].

3-Carboxybenzaldehyde was slurried in thionyl chloride (6 mL). A reflux condenser fitted with a calcium chloride drying tube was placed on the flask. The reaction was placed in an oil bath and heated at a bath temperature maintained below 100° C. The mixture was allowed to reflux until a clear solution was obtained and for 5-10 additional minutes before cooling to room temperature. The solution was diluted with anhydrous toluene, and all volatiles were removed under vacuum.

The crude acid chloride was dissolved in dichloromethane and cooled in an ice/water bath. Triethylamine (6 mL) was added dropwise via an addition funnel, followed by N-methyl-3-fluoroaniline (1.83 g) in dichloromethane. The cloudy solution was allowed to warm to room temperature over 1 hour. Water was added and the product was extracted with dichloromethane. The organic layer was washed with water and saturated sodium chloride solution and dried over sodium sulfate, and the solvent was removed under vacuum. N-(3-Fluorophenyl)-3-formyl-N-methylbenzamide (3.20 g) was obtained as a light golden oil (93% unchromatographed yield). [NMR (300 MHz, DMSO-$d_6$): δ 3.38 (s, 3H); 6.94-7.02 (m, 2H); 7.18-7.29 (m, 2H); 7.46 (t, J=7.7 Hz, 1H) 7.55 (d, J=7.6 Hz, 1H); 7.81 (m, 2H); 9.90 (s, 1H)].

2R,5S-1-Allyl-2,5-dimethylpiperazine (as prepared in Example 1, 1.28 g, 8.3 mMol.), benzotriazole (1.00 g, 8.4 mMol, 1.01 eq., Aldrich), and N-(3-fluorophenyl)-3-formyl-N-methylbenzamide (2.14 g, 8.3 mMol.) were mixed in 80 mL of dry toluene with one drop of triethylamine. The mixture was placed in an oil bath maintained below 140° C. (bath temperature. The flask was attached to a Dean-Stark trap and reflux condenser to allow the azeotropic removal of water. The mixture was refluxed for 2-3 hours, under a nitrogen atmosphere, then the majority of the toluene was removed under reduced pressure. The crude adduct was used in the following procedure without isolation.

The crude benzotriazole adduct was dissolved in ~10 mL of tetrahydrofuran and added to a solution of 3-phenoxy-tert-butyldimethylsilane magnesium bromide (as prepared in Example 17, 1.75 equiv.) via a double-ended needle. After stirring under nitrogen at room temperature for 2 hours, the reaction was quenched with 3-4 mL of saturated ammonium chloride solution. Having stirred this for about half an hour, a generous amount of anhydrous magnesium sulfate was added. Filtering and concentrating the solution under reduced pressure gave the crude silyl ether contaminated with benzotriazole by-product. This residue was dissolved in ethyl acetate and extracted with 10% aqueous NaOH solution three times to remove most of the benzotriazole. The organic layer was washed with saturated sodium chloride solution, dried over sodium sulfate/magnesium sulfate, and the ethyl acetate was removed under reduced pressure.

The t-butyldimethylsilyl protecting group was removed by dissolving the residue in 40 mL of tetrahydrofuran and adding 40 mL of 3N aqueous HCl at room temperature. The solution warmed upon acid addition. The mixture was stirred for 90 minutes at room temperature. The reaction was concentrated under reduced pressure to remove most of the organic solvent. The residue was partitioned between water and a solution of diethyl ether:ethyl acetate/3:2. The acidic aqueous layer was extracted twice with a solution of diethyl ether ethyl acetate/3:2.

The aqueous layer was adjusted to pH=2 using aqueous NaOH solution, at which point cloudiness persisted and a dark oil began to precipitate. Methylene chloride (~100 mL) was added and stirred briskly. This was separated and the aqueous layer was again washed with more methylene chloride. The combined organic extract was partitioned with water, and while stirring vigorously was adjusted to pH=9 using aqueous NaOH solution. This was then separated and the aqueous layer was again washed with more methylene chloride.

The combined extract was dried over sodium sulfate/magnesium sulfate, and the solvent was evaporated under reduced pressure. The crude material was chromatographed on silica gel column (roughly 20-25 g of silica gel per gram of crude material) eluting first with methylene chloride, then with 20% ethyl acetate in methylene chloride to remove the less polar contaminant. Then, the column was eluted with a solution of ethyl acetate containing 2% ammonium hydroxide (solution A) in a gradient with methylene chloride (solution B), quickly increasing in polarity from 25% to 100% (solution A in B).

The desired fractions were combined and the solvent was removed under reduced pressure. A 10:1 mixture of diastereomers (approx. 2.6 g) was obtained. Pure product was obtained by crystallization from a hot solution of ethyl acetate (5-10 mL) followed by slow addition of heptane (10-20 mL) and gradual cooling to give 1.78 g of (+)-3-((αR)-α-((2S,5R)-4-allyl-2,5-dimethyl-1-piperazinyl)-3-hydroxybenzyl)-N-(3-fluorophenyl)-N-methylbenzamide as an off-white crystalline solid (m.p.=144-145° C.) with >98% isomeric purity (as determined by NMR). NMR (200 MHz, DMSO-$d_6$): δ 0.84 (d, J=6.0 Hz, 3H); 0.97 (d, J=5.9 Hz, 3H); 1.69 (dd, $J_1$=7.7 Hz, $J_2$=10.7 Hz, 1H); 2.01 (dd, $J_1$=7.4 Hz, $J_2$=10.7 Hz, 1H); 2.28 (br. d, J=8.3 Hz, 1H); 2.40-2.52 (m, 2H); 2.67 (br d, J=10.5 Hz, 1H); 2.82 (dd, $J_1$=7.6 Hz, $J_2$=13.2 Hz, 1H); 3.17 (br. d, J=14.0 Hz, 1H); 3.34 (s, 3H); 4.80 (s, 1H); 5.10 (d, J=10.1 Hz, 1H); 5.17 (d, J=17.3 Hz, 1H); 5.70-5.84 (m, 1H); 6.42 (d, J=7.1 Hz, 1H); 6.56 (s, 1H); 6.65 (d, J=8.3 Hz, 1H); 6.90-7.32 (m, 9H); 9.31 (s, 1H). Mass spectrum (CI—$CH_4$) m/z: 488 (m+1, 100%), 334 (39%), 153 (87%). $[α]_D^{20}$=+4.9° (abs. ethanol, c=1.2).

EXAMPLE 27

3-((R)-((2S,5R)-4-Benzyl-2,5-dimethyl-1-piperazinyl)-3-hydroxybenzyl)-N-(3-fluorophenyl)-N-methylbenzamide 3-((R)-((2S,5R)-4-Allyl-2,5-dimethyl-1-piperazinyl)-3-hydroxybenzyl)-N-(3-fluoro phenyl)-N-methylbenzamide (Example 26, 4.88 g, 10 mmol), N-phenyltrifluoromethanesulfonimide (3.82 g, 10.7 mmol), and triethylamine (3.1 mL, 22 mmol) were dissolved in 75 mL dichloromethane and stirred overnight at room temperature under nitrogen. After concentrating under reduced pressure, the residue was dissolved in 100 mL ethyl acetate and washed with $Na_2CO_3$ solution (3×100 mL), water (1×100 mL), and brine (1×100 mL). The solution was dried ($Na_2SO_4$/$MgSO_4$) and concentrated under reduced pressure. The residual oil was purified by chromatography on silica gel (2% $NH_4OH$ in EtOAc/$CH_2Cl_2$) to give 6.1 g (9.8 mmol) of a viscous, golden yellow oil.

The allyl portion was removed using $Pd(dba)_2$/DPPB in the presence of thiosalicylic acid by the method of Genet [J. P. Genet, S. Lemaire-Audoire, M. Savignac, Tetrahedron Letters, 36, 1267-1270 (1995)]. The reaction was concentrated and the residue was dissolved in 50 mL ethyl acetate and 100 mL diethyl ether. After washing this with $Na_2CO_3$ solution (3×100 mL) and water (1×100 mL), the organic solution was extracted with 3 N HCl (3×20 mL) and 1 N HCl (1×20 mL). The acidic extract was adjusted to pH 8.5 using NaOH solution and extracted with dichloromethane (3×25 mL). The solution was dried ($Na_2SO_4$/$MgSO_4$) and concentrated under reduced pressure. The residual oil was purified by chromatography on silica gel (2% $NH_4OH$ in EtOAc/$CH_2Cl_2$) to give 4.44 g (7.6 mmol) of a viscous, deep amber-orange colored oil.

The above free amine (0.867 g, 1.5 mmol) was combined with anhydrous sodium carbonate powder (0.81 g, 7.64 mmol), 10 mL anhydrous acetonitrile, and benzyl bromide (0.20 mL, 1.68 mmol). The reaction was stirred overnight at room temperature under nitrogen, and then concentrated under reduced pressure. The residue was suspended in 15 mL ethanol, 10 mL of 10% NaOH solution was added, and the reaction was stirred for 30 minutes. The ethanol was removed under vacuum and the residue was partitioned between water and dichloromethane. The solution was adjusted to pH 8.5 using 3 N HCl, separated and extracted again with dichloromethane (2×25 mL). The solution was dried ($Na_2SO_4$/$MgSO_4$) and concentrated under reduced pressure. The residual oil was purified by chromatography on silica gel (2% $NH_4OH$ in $EtOAc/CH_2Cl_2$) to give 0.44 g (0.82 mmol) of the desired product as a white foam.

$^1H$ NMR (500 MHz, $d_6$-DMSO): δ 9.32 (s, 1H), 7.19-7.30 (m, 10H), 7.05-7.09 (m, 2H), 6.98 (dt, J=2.3, 8.4 Hz, 1H), 6.89 (dd, J=1.0, 8.0 Hz, 1H), 6.63 (dd, J=1.0, 8.0 Hz, 1H), 6.57 (br s, 1H), 6.43 (d, J=7.4 Hz, 1H), 4.77 (br s, 1H), 3.77 (d, J=13.7 Hz, 1H), 3.36 (s, 3H), 3.21 (d, J=13.7 Hz, 1H), 2.59 (d, J=9.0 Hz, 1H), 2.50 (m, 2H-obscured by DMSO peak), 2.35 (d, J=9.0 Hz, 1H), 1.92 (dd, J=7.4, 10.9 Hz, 1H), 1.74 (dd, J=7.4, 10.9 Hz, 1H), 0.99 (d, J=6.1 Hz, 3H), 0.92 (d, J=6.1 Hz, 3H). MS: 538 (M+1, 100%), 334 (20%). Calculated for $C_{34}H_{36}FN_3O_2.0.15C_4H_8O_2.0.06CH_2Cl_2$: C, 74.88; H, 6.77; N, 7.56; F, 3.42%. Found: C, 74.72; H, 6.96; N, 7.38; F, 3.79%.

This material was converted to the hydrochloride salt and precipitated from $CH_2Cl_2/Et_2O$ as an amorphous, off-white solid. Calculated for $C_{34}H_{36}FN_3O_2.0.1C_4H_{10}O.1.1HCl.0.1H_2O$: C, 70.39; H, 6.58; N, 7.16; Cl, 6.64%. Found: C, 70.41; H, 6.56; N, 7.13; Cl, 6.60%.

EXAMPLE 28

3-((R)-((2S,5R)-2,5-Dimethyl-4-(4-fluorobenzyl)-1-piperazinyl)-3-hydroxybenzyl)-N-(3-fluoro-phenyl)-N-methylbenzamide The compound of this Example was prepared by following the synthesis procedure as described in Example 27 using 4-fluorobenzyl bromide.

The free base was obtained as an off-white foam in 58% yield from 3-((R)-((2S,5R)-4-Allyl-2,5-dimethyl-1-piperazinyl)-3-hydroxybenzyl)-N-(3-fluorophenyl)-N-methylbenzamide.

$^1H$ NMR (600 MHz, $d_6$-DMSO): δ 9.29 (s, 1H), 7.16-7.29 (m, 7H), 7.02-7.10 (m, 4H), 6.97 (dt, J=2.3, 8.4 Hz, 1H), 6.88 (dd, J=1.2, 8.0 Hz, 1H), 6.61 (dd, J=1.2, 8.0 Hz, 1H), 6.55 (br s, 1H), 6.42 (br d, J=7.3 Hz, 1H), 4.74 (br s, 1H), 3.71 (br d, J=13.0 Hz, 1H), 3.34 (s, 3H), 3.19 (br d, J=13.0 Hz, 1H), 2.56 (d, J=9.0 Hz, 1H), 2.48 (m, 2H-obscured by DMSO peak), 2.32 (d, J=9.0 Hz, 1H), 1.90 (dd, J=7.2, 11.1 Hz, 1H), 1.72 (dd, J=7.2, 11.1 Hz, 1H), 0.97 (d, J=6.1 Hz, 3H), 0.90 (d, J=6.1 Hz, 3H). MS: 556 (M+1, 100%), 334 (26%).

This material was converted to the hydrochloride salt and precipitated from $CH_2Cl_2/Et_2O$ as an amorphous, off-white solid. Calculated for $C_{34}H_{35}F_2N_3O_2.0.5H_2O.0.95HCl$: C, 68.14; H, 6.21; N, 7.01; Cl, 5.62%. Found: C, 68.17; H, 6.27; N, 6.91; Cl, 5.63%.

EXAMPLE 29

4-((alpha-R)-alpha-((2S,5R)-2,5-Dimethyl-4-(4-fluorobenzyl)-1-piperazinyl)-3-methoxybenzyl)-N,N-diethylbenzamide Sodium hydride (60% dispersion in oil, 400 mg (240 mg NaH, 10 mmol)) was washed with pentane (2×7 mL), and tetrahydrofuran (10 mL) was added. The product from Example 11, 4-((alpha-R)-alpha-((2S,5R)-2,5-dimethyl-4-(4-fluorobenzyl)-1-piperazinyl)-3-hydroxybenzyl)-N,N-diethylbenzamide (1.007 g, 2.0 mmol) was dissolved in the stirred suspension, and when effervescence had subsided, methyl iodide (249 μL, 568 mg, 4 mmol) was added. The reaction mixture was sealed under nitrogen and stirred for 6 h at ambient temperature. The reaction mixture was evaporated to dryness, and the residue was partitioned between ethyl acetate (15 mL) and water (5 mL). The organic layer was separated, the aqueous portion extracted with ethyl acetate (2×10 mL) and the combined organic extracts were dried over anhydrous sodium sulfate. The organic solution was evaporated to a pale yellow gum, which on trituration and sonication with pentane yielded 4-((alpha-R)-alpha-((2S,5R)-2,5-dimethyl-4-(4-fluorobenzyl)-1-piperazinyl)-3-methoxybenzyl)-N,N-diethylbenzamide as a flocculent white solid (0.798 g, 77% after drying at room temperature and 5 mm Hg). Calc. for $C_{32}H_{40}FN_3O_2.0.25H_2O$: C, 73.60; H, 7.82; N, 8.05; F, 3.64. Found C, 73.58; H, 7.70; N, 8.04; F, 3.84%. $^1H$ NMR (CDCl3, 300 MHz): δ 1.09 (d, J=6.2 Hz, 6H, superimposed on br m, 3H); 1.21 (br m, 3H); 1.99 (m, 2H); 2.57 (br m, 2H); 2.66 (m, 3H); 3.15 (d, J=13.3 Hz, 1H); 3.27 (br m, 2H); 3.54 (br m, 2H); 3.78 (s, 3H); 3.84 (d, J=13 Hz, 1H); 5.10 (s, 1H); 6.76 (s, 1H); 6.70 (d, J=8.1 Hz, 2H); 6.96 (t, J=8.2 Hz, 2H); 7.26 (m, 5H); 7.46 (d, J=7.8 Hz, 2H).

EXAMPLE 30

N,N-Diethyl-3-[(R)-[(2S,5R)-4-(3-hydroxybenzyl)-2,5-dimethylpiperazin-1-yl](3-methoxyphenyl)methyl]benzamide The title compound was made in identical fashion to the compound of Example 17, with the exception that 3-methoxyphenyl magnesium bromide was substituted for 3-(tert-butyldimethylsilyloxy)phenyl magnesium bromide.

Calc. for $C_{32}H_{41}N_3O_3.HCl$: C, 66.98; H, 7.75; N, 7.32; Cl, 6.80. Found: C, 66.92; H, 7.64; N, 7.21; Cl, 6.61.

EXAMPLE 31

N,N-Diethyl-3-{(R)-(3-hydroxyphenyl)-[(2S,5R)-4-(3-methoxybenzyl)-2,5-dimethylpiperazin-1-yl]methyl}benzamide The title compound was made in identical fashion to the compound of Example 17, with the exception that 3-methoxybenzaldehyde was substituted for 3-hydroxybenzaldehyde.

Calc. for $C_{32}H_{41}N_3O_3.HCl.H_2O$: C, 67.41; H, 7.78; N, 7.37; Cl, 6.22. Found: C, 66.80; H, 7.73; N, 7.21; Cl, 6.63.

EXAMPLE 32

(3-{(2R,5S)-4-[(R)-(3-Diethylcarbamoylphenyl)-(3-hydroxyphenyl)methyl]-2,5-dimethylpiperazin-1-ylmethyl}phenoxy)acetic acid 3-Hydroxybenzaldehyde (2.00 g, 16.4 mmol) was dissolved in 25 mL of dry tetrahydrofuran under nitrogen with 3.5 g of potassium carbonate and 3.01 g (18.0 mmol) of ethyl bromoacetate. The reaction was heated at reflux for 6 hr, then cooled to room temperature and filtered from inorganic salts. The filtrate was evaporated, redissolved in 30 mL of methylene chloride, washed with 2×15 mL of water, and dried over sodium sulfate. Evaporation of solvent gave 2.92 of ethyl 3-formylphenoxyacetate as a yellow oil.

3-((alpha-R)-alpha-((2S,5R)-2,5-Dimethyl-1-piperazinyl)-3-trifluoromethyl-sulfonyloxybenzyl)-N,N-diethylbenzamide (0.79 g, 1.5 mmol, as made in Example 17) and ethyl 3-formylphenoxyacetate (0.62 g, 3.0 mmol) were placed in a 50 mL flask and sealed under nitrogen with 15 mL of tetrahydrofuran and 100 mg of acetic acid. The solution was stirred at room temperature for 20 minutes, and then sodium triacetoxyborohydride (0.96 g, 4.00 mmol) was added and the reaction was stirred overnight. The reaction mixture was diluted with 100 mL of ethyl acetate, washed with aqueous sodium carbonate and brine, and dried over anhydrous sodium sulfate. Evaporation of solvent gave 1.2 g of yellow oil. The crude diester was purified by chromatography on silica gel with 20% ethyl acetate in methylene chloride to give 0.56 g of ethyl (3-{(2R,5S)-4-[(R)-(3-diethylcarbamoylphenyl)-(3-trifluoromethylsulfonyloxyphenyl)methyl]-2,5-dimethylpiperazin-1-ylmethyl}phenoxy)acetate. The product was dissolved in 8 mL of 95% ethanol with 80 mg of sodium hydroxide and stirred overnight. The ethanol was evaporated and the aqueous solution was extracted with 2×2 mL of 1:1 diethyl ether/ethyl acetate. Dilute hydrochloric acid was added dropwise to the aqueous layer to give maximum precipitate, which was collected by filtration. The collected yellow solid was triturated with a mixture of diethyl ether (4 mL), methanol (4 mL), hexane (2 mL), and ethyl acetate (1.5 mL) and filtered. The remaining solid was collected by filtration and dissolved in 5 mL of methylene chloride. Diethyl ether was added with stirring to precipitate the product, which was collected by filtration and dried to give 277 mg of (3-{(2R,5S)-4-[(R)-(3-diethylcarbamoylphenyl)-(3-hydroxyphenyl)-methyl]-2,5-dimethylpiperazin-1-ylmethyl}phenoxy)acetic acid as a white solid. Calc. for $C_{33}H_{41}N_3O_5 \cdot 1.4CH_2Cl_2$: C, 60.89; H, 6.51; N, 6.19. Found: C, 60.98; H, 6.56; N, 6.23.

EXAMPLE 33

(3-{(2R,5S)-4-[(R)-(3-Diethylcarbamoylphenyl)-(3-methoxyphenyl)methyl]-2,5-dimethylpiperazin-1-ylmethyl}phenoxy)acetic acid The title compound was made from the compound of Example 30 by alkylating with methyl chloroacetate according to the procedure of Example 14.

Calc. for $C_{34}H_{43}N_3O_5 \cdot 0.65 CH_2Cl_2$: C, 66.17; H, 7.10; N, 6.68. Found: C, 66.15; H, 7.49; N, 6.51.

EXAMPLE 34

N,N-Diethyl-3-[(R)-[(2S,5R)-4-(3-methoxybenzyl)-2,5-dimethylpiperazin-1-yl](3-methoxyphenyl)methyl]benzamide The title compound was made in identical fashion to the compound of Example 17 by substituting 3-methoxyphenyl magnesium bromide for 3-(tert-butyldimethylsilyloxy)phenyl magnesium bromide and by substituting 3-methoxybenzaldehyde for 3-hydroxybenzaldehyde.

Calc. for $C_{33}H_{43}N_3O_3 \cdot 1.6HCl$: C, 67.40; H, 7.64; N, 7.15; Cl, 9.65. Found: C, 67.39; H, 7.66; N, 7.00; Cl, 9.61.

EXAMPLE 35

4-(alpha-R)-alpha-((2S,5R)-4-(Cyclopropylmethyl)-2,5-dimethyl-1-piperazinyl)-3-hydroxybenzyl)-N,N-diethylbenzamide The title compound was made from 4-((alpha-R)-alpha-((2S,5R)-2,5-dimethyl-1-piperazinyl)-3-trifluoromethylsulfonyloxybenzyl)-N,N-diethylbenzamide (Example 10) by an essentially identical procedure as Example 11, using cyclopropylmethyl bromide as the alkylating agent.

Calc. for $C_{33}H_{43}N_3O_3 \cdot 0.75H_2O$: C, 72.61; H, 8.81; N, 9.07. Found: C, 72.50; H, 8.56; N, 8.68.

EXAMPLE 36

4-((alpha-R)-alpha-((2S,5R)-2,5-Dimethyl-4-(3-fluorobenzyl)-1-piperazinyl)-3-hydroxybenzyl)-N,N-diethylbenzamide A solution of 4-((alpha-R)-alpha-((2S,5R)-2,5-dimethyl-1-piperazinyl)-3-trifluoromethyl-sulfonyloxybenzyl)-N,N-diethylbenzamide (3.522 g, 6.0 mmol, Example 10) and sodium iodide (90 mg, 0.6 mmol) in acetonitrile (30 mL) was stirred during the addition of triethylamine (3.0 mL, 2.186 g, 21.6 mmol) followed by 3-fluorobenzyl bromide (1.472 mL, 2.268 g, 12.0 mmol). An immediate turbidity was observed, thickening to a white crystalline precipitate as the reaction progressed. The reaction mixture was sealed under nitrogen and stirred at room temperature. After 18 h the solvent was removed by evaporation under reduced pressure and the residue partitioned between ethyl acetate (30 mL) and saturated sodium bicarbonate solution (10 mL). The organic layer was separated and the aqueous portion further extracted with ethyl acetate (3×15 mL). The combined extract and washings were dried over sodium sulfate, the solution evaporated to dryness and re-dissolved in ethyl acetate (~5 mL). The solution was applied to an intermediate (4×15 cm) Biotage column and eluted with ethyl acetate, collecting fractions of 20 mL. Fractions containing pure material as evidenced by thin layer chromatography (silica, EM60F$_{254}$, developed with ethyl acetate, R$_f$ 0.9) were pooled and evaporated to yield a yellow/orange oil (3.01 g). The oil was dissolved in ethanol (30 mL) and aqueous sodium hydroxide solution (10.0 mL, 2.5-M, 25 mmol) was added. The initially cloudy suspension clarified to a yellow solution that was set aside at room temperature for 3 h. The mixture was evaporated under reduced pressure to remove ethanol, and evaporation continued until condensation of water indicated complete removal of ethanol. The cloudy suspension of the oily sodium salt of the phenol was diluted to 20 mL with water to yield a clear yellow solution. The pH of the strongly basic solution was adjusted to 8.5-9 by passage of carbon dioxide gas (from dry ice) to yield a dense white flocculent precipitate. The solid was removed by filtration and washed thoroughly with cold water, including twice re-slurrying of the precipitate on the sinter with fresh water. The solid was air-dried on the sinter overnight, then dried under vacuum at 1 mm Hg at room temperature to yield 4-((alpha-R)-alpha-((2S,5R)-2,5-dimethyl-4-(3-fluorobenzyl)-1-piperazinyl)-3-hydroxybenzyl)-N,N-diethylbenzamide as a white solid (2.062 g, 67%) Calc. for $C_{31}H_{38}FN_3O_2$ 0.5 H$_2$O: C, 72.63; H, 7.67; N, 8.20; F, 3.71. Found C, 72.77; H, 7.52; N, 8.18; F, 3.61%. $^1$H NMR (CDCl3, 300 MHz); δ 1.05 (d, J=5.9 Hz, 6H); 1.11 (br m, 3H); 1.23 (br m, 3H); 2.00 (m, 2H); 2.59 (br m, 2H); 2.62 (d, J=11.4 Hz, 1H); 2.68 (d, J=11.0 Hz, 1H); 3.19 (d, J=13.6 Hz, 1H); 3.28 (br m, 2H); 3.54 (br m, 2H); 3.89 (d, J=13.9 Hz, 1H); 5.01 (s, 1H); 6.15 (v br s, 1H); 6.63 (s, 1H); 6.70 (m, 2H); 6.91 (t, J=8.8 Hz, 1H); 7.07 (m, 2H); 7.14 (t, J=7.8 Hz, 1H); 7.22 (m, 1H); 7.28 (d, J=8.2 Hz, 2H); 7.44 (d, J=8.1 Hz, 2H).

EXAMPLE 37

4-((alpha-S)-alpha-((2S,5R)-2,5-Dimethyl-4-(4-hydroxybenzyl)-1-piperazinyl)-benzyl)-N,N-diethylbenzamide 4-Hydroxybenzaldehyde (488 mg, 4.0 mmol) was dissolved in a solution of 4-((alpha-S)-alpha-((2S,5R)-2,5-dimethyl-1-piperazinyl)benzyl)-N,N-diethylbenzamide (759 mg, 2.0 mmol, Example 2) and acetic acid in tetrahydrofuran (10 mL). Sodium triacetoxy borohydride (848 mg, ~4 mmol) was added portionwise over 5 min, then the reaction mixture sealed under nitrogen and stirred overnight at room temperature. The reaction mixture was evaporated to dryness and the residue partitioned between water (6 mL) and ethyl acetate (20 mL). The aqueous solution was further extracted with ethyl acetate (2×10 mL) and the combined extract and washings diluted with an equal volume of ether. The organic solution was extracted with 3M-HCl and the acidic aqueous solution carefully neutralized, initially with 5M-NaOH, then saturated $NaHCO_3$. At pH 4 the solution was filtered through a 0.45 mM syringe filter to remove a small quantity of an off-white gummy solid. The pH of the filtrate was adjusted to 8.5 to precipitate a flocculent white solid which was filtered off, washed well with cold water and dried overnight at 2 mm Hg at room temperature to yield 4-((alpha-S)-alpha-((2S, 5R)-2,5-dimethyl-4-(4-hydroxybenzyl)-1-piperazinyl)-benzyl)-N,N-diethylbenzamide (73.05%). Calc. for $C_{31}H_{39}N_3O_2$ $1.5H_2O$ C, 72.62; H, 8.26; N, 8.20. Found C, 72.58; H, 7.83; N, 8.40%. $^1H$ NMR (1% NaOD in D2O, 300 MHz); δ 0.75 (br m, 3H); 0.81 (br d, J=7.3 Hz, 6H); 0.94 (br m, 3H); 1.71 (m, 1H); 1.84 (m, 1H); 2.29 (m, 2H); 2.49 (br m, 2H); 2.91 (m, 3H); 3.22 (m, 2H); 3.57 (br m, 2H); 5.02 (s, 1H); 6.39 (d, J=7.5 Hz, 2H); 6.80 (d, J=7.3 Hz, 2H); 7.01 (m, 7H); 7.17 (m, 2H).

EXAMPLE 38

4-(alpha-R)-alpha-((2S,5R)-4-Benzyl-2,5-dimethyl-1-piperazinyl)-3-methoxybenzyl)-N,N-diethylbenzamide Alkylation of 4-((alpha-R)-alpha-((2S,5R)-4-benzyl-2,5-dimethyl-1-piperazinyl)-3-hydroxybenzyl)-N,N-diethylbenzamide (Example 12) with methyl iodide according to the procedure of Example 29 gave the title compound.
Calc. for $C_{32}H_{41}N_3O_2$: C, 76.92; H, 8.27; N, 8.41. Found: C, 76.84; H, 8.34; N, 8.29.

EXAMPLE 39

4-((alpha-R)-alpha-((2S,5R)-2,5-Dimethyl-4-(2-fluorobenzyl)-1-piperazinyl)-3-methoxybenzyl)-N,N-diethylbenzamide 4-((alpha-R)-alpha-((2S,5R)-2,5-Dimethyl-1-piperazinyl)-3-trifluoromethylsulfonyloxy-benzyl)-N,N-diethylbenzamide (from Example 10, 527.6 mg, 1.0 mmol) was dissolved in acetonitrile (4.0 mL) and sodium iodide (15 mg, 0.1 mmol) added. The suspension was stirred during the addition of triethylamine (500 μL (363 mg), 3.59 mmol), followed by 2-fluorobenzyl bromide (241 μL (378 mg), 2.0 mmol). The reaction mixture was sealed under nitrogen and stirred overnight at room temperature. The reaction mixture was evaporated to dryness and partitioned between ethyl acetate (10 mL) and saturated aqueous sodium bicarbonate solution (2.5 mL). The supernatant organic layer was removed, and the aqueous portion washed with ethyl acetate (3×10 mL). The combined organic extract and washings were dried over anhydrous sodium sulfate and evaporated to a golden oil. The residue was dissolved in ethyl acetate (7 mL), applied to a pre-packed (Biotage) column and eluted with ethyl acetate. Pure fractions containing desired product, as evidenced by t.l.c. (silica gel, $EM60F_{264}$, 100% ethyl acetate, $R_f$=0.77) were evaporated to dryness to yield the intermediate 4-((alpha-R)-alpha-((2S,5R)-2,5-Dimethyl-4-(2-fluorobenzyl)-1-piperazinyl)-3-trifluoromethylsulfonyloxybenzyl)-N,N-diethylbenzamide (610 mg), as a yellow oil which was used without further purification. The oil was dissolved in ethanol (7 mL) and aqueous 2.5 M (10%) sodium hydroxide solution (5 mL, 12.5 mmol) was added. The reaction mixture was set aside at room temperature for 5 h, then the ethanol removed by evaporation. The oily suspension of the sodium salt was clarified by the addition of water (5 mL), and the pH of the solution adjusted to 9-10 by the passage of gaseous carbon dioxide (from dry ice). The copious white precipitate was washed well with water and dried under vacuum (2 mm Hg) at room temperature overnight to yield 4-((alpha-R)-alpha-((2S,5R)-2,5-dimethyl-4-(2-fluorobenzyl)-1-piperazinyl)-3-hydroxybenzyl)-N,N-diethylbenzamide as a white solid (431 mg, 85.6%). Calc. for $C_{31}H_{38}FN_3O_2$: C, 73.93; H, 7.61; N, 8.34; F, 3.77. Found C, 73.96; H, 7.67; N, 8.29; F, 3.75%. $^1H$ NMR (CDCl3, 300 MHz); δ 1.05 (d, J=6.1 Hz, 3H); 1.09 (d, J=6 Hz, 3H); 1.12 (br m, 3H); 1.24 (br m, 3H); 1.96 (t, J=10 Hz, 1H); 2.07 (t, J=10 Hz, 1H); 2.56 (br m, 2H); 2.60 (d, J=11 Hz, 1H); 2.72 (d, J=11 Hz, 1H); 3.29 (br m, 2H); 3.36 (d, J=14 Hz, 1H); 3.55 (br m, 2H); 3.89 (d, J=14 Hz, 1H); 5.13 (s, 1H); 6.57 (s, 1H); 6.66 (d, J=10 Hz, 2H); 7.00 (t, J=9 Hz, 1H); 7.07 (t, J=7.5 Hz, 1H); 7.10 (t, J=8 Hz, 1H); 7.20 (m, 1H); 7.27 (d, J=8 Hz, 2H); 7.38 (t, J=7 Hz, 1H); 7.43 (d, J=7 Hz, 2H).
4-((alpha-R)-alpha-((2S,5R)-2,5-dimethyl-4-(2-fluorobenzyl)-1-piperazinyl)-3-hydroxybenzyl)-N,N-diethylbenzamide was alkylated with methyl iodide by a procedure essentially identical to that of Example 29 to give 4-((alpha-R)-alpha-((2S,5R)-2,5-dimethyl-4-(2-fluorobenzyl)-1-piperazinyl)-3-methoxybenzyl)-N,N-diethylbenzamide.
Calc. for $C_{32}H_{40}FN_3O_2.0.1 H_2O$: C, 73.99; H, 7.80; N, 8.09; F, 3.66. Found: C, 73.98; H, 7.86; N, 8.00; F, 3.77.

EXAMPLE 40

4-[(R)-((2R,5S)-4-Allyl-2,5-dimethylpiperazin-1-yl)(3-hydroxyphenyl)methyl]-N,N-dimethylbenzenesulfonamide 3-(t-Butyl-dimethylsilanyloxy)benzaldehyde t-Butyldimethylchlorosilane (26.01 g; 172.56 mmol) was added to a solution of 3-hydroxybenzaldehyde (20.7 g; 164.35 mmol) and imidazole (27.97 g; 410.9 mmol) in chloroform (300 mL) under nitrogen at 0° C. The reaction was allowed to warm to room temperature and stirred overnight. The reaction mixture was washed with water (100 mL×3) and brine (100 mL), dried over anhydrous sodium sulfate and concentrated to give crude product (29.56 g), which was purified by column chromatography on silica gel eluting with (i) pentane and (ii) 3% ethyl acetate in pentane to give 3-(t-butyl-dimethylsilanyloxy)benzaldehyde (21.0 g; 54%). $^1H$ NMR (300 MHz, $CDCl_3$) δ 9.93 (s, 1H), 7.45 (d, 1H, J=7.5 Hz), 7.38 (dd, 1H, J=7.5, 7.5 Hz), 7.31 (d, 1H, J=1.0 Hz), 7.09 (1H, dd, J=7.5, 1.0 Hz), 0.98 (s, 9H), 0.20 (s, 6H).

4-Iodo-N,N-dimethyl-benzenesulfonamide

Dimethylamine (100 mL of 2.0 M solution in tetrahydrofuran; 200 mmol) was added to a solution of 4-iodobenzenesulfonyl chloride (54.76 g; 181 mmol) in pyridine (300 mL) at 0° C. under $N_2$, followed by the addition of 4-N,N-dimethylaminopyridine (15 mg). The reaction was allowed to warm to room temperature and was stirred under $N_2$ for 48 hrs. The reaction solution was poured into 1.2 liter of water, and the precipitated product was collected by filtration and rinsed with water (300 mL×2). The solid was dissolved in ethyl acetate (500 mL) and washed with 5% aqueous hydrochloric acid (300 mL×3), water (300 mL×2) and brine (300 mL). The organic solution was dried over anhydrous sodium sulfate and concentrated to give 4-iodo-N,N-dimethyl-benzenesulfonamide (49.46 g; 88%) as a white solid, which was used in the next reaction without further purification. $^1$H NMR (300 MHz, CDCl$_3$) δ 7.88 (d, 2H, J=8.5 Hz), 7.46 (d, 2H, J=8.5 Hz), 2.69 (s, 3H).

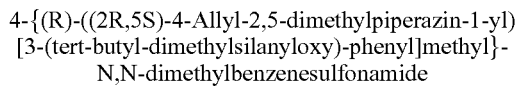

4-{(R)-((2R,5S)-4-Allyl-2,5-dimethylpiperazin-1-yl) [3-(tert-butyl-dimethylsilanyloxy)-phenyl]methyl}-N,N-dimethylbenzenesulfonamide Part 1: Preparation of Iminium Intermediate:

To a 3-neck flask equipped with a Soxhlet extractor filled with 3 A molecular sieves was added benzotriazole (618 mg; 5.19 mmol), 3-(t-butyl-dimethylsilanyloxy)benzaldehyde (1.227 g; 5.19 mmol), (+)-(2S,5R)-1-allyl-2,5-dimethylpiperazine (961 mg; 6.23 mmol, prepared by the method described in Example 1 for (−)-(2R,5S)-1-allyl-2,5-dimethylpiperazine, but using di-p-toluoyl-L-tartaric acid as the resolving agent) and toluene (150 mL). The solution was refluxed under N$_2$ for 20 h. The solution was cooled to room temperature under N$_2$.

Part 2: Preparation of Grignard Reagent:

Isopropylmagnesium chloride (6.91 mL of 2.0 M solution in tetrahydrofuran; 13.82 mmol) was added to a solution of 4-iodo-N,N-dimethylbenzenesulfonamide (4.3 g; 13.82 mmol) at room temperature under N$_2$ and stirred for 20 minutes.

Part 3:

The solution of Part 1 was added to the Grignard reagent prepared in Part 2 dropwise via a syringe at room temperature under N$_2$ in a span of 35 minutes while the reaction solution was stirred vigorously. The reaction was stirred at room temperature overnight and quenched by the addition of saturated aqueous ammonium chloride (10 mL). The resulting mixture was diluted by the addition of ethyl acetate (120 mL) and water (120 mL). The cloudy mixture was filtered thru a Celite® pad. The filtrate was poured into a separate funnel. The organic layer and water layer were separated. The organic layer was extracted with 10% aqueous sodium hydroxide (75 mL×4), washed with water (100 mL×3) and brine (100 mL), dried (sodium sulfate) and concentrated to give crude product, which was purified by silica gel chromatography conducted on CombiFlash™ Sq 16× (gradient: 100% CH$_2$Cl$_2$ to 7% MeOH in CH$_2$Cl$_2$) to give 4-{(R)-((2R,5S)-4-allyl-2,5-dimethylpiperazin-1-yl)[3-(tert-butyl-dimethylsilanyloxy)-phenyl]methyl}-N,N-dimethylbenzenesulfonamide (1.3 g; 45%). $^1$H NMR (300 MHz, CDCl$_3$) δ 7.71 (d, 2H, J=8.0 Hz), 7.35 (d, 2H, J=8.0 Hz), 7.12 (dd, 1H, J=8.0, 8.0 Hz), 6.92 (s, 1H), 6.84 (d, 1H, J=8.0 Hz), 6.71 (d, 1H, J=8.0 Hz), 5.82 (1H, m), 5.23-5.11 (m, 3H), 3.35 (dd, 1H, J=14.0, 5.5 Hz), 2.88 (dd, 1H, J=14.0, 8.0 Hz), 2.82 (dd, 1H, J=11.0, 3.0 Hz), 2.73 (s, 6H), 2.68 (dd, 1H, J=11.0, 2.5 Hz), 2.55 (m, 2H), 2.16 (dd, 1H, J=11.0, 8.5 Hz), 1.85 (dd, 1H, J=11.0, 9.0 Hz), 1.18 (d, 3H, J=6.0 Hz), 1.01 (d, 3H, J=6.0 Hz), 0.96 (s, 9H), 0.17 (s, 3H), 0.16 (s, 3H).

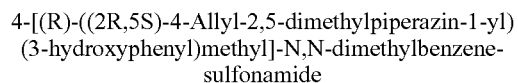

4-[(R)-((2R,5S)-4-Allyl-2,5-dimethylpiperazin-1-yl) (3-hydroxyphenyl)methyl]-N,N-dimethylbenzenesulfonamide 3 N HCl (7 mL) was added to the solution of 4-{(R)-((2R, 5S)-4-allyl-2,5-dimethylpiperazin-1-yl)[3-(tert-butyl-dimethylsilanyloxy)-phenyl]methyl}-N,N-dimethylbenzenesulfonamide (1.3 g) in tetrahydrofuran (15 mL). The mixture was stirred at room temperature overnight. Water (15 mL) was added to the reaction. The reaction mixture was extracted with diethyl ether (25 mL×3). The remaining water layer was neutralized by 10% aqueous NaOH to pH=8-9 and then extracted with ethyl acetate (30 mL×3). The combined ethyl acetate layers were washed with water (20 mL×3) and brine (20 mL), dried over sodium sulfate and concentrated to give 0.83 g of crude product. The crude product was purified by silica gel chromatography conducted on CombiFlash™ Sq 16× (gradient: 100% CH$_2$Cl$_2$ to 7% MeOH in CH$_2$Cl$_2$) to give 4-[(R)-((2R,5S)-4-allyl-2,5-dimethylpiperazin-1-yl)(3-hydroxyphenyl)methyl]-N,N-dimethylbenzenesulfonamide (720 mg; 70%). $^1$H NMR (300 MHz, CDCl$_3$) δ 7.71 (d, 2H, J=8.5 Hz), 7.35 (d, 2H, J=8.5 Hz), 7.14 (dd, 1H, J=8.0, 8.0 Hz), 6.89 (bs, 1H), 6.85 (d, 1H, J=8.0 Hz), 6.68 (d, 1H, J=8.0, 2.5 Hz), 5.83 (1H, m), 5.24-5.12 (m, 3H), 3.32 (dd, 1H, J=13.5, 5.0 Hz), 2.86 (dd, 1H, J=13.5, 8.0 Hz), 2.78 (dd, 1H, J=11.5, 3.0 Hz), 2.72 (s, 6H), 2.65 (dd, 1H, J=11.0, 2.5 Hz), 2.51 (m, 2H), 2.14 (dd, 1H, J=11.5, 9.0 Hz), 1.81 (dd, 1H, J=11.0, 9.5 Hz), 1.16 (d, 3H, J=6.0 Hz), 0.98 (d, 3H, J=6.0 Hz); MS (FAB, glycerol) m/z: 444 (M$^+$+H), 290, 153. Found: C, 58.32; H, 6.66; N, 8.18. Calc. (C$_{24}$H$_{33}$N$_3$O$_3$S 0.8 CH$_2$Cl$_2$): C, 58.23; H, 6.82; N, 8.21.

EXAMPLE 41

4-((alpha-S)-alpha-((2R,5S)-2,5-Dimethyl-4-(3-fluorobenzyl)-1-piperazinyl)benzyl)-N,N-diethylbenzamide 4-Carboxybenzaldehyde (100 g, 666 mmol) was added to a 2000 mL, 3-necked, round bottom flask and stirred under nitrogen in 1200 mL of toluene. Thionyl chloride (53.5 mL, 733 mmol) was added to the mixture, followed by the addition of 0.15 mL of dimethylformamide. A reflux condenser fitted with a calcium chloride drying tube was placed on the flask. The reaction was placed in an oil bath and heated at a bath temperature maintained at 120° C. The mixture was allowed to reflux for 1 hour after a clear solution was obtained and then cooled to room temperature. The solution was diluted with anhydrous toluene, and all volatiles were removed under vacuum.

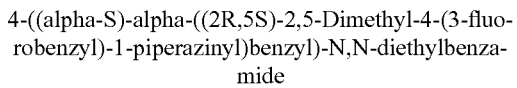

The crude acid chloride was dissolved in 1500 mL of dry tetrahydrofuran and cooled in an ice/water bath. Diethylamine (173 mL, 1.67 mol, 2.5 equivalents) was added dropwise via an addition funnel. The cloudy solution was allowed to warm to room temperature over 1 hour and stirred overnight. The reaction mixture was filtered to remove the white crystalline diethylamine hydrochloride by-product. The crystals were washed with ethyl acetate (2×600 mL). The tetrahydrofuran filtrate was evaporated, and the residue was dissolved in the ethyl acetate washings. The solution was washed sequentially with 1 M hydrochloric acid (2×600 mL), water (2×300 mL), dilute sodium carbonate solution (saturated: H$_2$O, 1:1, 2×600 mL), water (2×300 mL) and saturated sodium chloride solution (300 mL). The organic layer was separated, dried over sodium sulfate, and the solvent was removed under vacuum. 4-formyl-N,N-diethylbenzamide (117.14 g) was obtained as a light yellow oil which was used without further purification (85% crude yield). $^1$H NMR (300 MHz, CDCl$_3$): δ 1.09-1.25 (m, 6H); 3.19-3.31 (d, J=6.4 Hz, 2H); 3.54-3.56 (d, J=6.6 Hz, 2H); 7.49-7.52 (d, J=8.1 Hz, 2H); 7.89-7.92 (d, J=8.2 Hz, 2H); 9.98 (s, 1H).

Phenylmagnesium bromide (1.0 M solution in tetrahydrofuran, 235 mL, 235 mmol) was slowly added to a flask containing a cold (−78° C.) solution of 4-formyl-N,N-diethylbenzamide (48.18 g, 235 mmol) in 500 mL of dry tetrahydrofuran under nitrogen. The transfer rate was monitored to maintain reaction temperature below −70° C. The reaction was stirred for another 45 minutes at −78° C. and then quenched with 45 mL of saturated aqueous ammonium chloride. After warming to room temperature, the mixture was diluted with 900 mL of diethyl ether and washed with 900 mL of water followed by 230 mL of saturated sodium chloride. The ethereal solution was dried over sodium sulfate and the solvent removed to give crude 4-(N,N-diethylcarbamoyl)benzhydryl alcohol as a light yellow oil. Crude yield was ~92%.

The 4-(N,N-diethylcarbamoyl)benzhydryl alcohol (61.35 g, 216.5 mmol) was dissolved in 1500 mL of dichloromethane and 23.69 mL (324.8 mmol) of thionyl chloride was added dropwise. The reaction solution was stirred overnight at room temperature and the solvent was removed under vacuum. The crude product was redissolved in 800 mL of toluene and the solvent again was removed under vacuum to eliminate excess thionyl chloride, providing crude 4-(N,N-diethylcarbamoyl)benzhydryl chloride as a dark oil. Crude yield=100%.

The crude 4-(N,N-diethylcarbamoyl)benzhydryl chloride (125 mmol) was dissolved in acetonitrile (300 mL). Sodium iodide (18.64 g, 125 mmol), diisopropylethylamine (32.65 mL, 187 mmol), and (+)-(2S,5R)-1-allyl-2,5-dimethylpiperazine (19.23 g, 125 mmol, prepared by the method described in Example 1 for (−)-(2R,5S)-1-allyl-2,5-dimethylpiperazine, but using di-p-toluoyl-L-tartaric acid as the resolving agent) were added. The mixture was stirred at reflux, under nitrogen, for 3 hours. The acetonitrile was removed under reduced pressure, the reaction mixture was poured into ethyl acetate (500 mL) and potassium carbonate solution (150 mL of a 2M aqueous solution), and shaken. The organic phase was separated, washed with water and brine, dried over solid potassium carbonate, and concentrated in vacuo to give 55.35 g (100% crude yield) of 4-((αR and αS)-α-((2R,5S)-4-allyl-2,5-dimethyl-1-piperazinyl)benzyl)-N,N-diethylbenzamide as a 1:1 mixture of isomers, epimeric at the benzhydryl carbon.

The allyl portion was removed using Pd(dba)$_2$/DPPB in the presence of thiosalicylic acid by the method of Genet [J. P. Genet, S. Lemaire-Audoire, M. Savignac, Tetrahedron Letters, 36, 1267-1270 (1995)]. The reaction was concentrated and the residue was dissolved in 300 mL ethyl acetate and 600 mL diethyl ether. After washing with Na$_2$CO$_3$ solution (3×300 mL) and water (1×300 mL), the organic solution was diluted with pentane (1500 mL) and extracted with 3 M HCl (5×80 mL) and 1 M HCl (3×100 mL), alternating with water (3×100 mL). The combined aqueous extracts were filtered to remove a small amount of suspended solid and the pH was adjusted to 12 using 5M NaOH solution. The resulting oily suspension was extracted with dichloromethane (3×300 mL). The combined organic solution was dried (Na$_2$SO$_4$/MgSO$_4$) and concentrated under reduced pressure to give 4-((αR and αS)-α-((2R,5S)-2,5-dimethyl-1-piperazinyl)benzyl)-N,N-diethylbenzamide as a pale yellow solid (27.11 g, 71.43 mmol).

A solution of 4-((αR and αS)-α-((2R,5S)-2,5-dimethyl-1-piperazinyl)benzyl)-N,N-diethylbenzamide (27.11 g, 71.43 mmol) in acetonitrile (450 mL) was added to sodium iodide (1.07 g, 7.14 mmol) and stirred under nitrogen at room temperature during the addition of triethylamine (35.84 mL, 26.02 g, 257 mmol), followed by 3-fluorobenzyl bromide (17.52 mL, 143 mmol). An immediate turbidity was observed on addition of the fluorobenzyl bromide. The reaction mixture was stirred under nitrogen overnight at room temperature. The solvent was removed by evaporation and the residue was partitioned between 300 mL methylene chloride and 300 mL saturated sodium bicarbonate solution, followed by extraction with another 2×300 mL of methylene chloride. The combined organic extracts were washed with water (2×300 mL), and brine (300 mL), dried over Na$_2$SO$_4$/MgSO$_4$ and concentrated under reduced pressure. The residual deep-red oil was purified by chromatography on silica gel (12% EtOAc in CH$_2$Cl$_2$) to give 5.83 g (11.96 mmol) of 4-((αS)-α-((2R,5S)-2,5-dimethyl-4-(3-fluorobenzyl)-1-piperazinyl)benzyl)-N,N-diethylbenzamide as a light yellow solid. The benzhydryl epimer, 4-((αR)-α-((2S,5R)-2,5-dimethyl-4-(3-fluorobenzyl)-1-piperazinyl)benzyl)-N,N-diethylbenzamide (5.46 g) and 11.25 g of the epimer mixture were also obtained. $^1$H NMR (300 MHz, CDCl$_3$): δ 1.06-1.28 (m, 12H); 1.95-2.07 (m, 2H); 2.59-2.72 (m, 4H); 3.22-3.55 (m, 5H); 3.81-3.86 (d, J=13.6 Hz, 1H); 5.11 (s, 1H); 6.87-6.88 (t, 1H); 7.03-7.44 (m, 12H). Calculated for C$_{31}$H$_{38}$FN$_3$O.0.20EtOAc: C, 75.59; H, 7.90; N, 8.32; F, 3.76. Found: C, 75.53; H, 7.82; N, 8.45; F, 3.69. HPLC: 91.85% by Ace C-18 (3μ), initial 60% 0.01M NH$_4$OAc in MeOH: gradient to 100% MeOH, 60 min: isocratic MeOH 5 min. 0.7 ml/min: λ$_{obs}$=210 nm, R$_t$=63.4 min for title compound. The benzhydryl R epimer has R$_t$=62 min.

EXAMPLE 42

(+)-3-((αR)-α-((2S,5R)-4-Allyl-2,5-dimethyl-1-piperazinyl)-3-hydroxybenzyl)benzoic acid (+)-3-((R)-((2S,5R)-4-Allyl-2,5-dimethyl-1-piperazinyl)-3-hydroxybenzyl)-N-(3-fluorophenyl)-N-methylbenzamide (Example 26) was dissolved in 95% ethanol containing 6% by weight of sodium hydroxide and heated at reflux for 24 hours. The mixture was concentrated in vacuo to remove ethanol. The residue was dissolved in water and the resulting solution was adjusted to pH 5 with concentrated hydrochloric acid. The solvent was removed in vacuo to give 3-((αR)-α-((2S,5R)-4-allyl-2,5-dimethyl-1-piperazinyl)-3-hydroxybenzyl)benzoic acid as a mixture with sodium chloride. The crude acid was stirred with a small volume of water and filtered. The solid in the filter was washed with water and dried under vacuum to give (+)-3-((αR)-α-((2S,5R)-4-allyl-2,5-dimethyl-1-piperazinyl)-3-hydroxybenzyl)benzoic acid as a light beige solid. NMR (DMSO-d$_6$, 200 MHz) δ: 0.95 (d, J=6 Hz, 3H); 1.1 (d, J=6 Hz, 3H); 1.9 (ddd, J$_1$=3 Hz, J$_2$=7 Hz, J$_3$=10 Hz, 1H); 2.1 (dd, J$_1$=8 Hz, J$_2$=10 Hz, 1H); 2.5 (m, 2H); 2.7-2.9 (m, 2H); 3.2 (m, 2H); 5.05 (d, J=12 Hz, 1H); 5.2 (d, J=18 Hz, 1H); 5.8 (m, 1H); 6.7 (m, 3H); 7.1 (t, J=8 Hz, 1H); 7.4 (t, J=8 Hz, 1H); 7.65 (d, J=8 Hz, 1H); 7.8 (d, J=8 Hz, 1H); 8.0 (s, 1H); 9.4 (s, 1H). [α]$_D^{20}$=+4.1° (0.1 M aqueous sodium hydroxide, c=1.09). Calc. for C$_{23}$H$_{28}$N$_2$O$_3$ 0.75 H$_2$O: C, 70.12; H, 7.55; N, 7.11. Found: C, 70.23; H, 7.35; N, 7.10. Mass spectrum (CI—CH$_4$) m/e: 381 (M+1, 35%); 380 (M, 2%); 227 (28%); 155 (100%); 153 (83%).

The following Examples 43-45 may be made by methods analogous to those described in the preceding Examples.

EXAMPLE 43

(3-{(R)-(3-Diethylcarbamoylphenyl)-[(2S,5R)-4-(3-hydroxybenzyl)-2,5-dimethylpiperazin-1-yl]methyl}-phenoxy)acetic acid

EXAMPLE 44

(3-{(R)-(3-Diethylcarbamoylphenyl)-[(2S,5R)-4-(3-methoxybenzyl)-2,5-dimethylpiperazin-1-yl]methyl}-phenoxy)acetic acid

EXAMPLE 45

(3-{(2R,5S)-4-[(R)-(3-Carboxymethoxyphenyl)-(3-diethylcarbamoylphenyl)methyl]-2,5-dimethylpiperazin-1-ylmethyl}phenoxy)acetic acid

EXAMPLE 46

To investigate the efficacy of delta opioid receptor agonists as a treatment for premature ejaculation, intact conscious male mice were electrically stimulated subsequent to the administration of a delta opioid receptor agonist to determine if a delay in ejaculation was observed when compared to administration of a placebo
General Materials and Methods Male, CD-1 mice (20-30 g) were housed in groups of ten (10) in Plexiglas® chambers with food and water available before any procedure. Animals were maintained on a 12 hour light/dark cycle in a temperature-controlled animal colony. Studies were carried out in accordance with the Guide for the Care and Use of Laboratory animals as adopted and promulgated by the National Institutes of Health.

An electric bipolar rectal probe, as shown in FIG. 1, was used for stimulating the subjects. Specifically, the bipolar electrode probe is an approximately 5 cm long tube having an outer diameter of approximately 0.25 cm with an inner diameter of approximately 0.08. In the center lumen of the elongated tubular body 12 are embedded cathode 16 and anode 18, which are formed of a conductive material, preferably platinum. The cathode 16 and anode 18 are connected at one end to external power supplying means (not shown). Anode 18 extends at the other end all the way to one extremity of the elongated body 12 and forming an anode terminal 22 at such extremity. Cathode 16 only extends to a middle portion of the elongated body 12 and forming a cathode terminal 20 at such middle portion. The cathode terminal 20 is preferably positioned away from the anode terminal 22, at a distance of about 0.5 cm.

The testing delta opioid receptor agonist (SNC-80) was purchased from Tocris Cookson, Inc., Ellisville, Mo., USA, and dissolved in 5% dextrose injection solution. An equimolar amount of aqueous hydrochloric acid was added when the manufacturer packaged the compound in its base form. The placebo was 5% dextrose alone. Each mouse was injected subcutaneously with 10 mg/kg of the SNC-80 compound or with 10 mg/kg of a placebo. 10 minutes after the injection, the test mouse was subjected to electrostimulation. Ten mice were tested for each dose level, the order of each mouse receiving different doses was blinded and in a random manner.

During the testing the mouse was restrained in a cone bag with rear legs extending from the bag. Excess fecal matter was removed from the rectum and the above-discussed lubricated bipolar electrode was inserted approximately 2.5 cm into the rectum. An oscillating current of 40 Hz was utilized for electrical stimulation starting at 3 volts with a gradual increase to 8 volts by increments of 0.5 volts. The stimulation regime included 4 stimulating events for each voltage lasting 2 seconds with a rest period of 2 seconds between stimulating events until ejaculation occurred or the terminal voltage of 8 volts was reached. A white coagulum ejaculate from the penis indicates a successful ejaculation.

For the electroejaculation test, dose-response lines were constructed as an accumulated ejaculation at a specified voltage. A minimum of 10 mice was used at each dose level. Each dose response was the average of two to three independent experiments. Students' t-test was used to assess unpaired comparison, with $p<0.06$ indicating significance.

Electric stimulation was conducted on untreated mice to determine effective ejaculation parameters relating to current frequency and voltage. It was found that when 10 mice were stimulated through the voltage program starting at 3 volts with a gradual increase to 8 volts by increments of 0.5 volts, none of the mice ejaculated if the current frequency was 20 Hz. When the operating frequency increased from 30 to 70 Hz, the occurrence of successful ejaculation, which is indicated by emission of a white coagulum from the penis of the male mouse under stimulation, also increases. When the operating frequency of the electric stimulation was between 30 to 45 Hz, the ejaculation rate showed a linear dependency on the frequency. When the operating frequency reached 60 Hz, all the mice ejaculated with a 100% ejaculation rate.

Testing was conducted on mice injected with SNC-80 or a buffer vehicle for the control group. SNC-80 is a highly selective delta receptor agonist which has been found to block the contraction of mouse vas deferens smooth muscle in vitro which is one of the tissue components in the ejaculation system. Each mouse was subjected to electroejaculation at 40 Hz (starting at 3 volts with a gradual increase to 8 volts by increments of 0.5 volts) approximately 10 minutes after subcutaneous administration of SNC-80 at different doses of 0, 0.1, 0.3 and 1 mg/kg. A minimum of 10 mice were used at each dose level. Each does response was the average of two to three independent experiments ±SEM.

Figure 3:
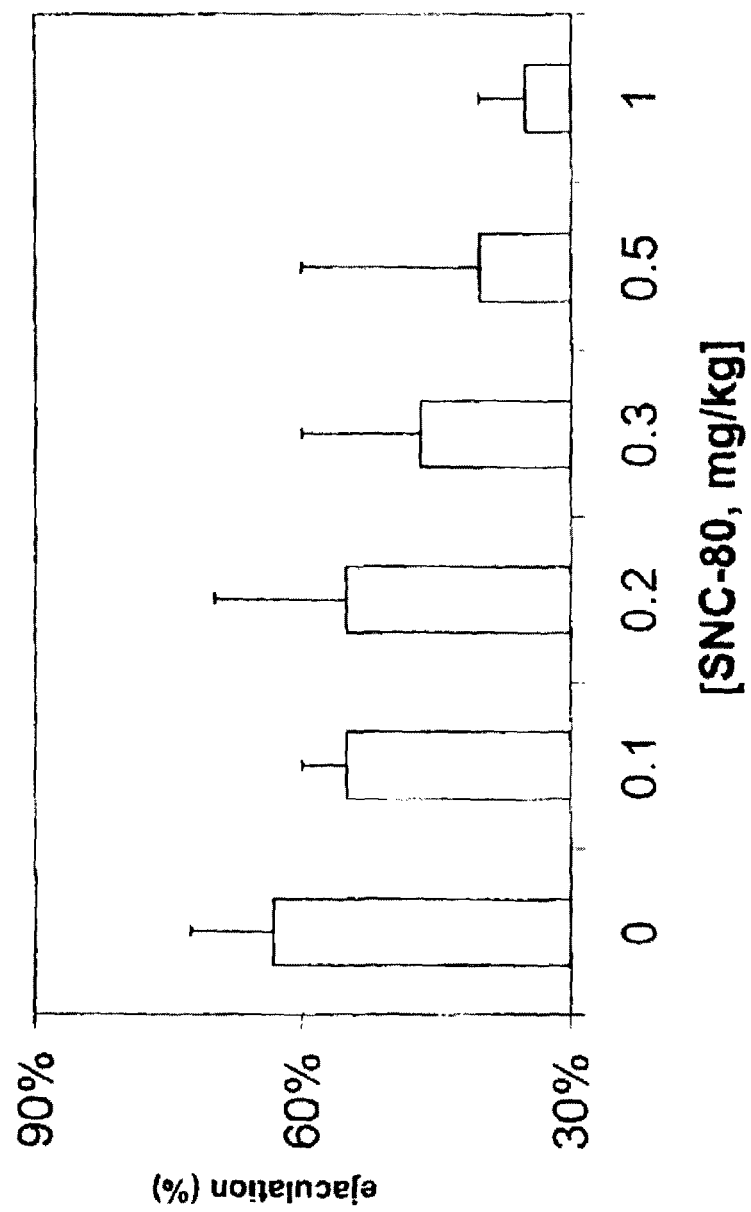
FIG. 3 illustrates the suppression effects of delta selective agonist SNC-80 in delaying electrically stimulated ejaculation.

As shown in FIG. 3, when the frequency of the electric stimulation was set at 40 Hz, a dose of 1 mg/kg of SNC-80 significantly reduced the occurrence of ejaculation in tested mice as compared to that of the control group. This reduction of ejaculation by SNC-80 is specific, as the compound works in a dose dependent manner and the inhibitory effect diminished as the concentration was reduced to 0.1 mg/kg.

EXAMPLE 47

Figure 4:
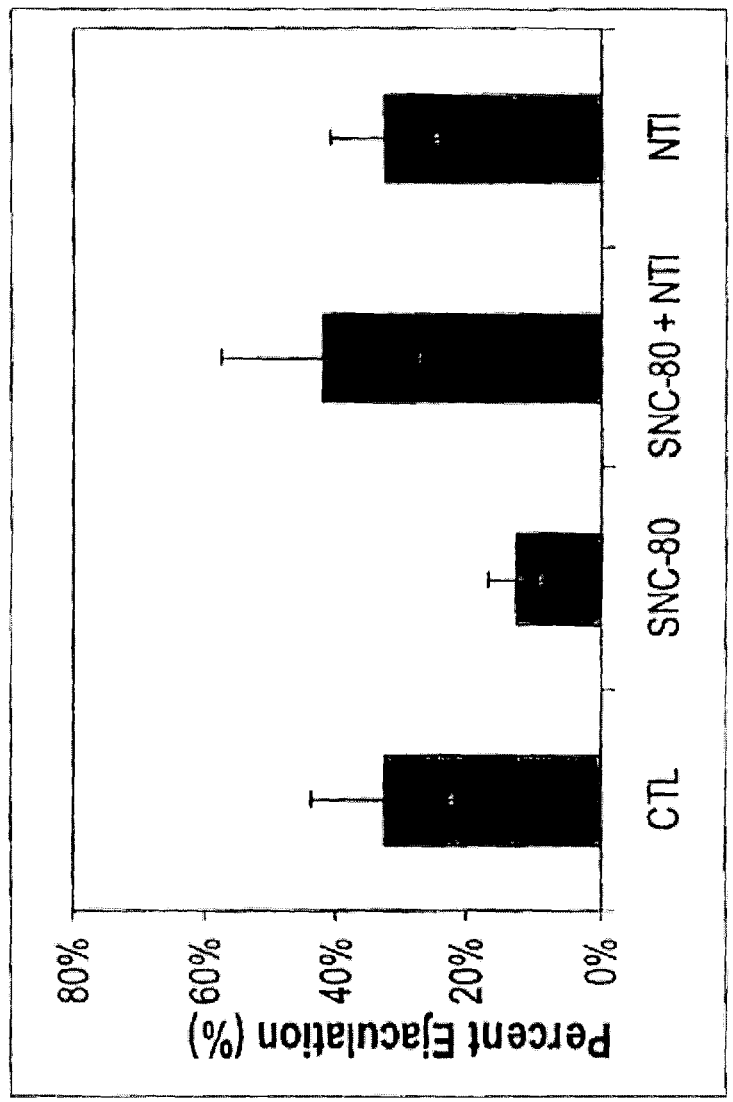
FIG. 4 illustrates that the suppression effects of SNC-80 were abolished by introduction of NTI, a delta opioid receptor antagonist.

To determine if SNC-80 inhibits the ejaculation via specific binding to delta opioid receptor, the effect of SNC-80 on ejaculation was tested against the delta opioid selective antagonist naltrindole (NTI). Subcutaneous injections of a control vehicle (CTL), 0.5 mg/kg SNC-80, 0.5 mg/kg SNC-80 plus 0.1 mg/kg of NTI and 0.1 mg/kg of NTI were administered to the mice. A minimum of 10 mice was utilized for each dose level. Each dose response is the average of two to three independent experiments ±SEM. Electroejaculation stimulation was conducted 10 minutes after injection at 35 Hz oscillating frequency, starting at 3 volts with a gradual increase to 8 volts by increments of 0.5 volts. As shown in FIG. 4, injection of 0.5 mg/kg of SNC-80 reduced the ejaculation by a factor of at least 2. However, this inhibitory effect was blocked by co-injection with 0.1 mg/kg of NTI. This result demonstrated that blocking the delta opioid receptor by NTI eliminated the effect of SNC-80 on ejaculation, indicating that activation of the delta opioid receptor reduced the electroejaculation in male mice. It is shown in FIG. 4 that injections of just NTI, without any other active ingredient, did not affect the ejaculation response.

TABLE 1

| Example | μ (nM)* | δ (nM)* | κ (nM)* | EC$_{50}$ MVD$^1$ (nM)** | Max. ejaculation Inhibition (%) | Optimal Dose$^2$ (mg/kg) |
|---|---|---|---|---|---|---|
| 11 | 27.1 | 1.23 | >100 | 2.8 | 30 | 5 |
| 12 | 1.45 | 0.123 | 68.7 | 4.4 | 28 | 5 |
| 14 | 162 | 11.1 | >100 | 7.2 | 35 | 10 |
| 13 | 3470 | 5.69 | >100 | 21.2 | 50 | 5 |
| 17 | 1.28 | 0.66 | 20.9 | 2.9 | 50 | 1 |

*Binding affinity by radio-ligand competition binding assay according to U.S. Pat. Nos. 5,985,880 and 5,807,858 the contents of which are herein incorporated by reference.
**Determined by in vitro inhibition of electrically stimulated contraction of mouse vas deferens in the tissue bath
$^1$mouse vas deferens
$^2$subcutaneous injection

EXAMPLE 48

Further evidence showing that activation of the delta opioid receptor leads to reduction in ejaculation is shown by using additional delta opioid receptor agonists that were synthesized and formulated by the inventors. Similar electroejaculation procedures were used according to Examples 46 and 47

EXAMPLE 49

Additional formulations of delta opioid receptor agonists were prepared and tested according to testing procedures set forth in Examples 46 and 47. The compounds were administered orally and the results are compiled in Table 2. The results show that the delta opioid receptor agonists had an inhibitory effect on ejaculation events of at least 33%.

TABLE 2

| Compound | Ex. No. | Effective Dose (mg/kg) | Ejaculation Inhibition % | Route of Admininstration |
|---|---|---|---|---|
| 3-((alpha-R)-alpha-((2S,5R)-4-Allyl-2,5-dimethyl-1-piperazinyl)-4-(diethyl amino-carbonyl)benzyl)phenoxyacetic acid | 14 | 0.01 | 45% | oral |
| 3-((alpha-R)-alpha-((2S,5R)-4-Benzyl-2,5-dimethyl-1-piperazinyl)-4-(diethyl aminocarbonyl)benzyl)phenoxyacetic acid | 15 | 3 | 66% | oral |
| 4-((alpha-R)-alpha-((2S,5R)-2,5-Dimethyl-4-(4-fluorobenzyl)-1-piperazinyl)-3-methoxybenzyl)-N,N-diethylbenzamide | 29 | 3 | 38% | oral |
| 4-(alpha-R)-alpha-((2S,5R)-4-(Cyclo propylmethyl)-2,5-dimethyl-1-piperazinyl)-3-hydroxybenzyl)-N,N-diethylbenzamide | 35 | 0.3 | 60% | oral |
| 4-((alpha-R)-alpha-((2S,5R)-2,5-Dimethyl-4-(3-fluorobenzyl)-1-piperazinyl)-3-hydroxybenzyl)-N,N-diethylbenzamide | 36 | 3 | 60% | oral |
| 4-((alpha-S)-alpha-((2S,5R)-2,5-Dimethyl-4-(4-hydroxybenzyl)-1-piperazinyl)-benzyl)-N,N-diethylbenzamide | 37 | 3 | 50% | oral |
| 4-(alpha-R)-alpha-((2S,5R)-4-Benzyl-2,5-dimethyl-1-piperazinyl)-3-methoxybenzyl)-N,N-diethylbenzamide | 38 | 3 | 33% | oral |
| 4-((alpha-R)-alpha-((2S,5R)-2,5-Dimethyl-4-(2-fluorobenzyl)-1-piperazinyl)-3-methoxybenzyl)-N,N-diethylbenzamide | 39 | 10 | 50% | oral |
| 4-[(R)-((2R,5S)-4-Allyl-2,5-dimethyl piperazin-1-yl)(3-hydroxyphenyl)methyl]-N,N-dimethylbenzenesulfonamide | 40 | 0.3 | 50% | oral |
| 4-((alpha-S)-alpha-((2R,5S)-2,5-Dimethyl-4-(3-fluorobenzyl)-1-piperazinyl)benzyl)-N,N-diethylbenzamide | 41 | 0.4 | 75% | oral | to determine the efficacy in delayed ejaculation. All the compounds were found to be high affinity delta opioid receptor agonists as judged by radioligand competition binding and inhibition of contraction of mouse vas defens in tissue bath. As shown in Table 1, the compounds displayed an inhibitory effect on male ejaculation. These results further elucidate an inhibitory role of delta opioid receptor activation in ejaculation.

EXAMPLE 50

Further evidence showing that activation of the delta opioid receptor leads to reduction in ejaculation can be shown by using additional delta opioid receptor agonists as set forth in Table 3 below. Similar electroejaculation procedures are used according to Examples 46 and 47 to determine the efficacy in delaying ejaculation. All the compounds have been found to be delta opioid receptor agonists, and as such, the use of the compounds results in inhibition of ejaculation in the testing subjects.

TABLE 3

| EXAMPLE NO. | STRUCTURE | NAME |
|---|---|---|
| 1 | 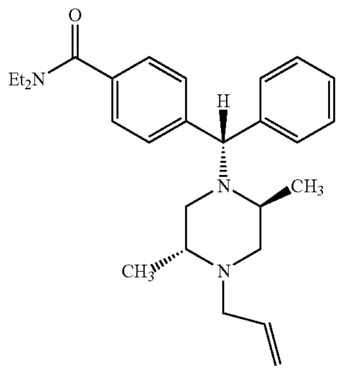 | 4-((alpha-S)-alpha-((2S,5R)-4-Allyl-2,5-dimethyl-1-piperazinyl)benzyl)-N,N-diethylbenzamide |
| 2 | 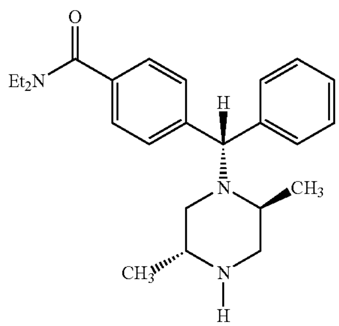 | 4-((alpha-S)-alpha-((2S,5R)-2,5-dimethyl-1-piperazinyl)benzyl)-N,N-diethylbenzamide |
| 3 | 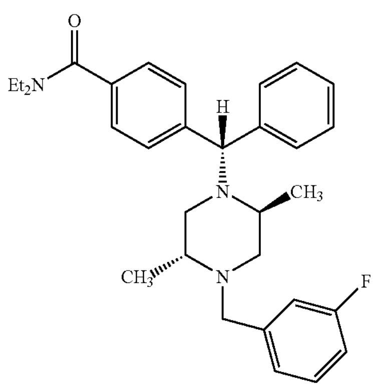 | 4-((alpha-S)-alpha-((2S,5R)-2,5-Dimethyl-4-(3-fluorobenzyl)-1-piperazinyl)benzyl)-N,N-diethylbenzamide |
| 4 | 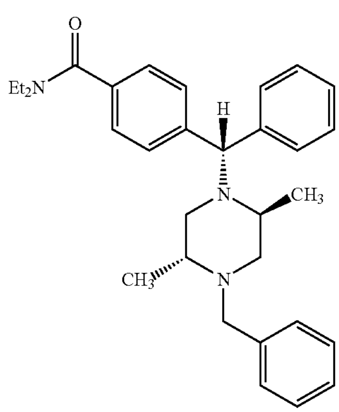 | 4-((alpha-S)-alpha-((2S,5R)-4-Benzyl-2,5-dimethyl-1-piperazinyl)benzyl)-N,N-diethylbenzamide |

TABLE 3-continued

| EXAMPLE NO. | STRUCTURE | NAME |
|---|---|---|
| 5 | 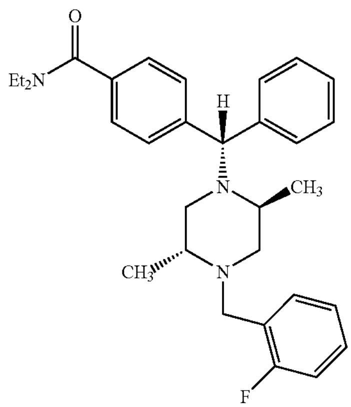 | 4-((alpha-S)-alpha-((2S,5R)-2,5-Dimethyl-4-(2-fluorobenzyl)-1-piperazinyl)benzyl)-N,N-diethylbenzamide |
| 6 | 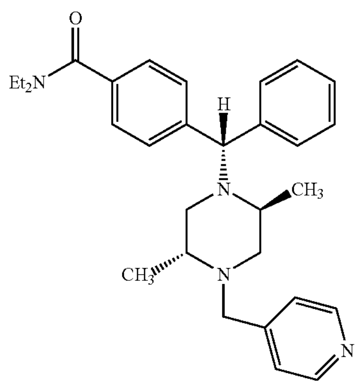 | 4-((alpha-S)-alpha-((2S,5R)-2,5-Dimethyl-4-(4-pyridylmethyl)-1-piperazinyl)benzyl)-N,N-diethylbenzamide |
| 7 | 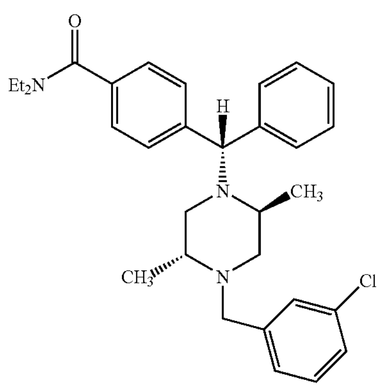 | 4-((alpha-S)-alpha-((2S,5R)-4-(3-Chlorobenzyl)-2,5-dimethyl-1-piperazinyl)benzyl)-N,N-diethylbenzamide |
| 8 | 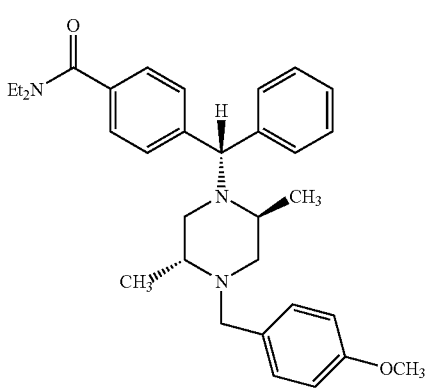 | 4-((alpha-S)-alpha-((2S,5R)-2,5-Dimethyl-4-(4-methoxybenzyl)-1-piperazinyl)benzyl)-N,N-diethylbenzamide |

TABLE 3-continued

| EXAMPLE NO. | STRUCTURE | NAME |
| --- | --- | --- |
| 16 | 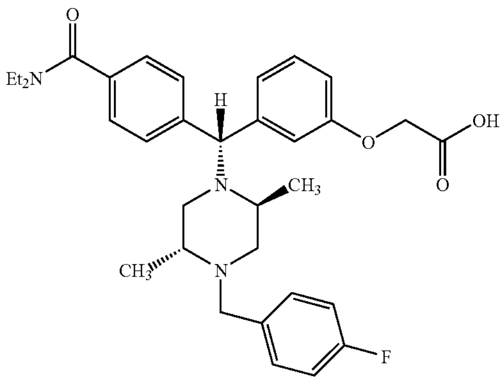 | 3-((alpha-R)-4-(Diethylaminocarbonyl)-alpha-((2S,5R)-2,5-dimethyl-4-(4-fluorobenzyl)-1-piperazinyl)benzyl)phenoxyacetic acid |
| 18 | 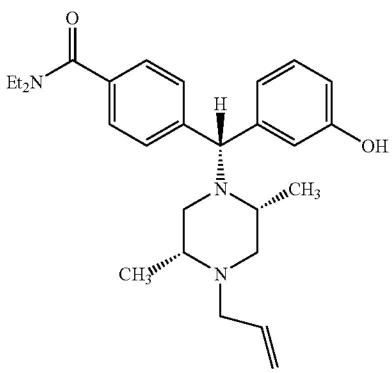 | (-)-4-(αR)-α-((2R,5R)-4-Allyl-2,5-dimethyl-1-piperazinyl)-3-hydroxybenzyl)-N,N-diethyl-benzamide |
| 19 | 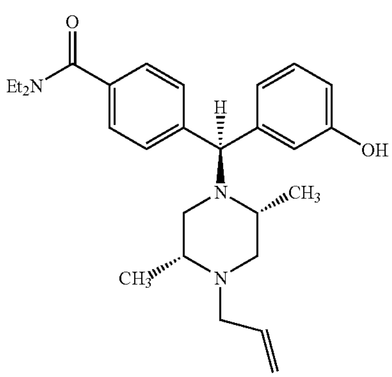 | (-)-4-(αS)-α-((2R,5R)-4-Allyl-2,5-dimethyl-1-piperazinyl)-3-hydroxybenzyl)-N,N-diethyl-benzamide |
| 20 | 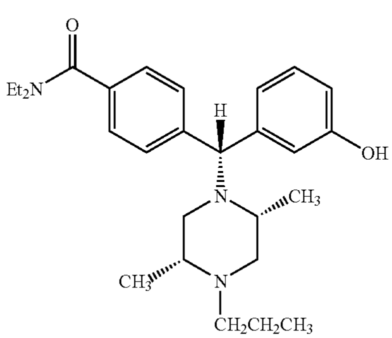 | (-)-4-((αR)-α-((2R,5R)-2,5-Dimethyl-4-propyl-1-piperazinyl)-3-hydroxybenzyl)-N,N-diethylbenzamide |

TABLE 3-continued

| EXAMPLE NO. | STRUCTURE | NAME |
| --- | --- | --- |
| 21 | 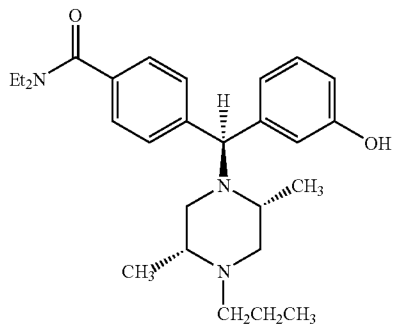 | (-)-4-(αS)-α-((2R,5R)-2,5-Dimethyl-4-propyl-piperazinyl)-3-hydroxybenzyl)-N,N-diethyl-benzamide |
| 22 | 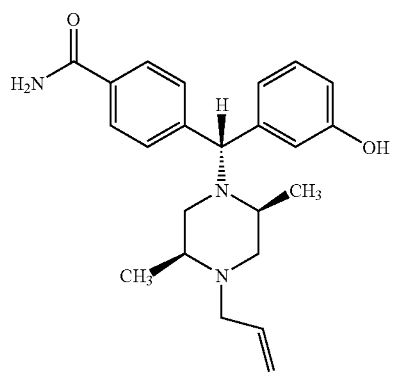 | 4-((αR)-α-(2S,5S)-4-Allyl-2,5-dimethyl-1-piperazinyl)-3-hydroxybenzyl)-benzamide |
| 23 | 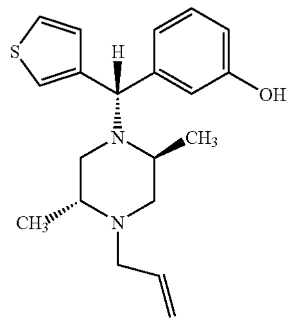 | (-)-3-((S)-((2S,5R)-4-Allyl-2,5-dimethyl-1-piperazinyl)(3-thienyl)methyl)phenol |
| 24 | 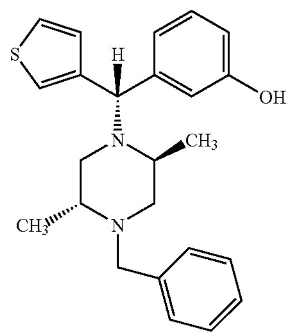 | 3-((S)-((2S,5R)-4-Benzyl-2,5-dimethyl-1-piperazinyl)(3-thienyl)methyl)phenol |

TABLE 3-continued

| EXAMPLE NO. | STRUCTURE | NAME |
|---|---|---|
| 25 | 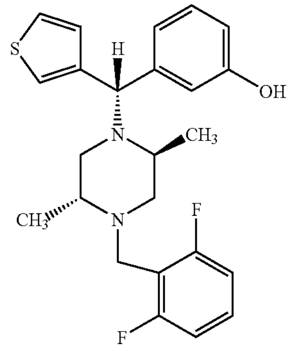 | 3-((S)-((2S,5R)-4-(2,6-Difluorobenzyl)-2,5-dimethyl-1-piperazinyl)(3-thienyl)methyl)phenol |
| 26 | 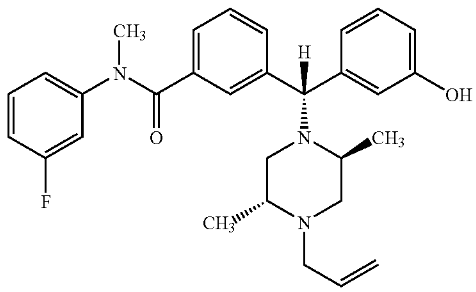 | (+)-3-((R)-((2S,5R)-4-Allyl-2,5-dimethyl-1 piperazinyl)-3-hydroxybenzyl)-N-(3-fluorophenyl)-N-methylbenzamide |
| 27 | 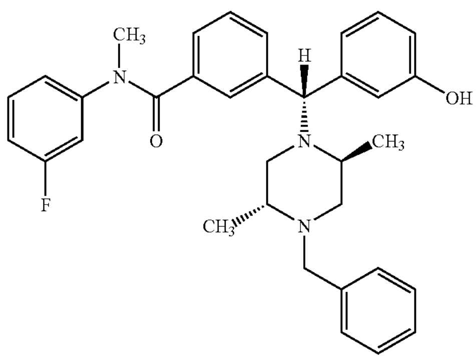 | 3-((R)-((2S,5R)-4-Benzyl-2,5-dimethyl-1-piperazinyl)-3-hydroxybenzyl)-N-(3-fluorophenyl)-N-methylbenzamide |
| 28 | 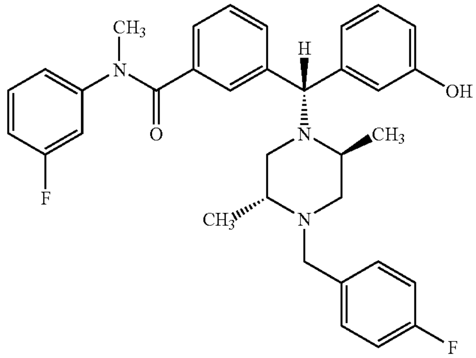 | 3-((R)-((2S,5R)-2,5-Dimethyl-4(4-fluorobenzyl)-1-piperazinyl)-3-hydroxybenzyl)-N-(3-fluorophenyl)-N-methylbenzamide |

TABLE 3-continued

| EXAMPLE NO. | STRUCTURE | NAME |
|---|---|---|
| 30 | 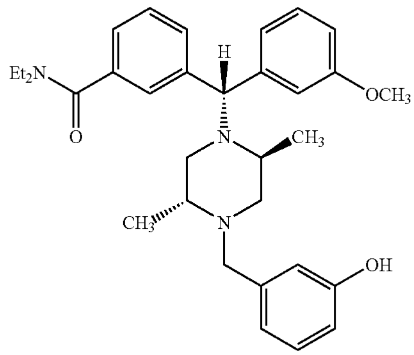 | N,N-Diethyl-3-[(R)-[2S,5R)-4-(3-hydroxybenzyl)-2,5-dimethylpiperazin-1-yl](3-methoxyphenyl)methyl]benzamide |
| 31 | 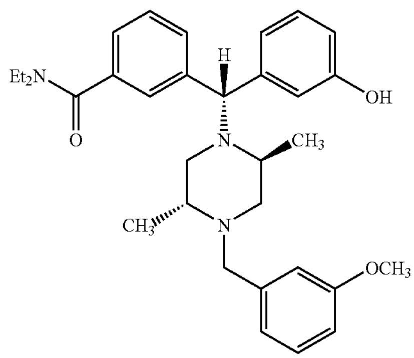 | N,N-Diethyl-3-{(R)-(3-hydroxyphenyl)-[(2S,5R)-4-(3-methoxybenzyl)-2,5-dimethylpiperazin-1-yl]methyl}benzamide |
| 32 | 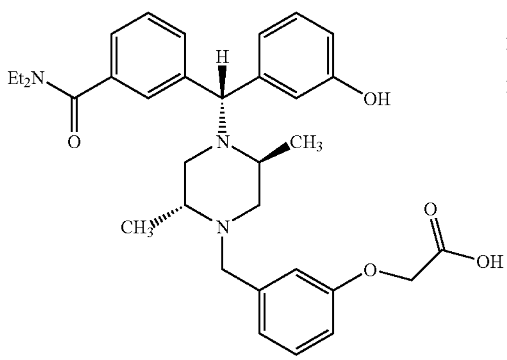 | (3-{(2R,5S)-4-[(R)-(3-Diethylcarbamoyl-phenyl)-(3-hydroxyphenyl)methyl]-2,5-dimethyl-piperazin-1-ylmethyl}-phenoxy)acetic acid |
| 33 | 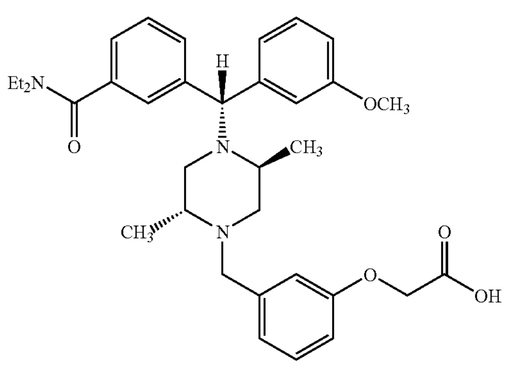 | (3-{(2R,5S)-4-[(R)-(3-Diethylcarbamoylphenyl)-(3-methoxyphenyl)methyl]-2,5-dimethylpiperazin-1-ylmethyl}phenoxy)acetic acid |

TABLE 3-continued

| EXAMPLE NO. | STRUCTURE | NAME |
|---|---|---|
| 34 | 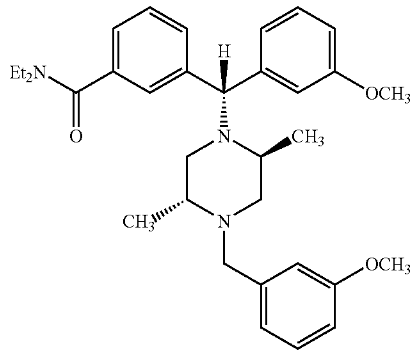 | N,N-Diethyl-3-[(R)-[(2S,5R)-4-(3-methoxybenzyl)-2,5-dimethylpiperazin-1-yl](3-methoxyphenyl)methyl]benzamide |
| 42 | 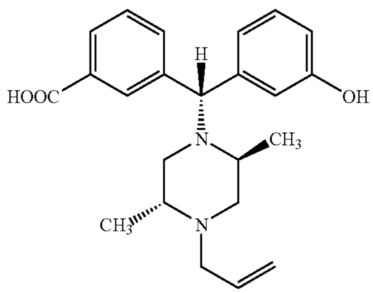 | (+)-3-((alpha-R)-alpha-((2S,5R)-4-Allyl-2,5-dimethyl-1-piperazinyl)-3-hydroxybenzyl)benzoic acid |
| 43 | 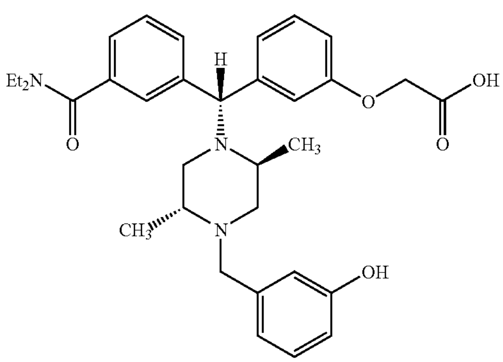 | (3-{(R)-(3-Diethylcarbamoylphenyl)-[(2S,5R)-4-(3-hydroxybenzyl)-2,5-dimethylpiperazin-1-yl]methyl}-phenoxy)acetic acid |
| 44 | 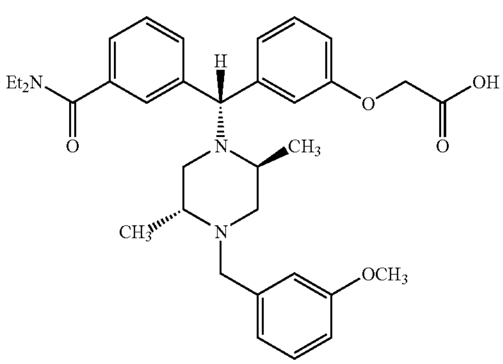 | (3-{(R)-(3-Diethylcarbamoylphenyl)-[(2S,5R)-4-(3-methoxybenzyl)-2,5-dimethylpiperazin-1-yl]methyl}-phenoxy)acetic acid |

TABLE 3-continued

| EXAMPLE NO. | STRUCTURE | NAME |
|---|---|---|
| 45 | 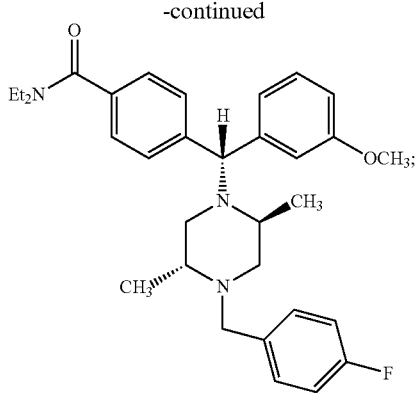 | (3-{(2R,5S)-4-[(R)-(3-Carboxymethoxyphenyl)-(3-diethylcarbamoylphenyl)methyl]-2,5-dimethylpiperazin-1-ylmethyl}phenoxy)acetic acid |

While the invention has been described herein in reference to specific aspects, features and illustrative embodiments of the invention, it will be appreciated that the utility of the invention is not thus limited, but rather extends to and encompasses numerous other aspects, features and embodiments. Accordingly, the claims hereafter set forth are intended to be correspondingly broadly construed, as including all such aspects, features and embodiments, within their spirit and scope.

What is claimed is:

1. A method for delaying the onset of ejaculation in a male subject in need thereof, comprising administering a pharmaceutical formulation comprising a delta opioid receptor agonist in an amount effective to delay the onset of ejaculation in the male subject during sexual stimulation, wherein the delta opioid receptor agonists is an agonist selected from the group consisting of:

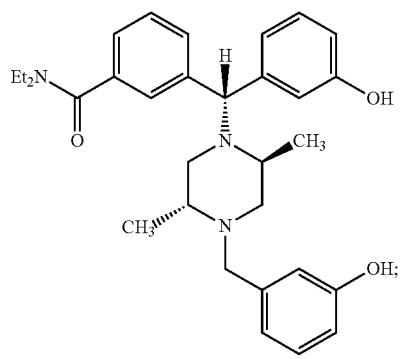

N,N-Diethyl-3-((R)-((2S,5R)-2,5-dimethyl-4-(3-hydroxybenzyl)piperazin-1-yl)(3-hydroxyphenyl)methyl)benzamide -continued 4-((alpha-R)-alpha-((2S,5R)-2,5-Dimethyl-4-(4-fluorobenzyl)-1-piperazinyl)-3-methoxybenzyl-N,N-diethylbenzamide

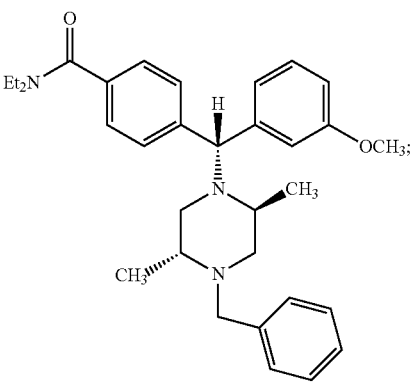

4-(alpha-R)-alpha-((2S,5R)-4-Benzyl-2,5-dimethyl-1-piperazinyl)-3-methoxybenzyl-N,N-diethylbenzamide

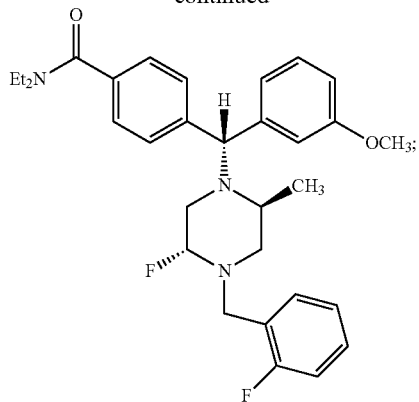

4-((alpha-R)-alpha-((2S,5R)-2,5-Dimethyl-4-(2-fluorobenzyl)-1-piperazinyl)-3-methoxybenzyl-N,N-diethylbenzamide

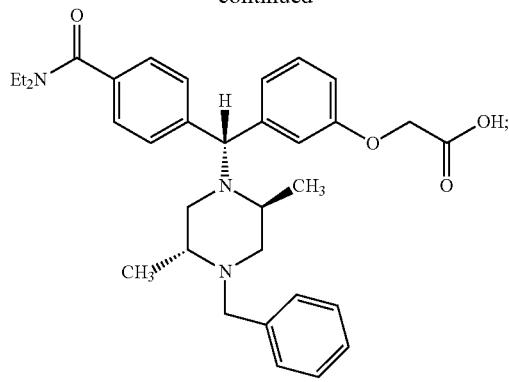

3-((alpha-R)-alpha-((2S,5R)-4-Benzyl-2,5-dimethyl-1-piperazinyl-4-(diethylaminocarbonyl)benzyl)phenoxyacetic acid

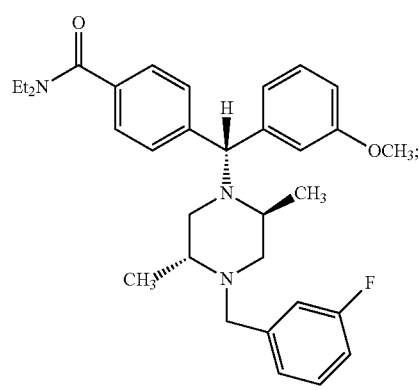

4-((alpha-S)-alpha-((2R,5S)-2,5-Dimethyl-4-(3-fluorobenzyl)-1-piperazinyl)benzyl)-N,N-diethylbenzamide

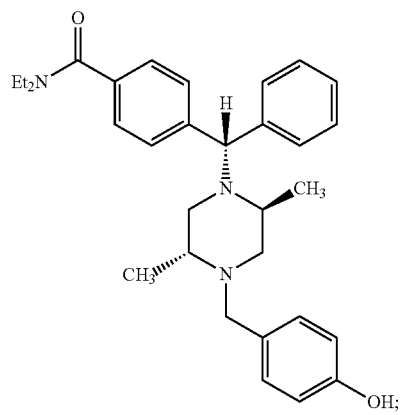

4-((alpha-S)-alpha-((2S,5R)-2,5-Dimethyl-4-(4-hydroxybenzyl)-1-piperazinyl)-benzyl-N,N-diethylbenzamide

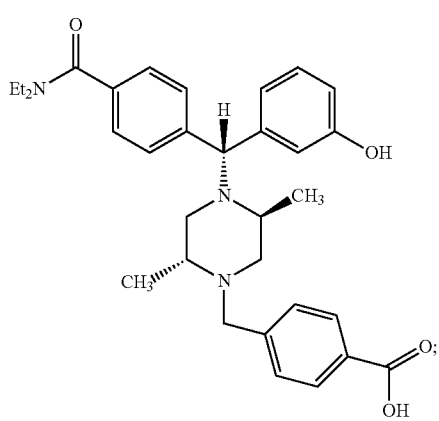

4-{(2R,5S)-4-[(R)-(4-Diethylcarbamoylphenyl)(3-hydroxyphenyl)methyl]-2,5-dimethylpiperazin-1-ylmethyl}benzoic acid

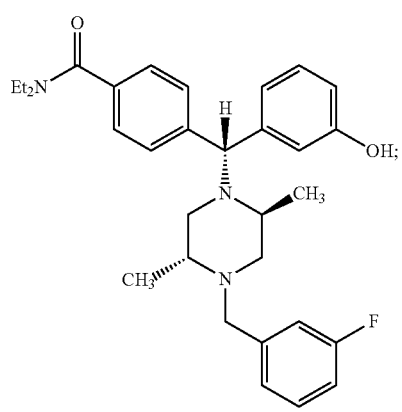

4-((alpha-R)-alpha-((2S,5R)-2,5-Dimethyl-4-(3-fluorobenzyl)-1-piperazinyl)-3-hydroxybenzyl)-N,N-diethylbenzamide

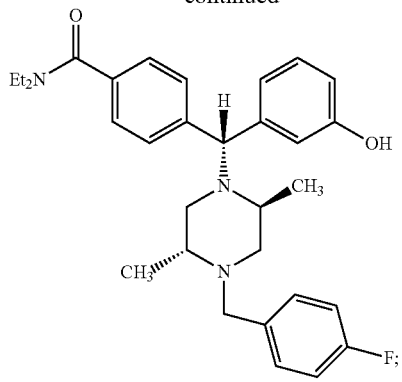

4-((alpha-R)-alpha-((2S,5R)-2,5-Dimethyl-4-(4-flurobenzyl)-1-piperazinyl)-3-hydroxybenzyl)-N,N-diethylbenzamide

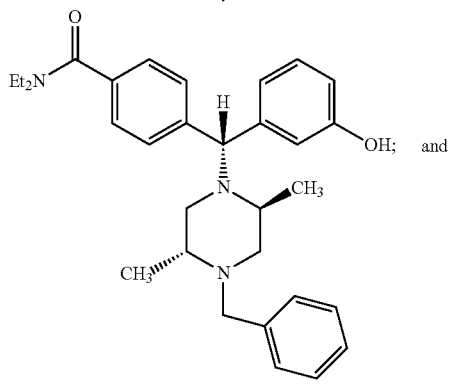
and 4-((alpha-R)-alpha-((2S,5R)-4-Benzyl-2,5-dimethyl-1-piperazinyl)-3-hydroxybenzyl)-N,N-diethylbenzamide

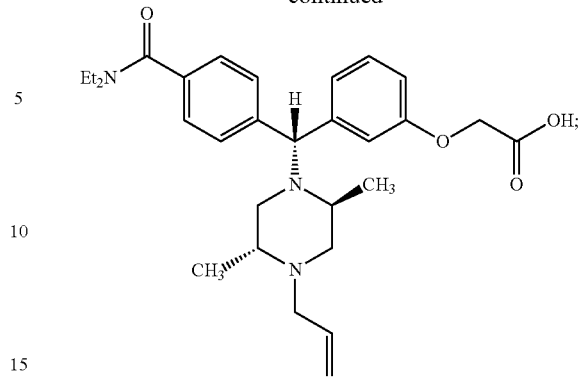

3-((alpha-R)-alpha-((2S,5R)-4-Allyl-2,5-diemthyl-1-piperazinyl)-4-(diethylaminocarbonyl)benzyl) phenoyacetic acid and pharmaceutically effective esters or salts thereof.

2. The method of claim 1, wherein the compound is administered in an oral unitary dose form.

3. The method of claim 1, wherein the delta opioid receptor agonist is administered to the male subject in a dosage amount of from about 1 mg to about 50 mg per kilogram body weight per day.

4. The method according to claim 1, wherein the delta opioid receptor agonist is administered to the male subject in a dosage amount of from about 10 ug to 500 mg per kg of body weight of the subject per day.

5. The method according to claim 1, wherein the delta opioid receptor agonist is administered to the male subject in a dosage amount of from about 50 μg to 75 mg per kilogram of body weight per day.

* * * * *